US010927367B2

(12) United States Patent
Jarjour et al.

(10) Patent No.: US 10,927,367 B2
(45) Date of Patent: *Feb. 23, 2021

(54) CBLB ENDONUCLEASE VARIANTS, COMPOSITIONS, AND METHODS OF USE

(71) Applicant: bluebird bio, Inc., Cambridge, MA (US)

(72) Inventors: Jordan Jarjour, Seattle, WA (US); Kyle Havens, Seattle, WA (US); Anne-Rachel Krostag, Lake Forest Park, WA (US)

(73) Assignee: bluebird bio, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,815

(22) Filed: Nov. 25, 2019

(65) Prior Publication Data

US 2020/0087653 A1    Mar. 19, 2020

Related U.S. Application Data

(63) Continuation of application No. PCT/US2018/034726, filed on May 25, 2018.

(60) Provisional application No. 62/567,417, filed on Oct. 3, 2017, provisional application No. 62/511,194, filed on May 25, 2017.

(51) Int. Cl.
*C12N 9/22* (2006.01)
*C12N 9/16* (2006.01)
*C12N 15/10* (2006.01)
*C12N 5/0783* (2010.01)
*C12N 9/10* (2006.01)
*C12N 15/90* (2006.01)

(52) U.S. Cl.
CPC ......... *C12N 15/102* (2013.01); *C12N 5/0636* (2013.01); *C12N 5/0646* (2013.01); *C12N 9/10* (2013.01); *C12N 15/907* (2013.01); *C12N 2800/80* (2013.01)

(58) Field of Classification Search
CPC .................................... C12N 9/16; C12N 9/22
See application file for complete search history.

(56) References Cited

U.S. PATENT DOCUMENTS

| | | | |
|---|---|---|---|
| 4,751,180 A | 6/1988 | Cousens et al. |
| 4,873,192 A | 10/1989 | Kunkel |
| 4,935,233 A | 6/1990 | Bell et al. |
| 5,804,413 A | 9/1998 | DeLuca |
| 5,837,532 A | 11/1998 | Preston et al. |
| 5,846,782 A | 12/1998 | Wickham et al. |
| 5,994,136 A | 11/1999 | Naldini et al. |
| 6,013,516 A | 1/2000 | Verma et al. |
| 6,682,907 B1 | 1/2004 | Charneau et al. |
| 6,692,736 B2 | 2/2004 | Yu et al. |
| 8,614,092 B2 | 12/2013 | Zhang et al. |
| 8,784,799 B2 | 7/2014 | Samulski et al. |
| 8,809,058 B2 | 8/2014 | Ferrari et al. |
| 8,889,641 B2 | 11/2014 | Asokan et al. |
| 9,012,224 B2 | 4/2015 | Bowles et al. |
| 9,017,967 B2 | 4/2015 | Bonas et al. |
| 9,169,492 B2 | 10/2015 | Monahan et al. |
| 9,169,494 B2 | 10/2015 | Hewitt et al. |
| 10,000,746 B2 * | 6/2018 | Jarjour ............... C12N 9/22 |
| 2011/0179506 A1 | 7/2011 | Grizot |
| 2011/0294217 A1 | 12/2011 | McConnell-Smith et al. |
| 2012/0159659 A1 | 6/2012 | Arnould et al. |
| 2013/0117869 A1 | 5/2013 | Duchateau et al. |
| 2014/0148361 A1 | 5/2014 | Stoddard et al. |
| 2014/0208457 A1 | 7/2014 | Fonfara et al. |
| 2016/0002615 A1 | 1/2016 | Smith et al. |
| 2016/0002671 A1 | 1/2016 | Smith et al. |
| 2016/0102323 A1 | 4/2016 | Jarjour et al. |
| 2016/0130569 A1 | 5/2016 | Jarjour et al. |
| 2016/0184362 A1 | 6/2016 | Duchateau et al. |
| 2018/0171298 A1 | 6/2018 | Duchateau et al. |
| 2020/0109385 A1 | 4/2020 | Jarjour et al. |

FOREIGN PATENT DOCUMENTS

| | | |
|---|---|---|
| WO | WO 91/02788 | 3/1991 |
| WO | WO 96/04394 | 2/1996 |
| WO | WO 98/15637 | 4/1998 |
| WO | WO 99/06583 | 2/1999 |
| WO | WO 2006/010834 | 2/2006 |
| WO | WO 2011/064750 | 6/2011 |
| WO | WO 2017/001572 | 1/2017 |
| WO | WO 2018/218194 | 11/2018 |

OTHER PUBLICATIONS

Balazs et al., "Liposomes for use in gene delivery," Journal of Drug Delivery 2011, 1-12.
Baxter et al., "Engineering domain fusion chimeras from I-Onul family LAGLIDADG homing endonucleases," Nucleic Acids Research, 2012, vol. 40, No. 16, 7985-8000.
Bird, Robert E., et al. "Single-chain antigen-binding proteins." Science (1988); 242.4877: 423-427.
Boissel et al., "megaTALs: a rare-cleaving nuclease architecture for therapeutic genome engineering," Nucleic Acids Research, 2013, 42(4):2591-2601.
Brinkman et al., "Easy quantitative assessment of genome editing by sequence trace decomposition" Nucleic Acids Res. Dec. 16, 2014;42(22).
Certo et al., "Tracking genome engineering outcome at individual DNA breakpoints," Nat Methods. Jul. 10, 2011;8(8):671-6.

(Continued)

*Primary Examiner* — Maryam Monshipouri
(74) *Attorney, Agent, or Firm* — Cooley LLP

(57) ABSTRACT

The present disclosure provides improved genome editing compositions and methods for editing a CBLB gene. The disclosure further provides genome edited cells for the prevention, treatment, or amelioration of at least one symptom of, a cancer, an infectious disease, an autoimmune disease, an inflammatory disease, or an immunodeficiency.

12 Claims, 15 Drawing Sheets

Specification includes a Sequence Listing.

(56) References Cited

OTHER PUBLICATIONS

Certo et al., "Coupling endonucleases with DNA end-processing enzymes to drive gene disruption" Nat Methods. Oct. 2012 ; 9(10): 973-975.

Challita, P. et al., "Multiple modifications in cis elements of the long terminal repeat of retroviral vectors lead to increased expression and decreased DNA methylation in embryonic carcinoma cells." J Virol. (1995); 69(2): 748-755.

Chaudhary, Vuay K., et al. "A rapid method of cloning functional variable-region antibody genes in Escherichia coli as single-chain immunotoxins." Proceedings of the National Academy of Sciences (1990); 87.3: 1066-1070 (and correction).

Clever, J. et al., "RNA Secondary Structure and Binding Sites for gag Gene Products in the 5' Packaging Signal of Human Immunodeficiency Virus Type 1." J. of Virology (1995); 69(4): 2101-2109.

Cullen et al., "Regulatory Pathways Governing HIV-1 Replication", Cell (1989); 58: 423-426.

Cullen, B.R., "Human Immunodeficiency Virus as a Prototypic Complex Retrovirus", Journal of Virology (1991); 65(3): 1053-1056.

Dayhoff et al., (1978) Atlas of Protein Sequence and Structure (Natl. Biomed. Res. Found., Washington, D.C., 8 pages.

De Felipe et al., "Targeting of proteins derived from self-processing polyproteins containing multiple signal sequences." Traffic (2004); 5.8: 616-626.

Desjarlais et al., "Use of a zinc-finger consensus sequence framework and specificity rules to design specific DNA binding proteins." Proceedings of the National Academy of Sciences (1993); 90.6: 2256-2260.

Desjarlais et al., "Length-encoded multiplex binding site determination: application to zinc finger proteins," Proceedings of the National Academy of Sciences (1994); 91.23: 11099-11103.

Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.

Duke et al., Sequence and structural elements that contribute to efficient encephalomyocarditis virus RNA translation, J Virol. Mar. 1992;66(3):1602-9.

Dull et al., "A third-generation lentivirus vector with a conditional packaging system", Journal of Virology (1998); 72(11): 8463-8471.

Gomez-Foix et al, "Adenovirus-mediated Transfer of the Muscle Glycogen Phosphorylase Gene into Hepatocytes Confers Altered Regulation of Glycogen Metabolism," J Biol Chem. Dec. 15, 1992;267(35):25129-34.

Graham et al., "Characteristics of a Human Cell Line Transformed by DNA from Human Adenovirus Type 5," J. gen. Virol. 1977, 36, 59-72.

Graham & Preveck, "Chapter 11, Manipulation of Adenovirus Vectors," Methods in Molecular Biology, vol. 7: Gene transfer and Expression Protocols, 1991.

Graham & Preveck, "Adenovirus-Based Expression Vectors and Recombinant Vaccines" Vaccines: New Approaches to Immunological Problems, 1992.

Grunhaus, A., and Horwitz, M. S. "Adenoviruses as cloning vectors," Semin. Virol. 1992; 3, 237-252.

Herz & Gerard, "Adenovirus-mediated transfer of low density lipoprotein receptor gene acutely accelerates cholesterol clearance in normal mice," PNAS, 1993, vol. 90, 2812-2816.

Huang et al., "Role of the hepatitis B virus posttranscriptional regulatory element in export of intronless transcripts," Molecular and Cellular Biology (1995); 15(7): 3864-3869.

Huez et al., "Two independent internal ribosome entry sites are involved in translation initiation of vascular endothelial growth factor mRNA," Mol Cell Biol. Nov. 1998;18(11):6178-90.

International Search Report and Written Opinion dated Aug. 22, 2018, for International Application No. PCT/US2018/034726, 9 pages.

International Search Report and Written Opinion dated Dec. 31, 2018, for International Application No. PCT/US2018/054347, 14 pages.

Irion, S. et al., "Identification and targeting of the ROSA26 locus in human embryonic stem cells", Nat Biotechnol. (2007); 25(12):1477-1482.

Jackson, et al., "The novel mechanism of initiation of picornavirus RNA translation", Trends Biochem Sci. (1990); 15(12): 477-483.

Jackson, et al., "Internal initiation of translation in eukaryotes: the picornavirus paradigm and beyond", RNA. (1995); 1(10): 985-1000.

Jarjour et al., "High-resolution profiling of homing endonuclease binding and catalytic specificity using yeast surface display," 2009. Nuc. Acids Res. 37(20): 6871-6880.

Jones & Shenk, Isolation of Deletion and Substitution Mutants of Adenovirus Type 5, Cell 1978, vol. 13, 181-188.

Katzav et al. "Mutations of c-Cbl in myeloid malignancies," Oncotarget, May 4, 2015 (May 4, 2015), vol. 6, No. 13, pp. 10689-10696.

Kay et al., "A bacterial effector acts as a plant transcription factor and induces a cell size regulator," Science. Oct. 26, 2007;318(5850):648-51.

Kim, Yang-Gyun,et al. "Hybrid restriction enzymes: zinc finger fusions to Fok I cleavage domain." Proceedings of the National Academy of Sciences (1996); 93.3: 1156-1160.

Kunkel, TA. "Rapid and efficient site-specific mutagenesis without phenotypic selection", Proc Natl Acad Sci U S A. (1985); 82(2): 488-492.

Kunkel, et al "Rapid and efficient site-specific mutagenesis without phenotypic selection", Methods in Enzymol. (1987); 154: 367-382.

Kurokawa et al., "Adaptation of intronic homing endonuclease for successful horizontal transmission," FEBS Journal 272 (2005) 2487-2496.

Kutner, et al., "Simplified production andconcentration of HIV-1-based lentiviral vectors using HYPERFlask vessels and anion exchange membrane chromatography", BMC Biotechnol. (2009); 9:10. p. 1-7.

Kutner et al., "Production, concentration and titration of pseudotyped HIV-1-based lentiviral vectors", Nature Protocols (2009); 4: 495-505.

Le Gal La Salle et al., "An Adenovirus Vector for Gene Transfer into Neurons and Glia in the Brain," Science Feb. 12, 1993, vol. 259, 988-990.

Levrero et al., "Defective and nondefective adenovirus vectors for expressing foreign genes in vitro and in vivo," Gene 1991; 101:195-202.

Liu et al., "HnRNP L binds a cis-acting RNA sequence element that enables intron-dependent gene expression," Genes & Dev. (1995); 9: 1766-1780.

Liu et al., "Design of polydactyl zinc-finger proteins for unique addressing within complex genomes," Proceedings of the National Academy of Sciences (1997); 94.11: 5525-5530.

Liu et al., "Poly(cationic lipid)-mediated in vivo gene delivery to mouse liver," Gene Ther. Jan. 2003;10(2):180-7.

Lo et al. "An E3 ubiquitin ligase c-Cbl: a new therapeutic target of lung cancer in cell and animal models," Cancer, May 23, 2011 (May 23, 2011), vol. 117, No. 23, pp. 5344-5350.

Maratea et al., "Deletion and fusion analysis of the phage phi X174 lysis gene E," Gene. 1985;40(1):39-46.

Murphy et al., "Genetic construction, expression, and melanoma-selective cytotoxicity of a diphtheria toxin-related alpha-melanocyte-stimulating hormone fusion protein," Proc Natl Acad Sci U S A. Nov. 1986;83(21):8258-62.

Naldini L. et al., "Efficient transfer, integration, and sustained long-term expression of the transgene in adult rat brains injected with a lentiviral vector", Proc Natl Acad Sci USA (1996); 93(21): 11382-11388.

Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.

Pomerantz, et al., "Structure-based design of transcription factors." Science (1995); 267.5194: 93-96.

(56) References Cited

OTHER PUBLICATIONS

Pomerantz, et al., "Analysis of homeodomain function by structure-based design of a transcription factor," Proc Natl Acad Sci U S A. Oct. 10, 1995;92(21):9752-6.

Ragot et al., "Efficient adenovirus-mediated transfer of a human minidystrophin gene to skeletal muscle of mdx mice," Nature Feb. 18, 1993; vol. 361: 647-650.

Rosenfeld et al., "Adenovirus-Mediated Transfer of a Recombinant α1-Antitrypsin Gene to the Lung Epithelium in Vivo," Science Apr. 19, 1991; vol. 252: 431-434.

Rosenfeld et al., "In vivo transfer of the human cystic fibrosis transmembrane conductance regulator gene to the airway epithelium," Cell, Jan. 10, 1992; vol. 68: 143-155.

Ryan, M. et al., "Virus-encoded proteinases of the picornavirus super-group." J Gen Virol. (1997); 78 (Pt 4): 699-723.

Sather et al., "Efficient modification of CCR5 in primary human hematopoietic cells using a megaTAL nuclease and AAV donor template," www.ScienceTranslationalMedicine.org, Sep. 30, 2015, vol. 7, Issue 307, 14 pages.

Sterman et al., "Adenovirus-mediated herpes simplex virus thymidine kinase/ganciclovir gene therapy in patients with localized malignancy: results of a phase I clinical trial in malignant mesothelioma," Hum Gene Ther. May 1, 1998;9(7):1083-92.

Stoddard, "Homing endonuclease structure and function," Quarterly Reviews of Biophysics 2005; 38(1): pp. 49-95.

Szeto et al., "Mining Endonuclease Cleavage Determinants in Genomic Sequence Data," The Journal of Biological Chemistry, vol. 286, No. 37, pp. 32617-32627, Sep. 16, 2011.

Szymczak, Andrea L., et al. "Correction of multi-gene deficiency in vivo using a single'self-cleaving' 2A peptide-based retroviral vector." Nature Biotechnology (2004); 22.5: 589-594.

Takeuchi et al:"Tapping natural reservoirs of homing endonucleases for targeted gene modification", Proceedings of the National Academy of Sciences, National Academy of Sciences, vol. 108, o. 32, Aug. 1, 2011 {Aug. 1, 2011), pp. 13077-13082.

Takeuchi et al., "Redesign of extensive protein-DNA interfaces of meganucleases using iterative cycles of in vitro compartmentalization," PNAS, Mar. 18, 2014, vol. 111, No. 11, 4061-4066.

Takeuchi et al., "Engineering of customized meganucleases via in vitro compartmentalization and in cellulo optimization," Methods Mol Biol. 2015; 1239: 105-132.

Zennou et al., "HIV-1 genome nuclear import is mediated by a central DNA flap," Cell. Apr. 14, 2000;101(2):173-85.

Zufferey et al., "Multiply attenuated lentiviral vector achieves efficient gene delivery in vivo", Nat Biotechnol. (1997), 15(9): 871-875.

Zufferey, R. et al., "Woodchuck hepatitis virus posttranscriptional regulatory element enhances expression of transgenes delivered by retroviral vectors." J Virol. (1999); 73(4): 2886-2892.

Hensgens et al., "Two Intron Sequences in Yeast Mitochondrial COX1 Gene: Homology among URF-Containing Introns and Strain-Dependent Variation in Flanking Exons," Cell, vol. 32, 379-389, Feb. 1983.

Extended European Search Report dated Dec. 23, 2020, for European Application No. 18806825.8, 12 pages.

* cited by examiner

FIGURE 5

```
                 1            10         20         30         40         50         60         70
                 |            |          |          |          |          |          |          |
1. I-Onul        SINPWILTGFADAEGCFRLDIRNANDLRAGYRTRLSFEIVLHNKDKSILENIQSTWKVGTIYNAGDNAVRL
2. Cbib.E3       SINPWILTGFADAEGSFLLRIRNNNKSSVGYSTELGFQITLHNKDKSILENIQSTWKVGVIANSGDNAVSL
3. Cbib.F6       SINPWILTGFADAEGCFRLDIRNANDLRAGYRTRLAFEIVLHNKDKSILENIQSTWKVGTIYNAGDNAVRL
4. Cbib.E6       SINPWILTGFADAEGCFRLDIRNANDLRAGYRTRLAFEIVLHNKDKSILENIQSTWKVGTIYNAGDNAVRL
5. Cbib.D2       SINPWILTGFADAEGCFRLDIRNANDLRSGYRTRLSFEISLHNKDKSILENIQSTWKVGKIYNAGDNAVRL
6. Cbib.C2       SINPWILTGFADAEGCFGLYIHNSNVLRSGYRTRLSFEIVLHNKDKSILENIQSTWKVGTIYNAGDNAVRL
7. Cbib.B5       SINPWILTGFADAEGCFRLDIHNANVLRSGYRTRLSFEIVLHNKDKSILENIQSTWKVGTIYNAGDNAVRL
8. Cbib.A8       SINPWILTGFADAEGCFRLDIRNANDLRAGYRTRLAFEIVLHNKDKSILENIQSTWKVGTIYNAGDNAVRL 80           90        100        110        120        130        140
                 |            |          |          |          |          |          |
1. I-Onul        QVTRFEDLKVIIDHFEKYPLITQKLGDYKLFKQAFSVMENKEHLKENGIKELVRIKAKMNWGLNDELKKAF
2. Cbib.E3       KVTRFEDLKVIIDHFEKYPLITQKLGDYKLFKQAFSVMENKEHLKENGIKELVRIKAKLNWGLTDELKKAF
3. Cbib.F6       QVTRFEDLKVIIDHFEKYPLITQKLGDYKLFKQAFSVMENKEHLKENGIKELVRIKAKMNWGLNDELKKAF
4. Cbib.E6       QVTRFEDLKVIIDHFEKYPLITQKLGDYKLFKQAFSVMENKEHLKENGIKELVRIKAKMNWGLNDELKKAF
5. Cbib.D2       QVTRFEDLKVIIDHFEKYPLITQKLGDYKLFKQAFSVMENKEHLKENGIKELVRIKAKMNWGLNDELKKAF
6. Cbib.C2       QVTRFEDLKVIIDHFEKYPLITQKLGDYKLFKQAFSLMENKEHLKENGIKELVRIKAKMNWGLNDELKKAF
7. Cbib.B5       QVTRFEDLKVIIDHFEKYPLITQKLGDYKLFKQAFSLMENKEHLKENGIKELVRIKAKMNWGLNDELKKAF
8. Cbib.A8       QVTRFEDLKVIIGHFEKYPLITQKLGDYKLFKQAFSVMENKEHLKENGIKELVRIKAKMNWGLNDELKKAF
```

FIGURE 5 (cont.)

```
                   150         160         170         180         190         200         210
                   |           |           |           |           |           |           |
1. I-Onul          PENISKERPLINKMIPNLKWLAGFTSGDGSFMVELMKNKNNVIVRVRLRFSISQHIRDKNLMNSLITYLGC
2. Cbib.E3         PENISKERSLINKNIPNFKWLAGFTSGEGCFFVNLIKSKSLGVQLVFSITQHIRDKNLMNSLITYLGC
3. Cbib.F6         PENISKERPLINKNIPNLKWLAGFTSGDGSFVVELKKRRSPVKVGVRLRFSISQHIRDKNLMNSLITYLGC
4. Cbib.E6         PENISKERPLINKNIPNLKWLAGFTSGDGSFMVELMKNKNNVIVRVRLRFSISQHIRDKNLMNSLITYLGC
5. Cbib.D2         PENISKERPLINKNIPNLKWLAGFTSGDGSFMVELMKNKNNVIVRVRLRFSISQHIRDKNLMNSLITYLGC
6. Cbib.C2         PENISKERPLINKNIPNLKWLAGFTSGDGSFVVELKKRRSPVKVGVRLRFGITQHIRDKNLMNSLITYLGC
7. Cbib.B5         PENISKERPLINKNIPNLKWLAGFTSGDGSFMVELMKNKNNVIVRVRLRFSISQHIRDKNLMNSLITYLGC
8. Cbib.A8         PENISKERPLINKNIPNLKWLAGFTSGDGSFMVELMKNKNNVIVRVRLRFSISQHIRDKNLMNSLITYLGC 220         230         240         250         260         270         280
                   |           |           |           |           |           |           |
1. I-Onul          GRIVENNKSEHSWLEFIVTKFSDINDKIIPVFQENTLIGVKLEDFEDWCKVAKLIEEKKHLTESGLDEIKK
2. Cbib.E3         GYIKEKNKSEFSWLDFVVTKFSDINDKIIPVFQENTLIGVKLEDFEDWCKVAKLIEEKKHLTESGLDEIKK
3. Cbib.F6         GRIVENNKSEHSWLEFIVTKFSDINDKIIPVFQENTLIGVKLEDFEDWCKVAKLIEEKKHLTESGLDEIKK
4. Cbib.E6         GRIVENNKSEHSWLEFIVTKFSDINDKIIPVFQENTLIGVKLEDFEDWCKVAKLIEEKKHLTESGLDEIKK
5. Cbib.D2         GRIVENNKSEHSWLEFIVTKFSDINDKIIPVFQENTLIGVKLEDFEDWCKVAKLIEEKKHLTESGLDEIKK
6. Cbib.C2         GRIVENNKSEHSWLEFIVTKFSDINDKIIPVFQENTLIGVKLEDFEDWCKVAKLIEEKKHLTESGLDEIKK
7. Cbib.B5         GRIVENNKSEHSWLEFIVTKFSDINDKIIPVFQENTLIGVKLEDFEDWCKVAKLIEEKKHLTESGLDEIKK
8. Cbib.A8         GRIVENNKSEHSWLEFIVTKFSDINDKIIPVFQENTLIGVKLEDFEDWCKVAKLIEEKKHLTESGLDEIKK
```

FIGURE 5 (cont.)

```
              290    293         300
               |      |           |
              IKLNMNKGRVFSGR**
1. I-OnuI     IKLNMNKGR
2. CbIb.E3    IKLNMNKGRVFSGR**
3. CbIb.F6    IKLNMNKGRVFSGR**
4. CbIb.E6    IKLNMNKGRVFSGR**
5. CbIb.D2    IKLNMNKGRVFSGR**
6. CbIb.C2    IKLNMNKGRVFSGR**
7. CbIb.B5    IKLNMNKGRVFSGR**
8. CbIb.A8    IKLNMNKGRVFSGR**
```

CBLB ENDONUCLEASE VARIANTS, COMPOSITIONS, AND METHODS OF USE

CROSS REFERENCE TO RELATED APPLICATIONS

This application is a continuation of International PCT Patent Application No. PCT/US2018/034726, which was filed on May 25, 2018, now pending, which claims the benefit under 35 U.S.C. § 119(e) of U.S. Provisional Application No. 62/567,417, filed Oct. 3, 2017, and U.S. Provisional Application No. 62/511,194, filed May 25, 2017, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_087_03US_ST25.txt. The text file is 152 KB, created on Nov. 25, 2019, and is being submitted electronically via EFS-Web, concurrent with the filing of the specification.

BACKGROUND

Technical Field

The present disclosure relates to improved genome editing compositions. More particularly, the disclosure relates to nuclease variants, compositions, and methods of using the same for editing the human casitas B-lineage (Cbl) lymphoma proto-oncogene B (CBLB) gene.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

The immune system has a key role in detecting and combating human cancer. The majority of transformed cells are quickly detected by immune sentinels and destroyed through the activation of antigen-specific T cells via clonally expressed T cell receptors (TCR). Accordingly, cancer can be considered an immunological disorder, a failure of immune system to mount the necessary anti-tumor response to durably suppress and eliminate the disease. In order to more effectively combat cancer, certain immunotherapy interventions developed over the last few decades have specifically focused on enhancing T cell immunity. These treatments have yielded only sporadic cases of disease remission, and have not had substantial overall success.

Most recently, adoptive cellular therapy strategies, which are based on the isolation, modification, expansion and reinfusion of T cells, have been explored and tested in early stage clinical trials. T cells have often been the effector cells of choice for cancer immunotherapy due to their selective recognition and powerful effector mechanisms. These treatments have shown mixed rates of success, but a small number of patients have experienced durable remissions, highlighting the as-yet unrealized potential for T cell-based immunotherapies.

Successful recognition of tumor cell associated antigens by cytolytic T cells initiates targeted tumor lysis and underpins any effective cancer immunotherapy approach. Tumor-infiltrating T cells (TILs) express TCRs specifically directed tumor-associated antigens; however, substantial numbers of TILs are limited to only a few human cancers. Engineered T cell receptors (TCRs) and chimeric antigen receptors (CARs) potentially increase the applicability of T cell-based immunotherapy to many cancers and other immune disorders.

In addition, state of the art engineered T cells are still regulated by a complex immunosuppressive tumor microenvironment that consists of cancer cells, inflammatory cells, stromal cells and cytokines. Among these components, cancer cells, inflammatory cells and suppressive cytokines adversely impact T cell phenotype and function. Collectively, the tumor microenvironment drives T cells to terminally differentiate into exhausted T cells.

T cell exhaustion is a state of T cell dysfunction in a chronic environment marked by increased expression of, or increased signaling by inhibitory receptors; reduced effector cytokine production; and a decreased ability to persist and eliminate cancer. Exhausted T cells also show loss of function in a hierarchical manner: decreased IL-2 production and ex vivo killing capacity are lost at the early stage of exhaustion, TNF-α production is lost at the intermediate stage, and IFN-γ and GzmB production are lost at the advanced stage of exhaustion. Most T cells in the tumor microenvironment differentiate into exhausted T cells and lose the ability to eliminate cancer and are eventually cleared.

To date there have been no demonstrable clinical examples of adoptive cellular therapies with increased persistence and resistance to the immunosuppressive tumor microenvironment.

BRIEF SUMMARY

The present disclosure generally relates, in part, to compositions comprising homing endonuclease variants and megaTALs that cleave a target site in the human casitas B-lineage (Cbl) lymphoma proto-oncogene B (CBLB) gene and methods of using the same.

In various embodiments, the present disclosure contemplates, in part, a polypeptide comprising a homing endonuclease (HE) variant that cleaves a target site in the human CBLB gene.

In particular embodiments, the HE variant is an LAGLIDADG homing endonuclease (LHE) variant.

In some embodiments, the polypeptide comprises a biologically active fragment of the HE variant.

In certain embodiments, the biologically active fragment lacks the 1, 2, 3, 4, 5, 6, 7, or 8 N-terminal amino acids compared to a corresponding wild type HE.

In some embodiments, the biologically active fragment lacks the 4 N-terminal amino acids compared to a corresponding wild type HE.

In further embodiments, the biologically active fragment lacks the 8 N-terminal amino acids compared to a corresponding wild type HE.

In particular embodiments, the biologically active fragment lacks the 1, 2, 3, 4, 5, or 6 C-terminal amino acids compared to a corresponding wild type HE.

In particular embodiments, the biologically active fragment lacks the C-terminal amino acid compared to a corresponding wild type HE.

In additional embodiments, the biologically active fragment lacks the 2 C-terminal amino acids compared to a corresponding wild type HE.

In particular embodiments, the HE variant is a variant of an LHE selected from the group consisting of: I-CreI and I-SceI.

In certain embodiments, the HE variant is a variant of an LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

In some embodiments, the HE variant is a variant of an LHE selected from the group consisting of: I-CpaMI, I-HjeMI, I-OnuI, I-PanMI, and SmaMI.

In additional embodiments, the HE variant is an I-OnuI LHE variant.

In particular embodiments, the HE variant comprises one or more amino acid substitutions in the DNA recognition interface at amino acid positions selected from the group consisting of: 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In certain embodiments, the HE variant comprises at least 5, at least 15, preferably at least 25, more preferably at least 35, or even more preferably at least 40 or more amino acid substitutions in the DNA recognition interface at amino acid positions selected from the group consisting of: 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In particular embodiments, the HE variant comprises one or more amino acid substitutions at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In certain embodiments, the HE variant comprises at least 5, at least 15, preferably at least 25, more preferably at least 35, or even more preferably at least 40 or more amino acid substitutions at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In particular embodiments, the HE variant comprises at least 5, at least 15, preferably at least 25, more preferably at least 35, or even more preferably at least 40 or more amino acid substitutions in at least one position selected from the position group consisting of positions: 24, 26, 28, 30, 32, 34, 35, 36, 37, 38, 40, 42, 44, 46, 48, 68, 70, 72, 78, 80, 92, 116, 138, 143, 159, 168, 178, 180, 182, 184, 186, 188, 189, 190, 191, 192, 193, 195, 197, 199, 201, 203, 207, 223, 225, 227, 232, 236, and 238 of any one of SEQ ID NOs: 1-5, or a biologically active fragment thereof.

In some embodiments, the HE variant comprises at least 5, at least 15, preferably at least 25, more preferably at least 35, or even more preferably at least 40 or more of the following amino acid substitutions: S24C, L26R, L26G, R28D, R28Y, R30H, N32A, N32S, K34D, K34V, S35L, S36R, V37A, V37S, S40R, E42R, G44A, G44S, Q46E, T48V, T48S, V68T, V68K, A70Y, S72A, S78R, K80Q, D92G, V116L, L138M, T143N, S159P, F168L, E178D, C180S, F182V, F182M, N184E, I186K, I186M, S188R, S188N, K189R, S190N, K191P, K191N, L192V, G193K, G193I, Q195G, Q195R, Q197R, V199R, S201G, T203S, K207R, Y223R, K225V, K227N, F232H, D236E, and V238I of any one of SEQ ID NOs: 1-5, or a biologically active fragment thereof.

In further embodiments, the HE variant comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44A, Q46E, T48V, V68T, A70Y, S72A, S78R, K80Q, L138M, T143N, F168L, E178D, C180S, F182V, N184E, I186K, S188R, K189R, K191P, L192V, G193K, Q195G, Q197R, V199R, K207R, Y223R, K225V, K227N, F232H, D236E, and V238I of any one of SEQ ID NOs: 1-5, or a biologically active fragment thereof.

In particular embodiments, the HE variant comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44A, Q46E, T48V, V68T, A70Y, S72A, S78R, K80Q, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of any one of SEQ ID NOs: 1-5, or a biologically active fragment thereof.

In certain embodiments, the HE variant comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44S, Q46E, T48S, V68T, A70Y, S72A, S78R, K80Q, D92G, V116L, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of any one of SEQ ID NOs: 1-5, or a biologically active fragment thereof.

In some embodiments, the HE variant comprises at least 5, at least 15, preferably at least 25, more preferably at least 35, or even more preferably at least 40 or more of the following amino acid substitutions: S24C, L26R, R28D, R30H, N32A, K34V, S35L, S36R, V37S, S40R, E42R, G44S, Q46E, T48V, V68T, V68K, A70Y, S72A, S78R, K80Q, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of any one of SEQ ID NOs: 1-5, or a biologically active fragment thereof.

In particular embodiments, the HE variant comprises at least 5, at least 15, preferably at least 25, more preferably at least 35, or even more preferably at least 40 or more of the following amino acid substitutions: S24C, L26G, R28Y, R30H, N32S, K34V, S35L, S36R, V37S, S40R, E42R, G44S, Q46E, T48S, V68T, A70Y, S72A, S78R, K80Q, V116L, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of any one of SEQ ID NOs: 1-5, or a biologically active fragment thereof.

In certain embodiments, the HE variant comprises at least 5, at least 15, preferably at least 25, more preferably at least 35, or even more preferably at least 40 or more of the following amino acid substitutions: S24C, L26R, R28D, R30H, N32A, K34V, S35L, S36R, V37S, S40R, E42R, G44S, Q46E, T48V, V68T, A70Y, S72A, S78R, K80Q, V116L, L138M, T143N, S159P, F168L, E178D, C180S, F182V, N184E, I186K, S188R, K189R, K191P, L192V, G193K, Q195G, Q197R, V199R, S201G, K207R, Y223R, K225V, K227N, F232H, D236E, and V238I of any one of SEQ ID NOs: 1-5, or a biologically active fragment thereof.

In further embodiments, the HE variant comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44A, Q46E, T48V, V68T, A70Y, S72A, S78R, K80Q, D92G, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of any one of SEQ ID NOs: 1-5, or a biologically active fragment thereof.

In particular embodiments, the HE variant comprises an amino acid sequence that is at least 80%, preferably at least 85%, more preferably at least 90%, or even more preferably at least 95% identical to the amino acid sequence set forth in any one of SEQ ID NOs: 6-12, or a biologically active fragment thereof.

In some embodiments, the HE variant comprises the amino acid sequence set forth in SEQ ID NO: 6, or a biologically active fragment thereof.

In additional embodiments, the HE variant comprises the amino acid sequence set forth in SEQ ID NO: 7, or a biologically active fragment thereof.

In particular embodiments, the HE variant comprises the amino acid sequence set forth in SEQ ID NO: 8, or a biologically active fragment thereof.

In particular embodiments, the HE variant comprises the amino acid sequence set forth in SEQ ID NO: 9, or a biologically active fragment thereof.

In further embodiments, the HE variant comprises the amino acid sequence set forth in SEQ ID NO: 10, or a biologically active fragment thereof.

In certain embodiments, the HE variant comprises the amino acid sequence set forth in SEQ ID NO: 11, or a biologically active fragment thereof.

In certain embodiments, the HE variant comprises the amino acid sequence set forth in SEQ ID NO: 12, or a biologically active fragment thereof.

In some embodiments, the polypeptide binds the polynucleotide sequence set forth in SEQ ID NO: 20.

In particular embodiments, the polypeptide further comprises a DNA binding domain.

In additional embodiments, the DNA binding domain is selected from the group consisting of: a TALE DNA binding domain and a zinc finger DNA binding domain.

In certain embodiments, the TALE DNA binding domain comprises about 9.5 TALE repeat units to about 15.5 TALE repeat units.

In further embodiments, the TALE DNA binding domain binds a polynucleotide sequence in the CBLB gene.

In particular embodiments, the TALE DNA binding domain binds the polynucleotide sequence set forth in SEQ ID NO: 21.

In particular embodiments, the polypeptide binds and cleaves the polynucleotide sequence set forth in SEQ ID NO: 22.

In particular embodiments, the zinc finger DNA binding domain comprises 2, 3, 4, 5, 6, 7, or 8 zinc finger motifs.

In additional embodiments, the polypeptide further comprises a peptide linker and an end-processing enzyme or biologically active fragment thereof.

In certain embodiments, the polypeptide further comprises a viral self-cleaving 2A peptide and an end-processing enzyme or biologically active fragment thereof.

In further embodiments, the end-processing enzyme or biologically active fragment thereof has 5'-3' exonuclease, 5'-3' alkaline exonuclease, 3'-5' exonuclease, 5' flap endonuclease, helicase, TdT, or template-independent DNA polymerase activity.

In some embodiments, the end-processing enzyme comprises Trex2 or a biologically active fragment thereof.

In further embodiments, the polypeptide comprises the amino acid sequence set forth in any one of SEQ ID NOs: 13-19, or a biologically active fragment thereof.

In additional embodiments, the polypeptide comprises the amino acid sequence set forth in SEQ ID NO: 13, or a biologically active fragment thereof.

In particular embodiments, the polypeptide comprises the amino acid sequence set forth in SEQ ID NO: 14, or a biologically active fragment thereof.

In certain embodiments, the polypeptide comprises the amino acid sequence set forth in SEQ ID NO: 15, or a biologically active fragment thereof.

In certain embodiments, the polypeptide comprises the amino acid sequence set forth in SEQ ID NO: 16, or a biologically active fragment thereof.

In some embodiments, the polypeptide comprises the amino acid sequence set forth in SEQ ID NO: 17, or a biologically active fragment thereof.

In particular embodiments, the polypeptide comprises the amino acid sequence set forth in SEQ ID NO: 18, or a biologically active fragment thereof.

In further embodiments, the polypeptide comprises the amino acid sequence set forth in SEQ ID NO: 19, or a biologically active fragment thereof.

In particular embodiments, the polypeptide cleaves the human CBLB gene at a polynucleotide sequence set forth in SEQ ID NOs: 20 or 22.

In various embodiments, the present disclosure provides, in part, a polynucleotide encoding a polypeptide contemplated herein.

In some embodiments, the present disclosure provides, in part, an mRNA encoding a polypeptide contemplated herein.

In particular embodiments, the present disclosure provides, in part, a cDNA encoding a polypeptide contemplated herein.

In various embodiments, the present disclosure provides, in part, a vector comprising a polynucleotide encoding a polypeptide contemplated herein.

In various embodiments, the present disclosure provides, in part, a cell comprising a polypeptide contemplated herein.

In additional embodiments, the present disclosure provides, in part, a cell comprising a polynucleotide encoding a polypeptide contemplated herein.

In further embodiments, the present disclosure provides, in part, a cell comprising a vector contemplated herein.

In some embodiments, the present disclosure provides, in part, a cell comprising one or more genome modifications introduced by a polypeptide contemplated herein.

In particular embodiments, the cell comprises a polynucleotide encoding one or more of an immunopotency enhancer, an immunosuppressive signal damper, or an engineered antigen receptor.

In further embodiments, the polynucleotide further comprises an RNA polymerase II promoter operably linked to the polynucleotide encoding the immunopotency enhancer, immunosuppressive signal damper, or engineered antigen receptor.

In some embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter.

In additional embodiments, the polynucleotide further encodes one or more self-cleaving viral peptides operably linked to, interspersed between, and/or flanking the immunopotency enhancer, immunosuppressive signal damper, or engineered antigen receptor.

In particular embodiments, the self-cleaving viral peptide is a 2A peptide.

In certain embodiments, the polynucleotide further comprises a heterologous polyadenylation signal.

In particular embodiments, the immunosuppressive signal damper comprises an enzymatic function that counteracts an immunosuppressive factor.

In additional embodiments, the immunosuppressive signal damper comprises kynureninase activity.

In particular embodiments, the immunosuppressive signal damper comprises: an exodomain that binds an immunosuppressive factor, optionally wherein the exodomain is an antibody or antigen binding fragment thereof; an exodomain that binds an immunosuppressive factor and a transmembrane domain; or an exodomain that binds an immunosuppressive factor, a transmembrane domain, and a modified endodomain that is unable to transduce immunosuppressive signals to the cell.

In further embodiments, the immunopotency enhancer is selected from the group consisting of: a bispecific T cell engager molecule (BiTE), an immunopotentiating factor, and a flip receptor.

In some embodiments, the immunopotentiating factor is selected from the group consisting of: a cytokine, a chemokine, a cytotoxin, a cytokine receptor, and variants thereof.

In some embodiments, the flip receptor comprises a TGFβRII exodomain and transmembrane domain; and an endodomain from TLR4, CD28, CD134, CD137, CD278, and/or CD3ζ fused in frame to the C-terminal end of the TGFβRII transmembrane domain.

In particular embodiments, the flip receptor comprises a TGFβRII exodomain; a transmembrane domain isolated from a TLR4, CD3ζ, CD4, CD8a, CD28, CD134, or CD137 polypeptide; and an endodomain from TLR4, CD28, CD134, CD137, CD278, and/or CD3ζ fused in frame to the C-terminal end of the TGFβRII exodomain.

In certain embodiments, the flip receptor comprises a TGFβRII exodomain; and a transmembrane domain and endodomain isolated from a TLR4, CD3ζ, CD4, CD8a, CD28, CD134, or CD137 polypeptide fused in frame to the C-terminal end of the TGFβRII exodomain.

In particular embodiments, the engineered antigen receptor is selected from the group consisting of: an engineered TCR, a CAR, a Daric, or a zetakine.

In additional embodiments, the engineered receptor is not integrated into the CBLB gene.

In further embodiments, the polynucleotide encoding one or more of an immunopotency enhancer, an immunosuppressive signal damper, or an engineered antigen receptor is integrated into the CBLB gene.

In further embodiments, a donor repair template comprises the polynucleotide encoding one or more of an immunopotency enhancer, an immunosuppressive signal damper, or an engineered antigen receptor is integrated into the CBLB gene at a DNA double stranded break site introduced by a polypeptide contemplated herein.

In particular embodiments, the cell is a hematopoietic cell.

In some embodiments, the cell is a T cell.

In particular embodiments, the cell is a CD3+, CD4+, and/or CD8+ cell.

In additional embodiments, the cell is an immune effector cell.

In particular embodiments, the cell is a cytotoxic T lymphocytes (CTLs), a tumor infiltrating lymphocytes (TILs), or a helper T cells.

In certain embodiments, the cell is a natural killer (NK) cell or natural killer T (NKT) cell.

In a preferred embodiment, the cell is a T cell that has been genetically modified to express an engineered antigen receptor.

In a preferred embodiment, the cell is a T cell that has been genetically modified to express a chimeric antigen receptor (CAR) or engineered T cell receptor (TCR).

In additional embodiments, the source of the cell is peripheral blood mononuclear cells, bone marrow, lymph nodes tissue, cord blood, thymus tissue, tissue from a site of infection, ascites, pleural effusion, spleen tissue, or tumors.

In some embodiments, the cell comprises one or more modified CBLB alleles.

In further embodiments, the one or more modified CBLB alleles are non-functional or have substantially reduced CBLB function and/or activity.

In particular embodiments, the cell comprises a nucleic acid encoding an immunopotency enhancer or immunosuppressive signal damper introduced into the one or more modified CBLB alleles and the cell further comprises engineered antigen receptor that is not introduced into the one or more modifies CBLB alleles.

In some embodiments, the present disclosure provides, in part, a plurality of cells comprising one or more cells contemplated herein.

In various embodiments, the present disclosure provides, in part, a composition comprising one or more cells contemplated herein.

In some embodiments, the present disclosure provides, in part, a composition comprising one or more cells contemplated herein and a physiologically acceptable carrier.

In particular embodiments, the present disclosure provides, in part, a method of editing a human CBLB gene in a cell comprising: introducing a polynucleotide encoding a polypeptide contemplated herein into a cell, wherein expression of the polypeptide creates a double strand break at a target site in a human CBLB gene.

In some embodiments, the present disclosure provides, in part, a method of editing a human CBLB gene in cell comprising: introducing a polynucleotide encoding a polypeptide contemplated herein into the cell, wherein expression of the polypeptide creates a double strand break at a target site in a human CBLB gene, wherein the break is repaired by non-homologous end joining (NHEJ).

In certain embodiments, the present disclosure provides, in part, a method of editing a human CBLB gene in a cell comprising: introducing a polynucleotide encoding a polypeptide contemplated herein and a donor repair template into the cell, wherein expression of the polypeptide creates a double strand break at a target site in a human CBLB gene and the donor repair template is incorporated into the human CBLB gene by homology directed repair (HDR) at the site of the double-strand break (DSB).

In particular embodiments, the cell is a hematopoietic cell.

In certain embodiments, the cell is a T cell.

In certain embodiments, the cell is a CD3+, CD4+, and/or CD8+ cell.

In some embodiments, the cell is an immune effector cell.

In additional embodiments, the cell is a cytotoxic T lymphocytes (CTLs), a tumor infiltrating lymphocytes (TILs), or a helper T cells.

In additional embodiments, the cell is a natural killer (NK) cell or natural killer T (NKT) cell.

In particular embodiments, the source of the cell is peripheral blood mononuclear cells, bone marrow, lymph nodes tissue, cord blood, thymus tissue, tissue from a site of infection, ascites, pleural effusion, spleen tissue, or tumors.

In particular embodiments, the polynucleotide encoding the polypeptide is an mRNA.

In certain embodiments, a polynucleotide encoding a 5'-3' exonuclease is introduced into the cell.

In further embodiments, a polynucleotide encoding Trex2 or a biologically active fragment thereof is introduced into the cell.

In some embodiments, the donor repair template encodes a CBLB gene or portion thereof comprising one or more mutations compared to the wild type CBLB gene.

In particular embodiments, the donor repair template encodes one or more of an immunopotency enhancer, an immunosuppressive signal damper, or an engineered antigen receptor.

In some embodiments, the donor repair template further comprises an RNA polymerase II promoter operably linked to the immunopotency enhancer, immunosuppressive signal damper, or engineered antigen receptor.

In further embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter.

In particular embodiments, the donor repair template further encodes one or more self-cleaving viral peptides operably linked to, interspersed between, and/or flanking the immunopotency enhancer, immunosuppressive signal damper, or engineered antigen receptor.

In additional embodiments, the self-cleaving viral peptide is a 2A peptide.

In certain embodiments, the donor repair template further comprises a heterologous polyadenylation signal.

In further embodiments, the immunosuppressive signal damper comprises an enzymatic function that counteracts an immunosuppressive factor.

In particular embodiments, the immunosuppressive signal damper comprises kynureninase activity.

In some embodiments, the immunosuppressive signal damper comprises: an exodomain that binds an immunosuppressive factor, optionally wherein the exodomain is an antibody or antigen binding fragment thereof; an exodomain that binds an immunosuppressive factor and a transmembrane domain; or an exodomain that binds an immunosuppressive factor, a transmembrane domain, and a modified endodomain that is unable to transduce immunosuppressive signals to the cell.

In certain embodiments, the exodomain and/or transmembrane domain of the immunosuppressive signal damper is the TGFβRII exodomain and/or transmembrane domain.

In some embodiments, the immunopotency enhancer is selected from the group consisting of: a bispecific T cell engager molecule (BiTE), an immunopotentiating factor, and a flip receptor.

In particular embodiments, the immunopotentiating factor is selected from the group consisting of: a cytokine, a chemokine, a cytotoxin, a cytokine receptor, and variants thereof.

In additional embodiments, the flip receptor comprises a TGFβRII exodomain and transmembrane domain; and an endodomain from TLR4, CD28, CD134, CD137, CD278, and/or CD3ζ fused in frame to the C-terminal end of the TGFβRII transmembrane domain.

In particular embodiments, the flip receptor comprises a TGFβRII exodomain; a transmembrane domain isolated from a TLR4, CD3ζ, CD4, CD8a, CD28, CD134, or CD137 polypeptide; and an endodomain from TLR4, CD28, CD134, CD137, CD278, and/or CD3ζ fused in frame to the C-terminal end of the TGFβRII exodomain.

In further embodiments, the flip receptor comprises a TGFβRII exodomain; and a transmembrane domain and endodomain isolated from a TLR4, CD3ζ, CD4, CD8a, CD28, CD134, or CD137 polypeptide fused in frame to the C-terminal end of the TGFβRII exodomain.

In certain embodiments, the engineered antigen receptor is selected from the group consisting of: an engineered TCR, a CAR, a Daric, or a zetakine.

In some embodiments, the donor repair template comprises a 5' homology arm homologous to a human CBLB gene sequence 5' of the DSB and a 3' homology arm homologous to a human CBLB gene sequence 3' of the DSB.

In further embodiments, the lengths of the 5' and 3' homology arms are independently selected from about 100 bp to about 2500 bp.

In particular embodiments, the lengths of the 5' and 3' homology arms are independently selected from about 600 bp to about 1500 bp.

In particular embodiments, the 5'homology arm is about 1500 bp and the 3' homology arm is about 1000 bp.

In some embodiments, the 5'homology arm is about 600 bp and the 3' homology arm is about 600 bp.

In certain embodiments, a viral vector is used to introduce the donor repair template into the cell.

In additional embodiments, the viral vector is a recombinant adeno-associated viral vector (rAAV) or a retrovirus.

In particular embodiments, the rAAV has one or more ITRs from AAV2.

In additional embodiments, the rAAV has a serotype selected from the group consisting of: AAV1, AAV2, AAV3, AAV4, AAV5, AAV6, AAV7, AAV8, AAV9, and AAV10.

In further embodiments, the rAAV has an AAV2 or AAV6 serotype.

In certain embodiments, the retrovirus is a lentivirus.

In some embodiments, the lentivirus is an integrase deficient lentivirus (IDLV).

In various embodiments, the present disclosure provides, in part, a method of treating, preventing, or ameliorating at least one symptom of a cancer, infectious disease, autoimmune disease, inflammatory disease, and immunodeficiency, or condition associated therewith, comprising administering to the subject an effective amount of a composition contemplated herein.

In certain embodiments, the present disclosure provides, in part, a method of treating a solid cancer comprising administering to the subject an effective amount of a composition contemplated herein.

In particular embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In some embodiments, the present disclosure provides, in part, a method of treating a hematological malignancy comprising administering to the subject an effective amount of a composition contemplated herein.

In certain embodiments, the hematological malignancy is a leukemia, lymphoma, or multiple myeloma.

BRIEF DESCRIPTION OF SEVERAL VIEWS OF THE DRAWINGS

FIG. 5 shows an alignment of CBLB HE variants (SEQ ID NOs: 77-83) to the wild-type I-OnuI protein (SEQ ID NO: 1), highlighting non-identical positions.

BRIEF DESCRIPTION OF THE SEQUENCE IDENTIFIERS

Figure 1:
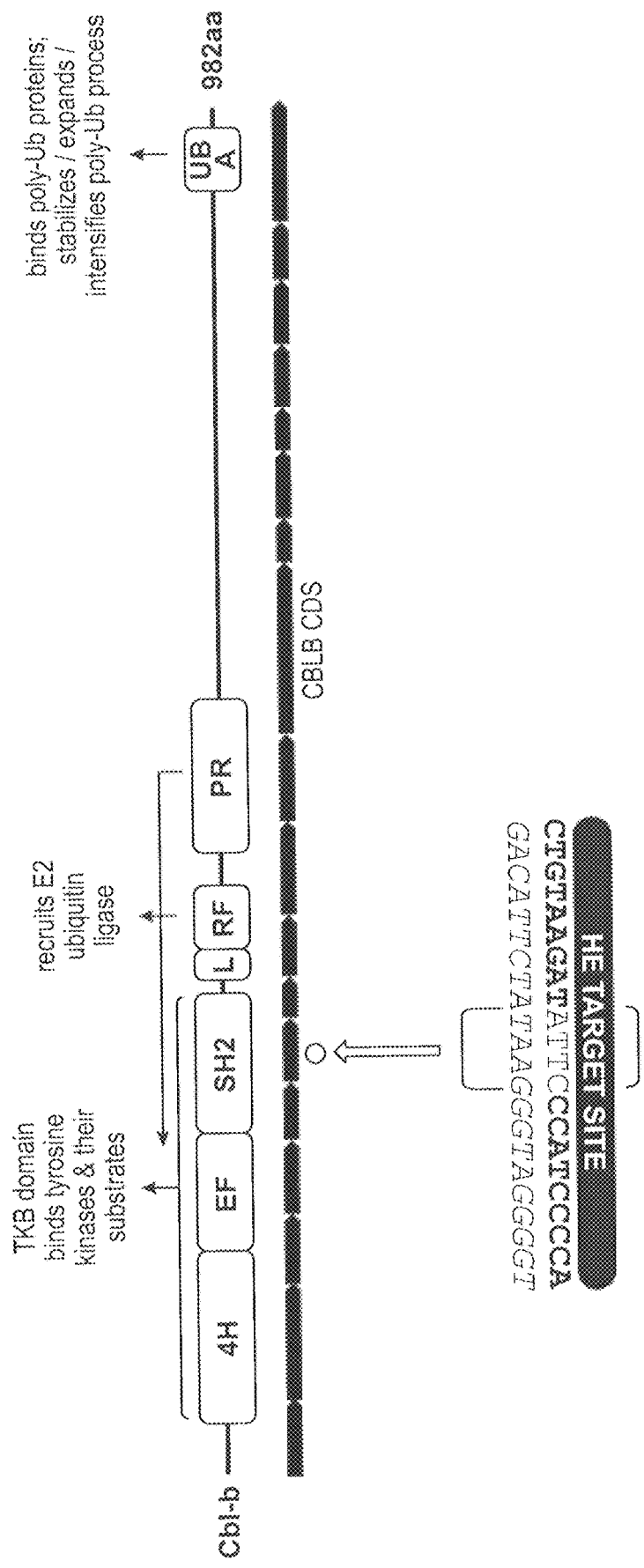
FIG. 1 shows the CBLB gene and the HE target site in exon 6 (SEQ ID NOs: 20 and 76), which encodes the SH2 domain.

SEQ ID NO: 1 is an amino acid sequence of a wild type I-OnuI LAGLIDADG homing endonuclease (LHE).

SEQ ID NO: 2 is an amino acid sequence of a wild type I-OnuI LHE.

SEQ ID NO: 3 is an amino acid sequence of a biologically active fragment of a wild-type I-OnuI LHE.

SEQ ID NO: 4 is an amino acid sequence of a biologically active fragment of a wild-type I-OnuI LHE.

SEQ ID NO: 5 is an amino acid sequence of a biologically active fragment of a wild-type I-OnuI LHE.

SEQ ID NOs: 6-12 set forth amino acid sequences of I-OnuI LHE variants reprogrammed to bind and cleave a target site in the human CBLB gene.

SEQ ID NOs: 13-19 set forth amino acid sequences of I-OnuI LHE variants reprogrammed to bind and cleave a target site in the human CBLB gene.

SEQ ID NO: 20 is an I-OnuI LHE variant target site in exon 6 of a human CBLB gene.

SEQ ID NO: 21 is a TALE DNA binding domain target site in exon 6 of a human CBLB gene.

SEQ ID NO: 22 is a megaTAL target site in exon 6 of a human CBLB gene.

SEQ ID NOs: 23, 25, 27, and 29 set forth I-OnuI LHE variant N-terminal domain target sites in exon 6 of a human CBLB gene.

SEQ ID NOs: 24, 26, and 28 set forth I-OnuI LHE variant C-terminal domain target sites in exon 6 of a human CBLB gene.

SEQ ID NO: 30 is a polynucleotide sequence of a CBLB.E3 surface display plasmid.

SEQ ID NOs: 31-36 set forth-mRNA sequences encoding CBLB megaTALs.

SEQ ID NO: 37 is an mRNA sequence encoding murine Trex2.

SEQ ID NO: 38 is an amino acid sequence encoding murine Trex2.

SEQ ID NOs: 39-49 set forth the amino acid sequences of various linkers.

SEQ ID NOs: 50-74 set forth the amino acid sequences of protease cleavage sites and self-cleaving polypeptide cleavage sites. In the foregoing sequences, X, if present, refers to any amino acid or the absence of an amino acid.

DETAILED DESCRIPTION

A. Overview

The present disclosure generally relates to, in part, improved genome editing compositions and methods of use thereof. Without wishing to be bound by any particular theory, genome editing compositions contemplated in various embodiments can be used to prevent or treat a cancer, infectious disease, autoimmune disease, inflammatory disease, and immunodeficiency, or condition associated therewith, or ameliorate at least one symptom thereof. One limitation or problem that vexes existing adoptive cell therapy is hyporesponsiveness of immune effector cells due to exhaustion mediated by the tumor microenvironment.

Exhausted T cells have a unique molecular signature that is markedly distinct from naive, effector or memory T cells. Exhausted T cells are T cells with decreased cytokine expression and effector function.

Casitas B-lineage (Cbl) lymphoma proto-oncogene B (CBLB) is a member of the RING-finger family or E3 ubiquitin ligases and is expressed in a wide array of tissues and cell types including cells of the hematopoietic lineage. CBLB facilitates the ubiquitination of target substrate proteins via the recruitment of E2-ubiquitin conjugating enzymes to its RING finger domain. Ubiquitination of CBLB substrate proteins may promote protein degradation or interfere with protein-protein interactions. CBLB binds to substrate proteins through its SH2-containing tyrosine kinase binding domain, its proline-rich sequences which interacts with SH3 domain-containing proteins, or its ubiquitin-associated domain which interacts with ubiquitin-tagged proteins.

CBLB is also involved in the negative regulation of effector T cell activity and persistence. CBLB knockout mouse T cells are hyperproliferative, produce heightened levels of IL2 and IFNγ in response to antigen stimulation, are resistant to TGFβ-mediated suppression, and have a lower activation threshold indicating that CBLB plays a role in negatively regulating T cell activation. Without wishing to be bound by any particular theory, it is contemplated that disruption of the CBLB gene in T cells using engineered nucleases will result in more efficacious and persistent adoptive cellular immunotherapies.

In particular embodiments, genome edited immune effector cells contemplated herein are made more resistant to exhaustion by eliminating, decreasing, or damping CBLB expression, CBLB activity, and/or signaling via CBLB.

Genome editing compositions and methods contemplated in various embodiments comprise nuclease variants, designed to bind and cleave a target site in the casitas B-lineage (Cbl) lymphoma proto-oncogene B (CBLB) gene. The nuclease variants contemplated in particular embodiments, can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

In one preferred embodiment, the genome editing compositions contemplated herein comprise a homing endonuclease variant or megaTAL that targets the human CBLB gene.

In one preferred embodiment, the genome editing compositions contemplated herein comprise a homing endonuclease variant or megaTAL and an end-processing enzyme, e.g., Trex2.

In various embodiments, genome edited cells are contemplated. The genome edited cells comprise an edited CBLB gene, wherein the editing strategy is designed to decrease or eliminate CBLB expression. In particular embodiments, CAR T cells, engineered TCR T cells, or DARIC T cell comprise an edited CBLB gene.

In various embodiments, a DNA break is generated in a target site of the CBLB gene in a T cell, e.g., immune effector cell, and NHEJ of the ends of the cleaved genomic sequence may result in a cell with little or no CBLB expression, and preferably a T cell that lacks or substantially lacks functional CBLB expression and/or signaling, e.g., lacks the ability to increase T cell exhaustion. Without wishing to be bound by any particular theory, T cells that lack functional CBLB expression are more resistant to immunosuppression and T cell exhaustion, and thus, are more persistent and therapeutically efficacious.

In various other embodiments, a donor template for repair of the cleaved CBLB genomic sequence is provided. The CBLB gene is repaired with the sequence of the template by homologous recombination at the DNA break-site. In particular embodiments, the repair template comprises a polynucleotide sequence that disrupts, and preferably substantially decreases or eliminates, functional CBLB expression.

In particular embodiments, the CBLB gene is repaired with a polynucleotide encoding an immunopotency enhancer, immunosuppressive signal damper, or engineered antigen receptor.

In particular embodiments, the CBLB gene is repaired with a polynucleotide encoding an immunopotency enhancer, immunosuppressive signal damper, or engineered antigen receptor and is introduced into the CBLB gene so as to adopt the endogenous CBLB promoter to transcriptionally control the expression of the immunopotency enhancer, immunosuppressive signal damper, or engineered antigen receptor.

In preferred embodiments, the genome editing compositions and methods contemplated herein are used to edit the human CBLB gene.

Accordingly, the methods and compositions contemplated herein represent a quantum improvement compared to existing adoptive cell therapies.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); Oligonucleotide Synthesis (N. Gait, Ed., 1984); Nucleic Acid The Hybridization (B. Hames & S. Higgins, Eds., 1985); Transcription and Translation (B. Hames & S. Higgins, Eds., 1984); Animal Cell Culture (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a nuclease variant, genome editing composition, or genome edited cell contemplated herein to produce, elicit, or cause a greater response (i.e., physiological response) compared to the response caused by either vehicle or control. A measurable response may include an increase in catalytic activity, binding affinity, binding site specificity, binding site selectivity, persistence, cytolytic activity, and/or an increase in proinflammatory cytokines, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By "decrease" or "lower" or "lessen" or "reduce" or "abate" or "ablate" or "inhibit" or "dampen" refers generally to the ability of a nuclease variant, genome editing composition, or genome edited cell contemplated herein to produce, elicit, or cause a lesser response (i.e., physiological response) compared to the response caused by either vehicle or control. A measurable response may include a decrease in off-target binding affinity, off-target cleavage specificity, T cell exhaustion, and the like. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By "maintain," or "preserve," or "maintenance," or "no change," or "no substantial change," or "no substantial decrease" refers generally to the ability of a nuclease variant, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined in particular embodiments as an equilibrium dissociation constant ($K_d$) of a particular binding interaction with units of M (e.g., $10^{-5}$ M to $10^{-13}$ M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement. In a preferred embodiment, the target site is a sequence in a human CBLB gene.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may increase the likelihood of imprecise repair.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules.

Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extrachromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

An "immune disorder" refers to a disease that evokes a response from the immune system. In particular embodiments, the term "immune disorder" refers to a cancer, graft-versus-host disease, an autoimmune disease, or an immunodeficiency. In one embodiment, immune disorders encompass infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood).

As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

"Graft-versus-host disease" or "GVHD" refers complications that can occur after cell, tissue, or solid organ transplant. GVHD can occur after a stem cell or bone marrow transplant in which the transplanted donor cells attack the transplant recipient's body. Acute GVHD in humans takes place within about 60 days post-transplantation and results in damage to the skin, liver, and gut by the action of cytolytic lymphocytes. Chronic GVHD occurs later and is a systemic autoimmune disease that affects primarily the skin, resulting in the polyclonal activation of B cells and the hyperproduction of Ig and autoantibodies. Solid-organ transplant graft-versus-host disease (SOT-GVHD) occurs in two forms. The more common type is antibody mediated, wherein antibodies from a donor with blood type O attack a recipient's red blood cells in recipients with blood type A, B, or AB, leading to mild transient, hemolytic anemias. The second form of SOT-GVHD is a cellular type associated with high mortality, wherein donor-derived T cells produce an immunological attack against immunologically disparate host tissue, most often in the skin, liver, gastrointestinal tract, and bone marrow, leading to complications in these organs.

"Graft-versus-leukemia" or "GVL" refer to an immune response to a person's leukemia cells by immune cells present in a donor's transplanted tissue, such as bone marrow or peripheral blood.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Illustrative examples of autoimmune diseases include, but are not limited to: arthritis, inflammatory bowel disease, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance.

Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, Wiskott-Aldrich Syndrome (WAS), and diabetes.

An "infectious disease" refers to a disease that can be transmitted from person to person or from organism to organism, and is caused by a microbial or viral agent (e.g., common cold). Infectious diseases are known in the art and include, for example, hepatitis, sexually transmitted diseases (e.g., *Chlamydia*, gonorrhea), tuberculosis, HIV/AIDS, diphtheria, hepatitis B, hepatitis C, cholera, and influenza.

As used herein, the terms "individual" and "subject" are often used interchangeably and refer to any animal that exhibits a symptom of an immune disorder that can be treated with the nuclease variants, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having an immune disorder.

As used herein, the term "patient" refers to a subject that has been diagnosed with an immune disorder that can be treated with the nuclease variants, genome editing compositions, gene therapy vectors, genome editing vectors, genome edited cells, and methods contemplated elsewhere herein.

As used herein "treatment" or "treating," includes any beneficial or desirable effect on the symptoms or pathology of a disease or pathological condition, and may include even minimal reductions in one or more measurable markers of the disease or condition being treated, e.g., cancer, GVHD, infectious disease, autoimmune disease, inflammatory disease, and immunodeficiency. Treatment can optionally involve delaying of the progression of the disease or condition. "Treatment" does not necessarily indicate complete eradication or cure of the disease or condition, or associated symptoms thereof.

As used herein, "prevent," and similar words such as "prevention," "prevented," "preventing" etc., indicate an approach for preventing, inhibiting, or reducing the likelihood of the occurrence or recurrence of, a disease or condition, e.g., cancer, GVHD, infectious disease, autoimmune disease, inflammatory disease, and immunodeficiency. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated, e.g., cancer, GVHD, infectious disease, autoimmune disease, inflammatory disease, and immunodeficiency. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

As used herein, the term "amount" refers to "an amount effective" or "an effective amount" of a nuclease variant, genome editing composition, or genome edited cell sufficient to achieve a beneficial or desired prophylactic or therapeutic result, including clinical results.

A "prophylactically effective amount" refers to an amount of a nuclease variant, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

C. Nuclease Variants

Nuclease variants contemplated in particular embodiments herein are suitable for genome editing a target site in the CBLB gene and comprise one or more DNA binding domains and one or more DNA cleavage domains (e.g., one or more endonuclease and/or exonuclease domains), and optionally, one or more linkers contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence in a CBLB gene.

In particular embodiments, a nuclease variant binds and cleaves a target sequence in exon 6 of a CBLB gene, preferably at SEQ ID NO: 20 in exon 6 of a CBLB gene, and more preferably at the sequence "ATTC" in SEQ ID NO: 20 in exon 6 of a CBLB gene.

The nuclease variant may be designed and/or modified from a naturally occurring nuclease or from a previous nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerases or template-independent DNA polymerase activity.

Illustrative examples of nuclease variants that bind and cleave a target sequence in the CBLB gene include, but are not limited to homing endonuclease (meganuclease) variants and megaTALs.

1. Homing Endonuclease (Meganuclease) Variants

In various embodiments, a homing endonuclease or meganuclease is reprogrammed to introduce a double-strand break (DSB) in a target site in a CBLB gene. In particular embodiments, a homing endonuclease variant introduces a double strand break in exon 6 of a CBLB gene, preferably at SEQ ID NO: 20 in exon 6 of a CBLB gene, and more preferably at the sequence "ATTC" in SEQ ID NO: 20 in exon 6 of a CBLB gene.

"Homing endonuclease" and "meganuclease" are used interchangeably and refer to naturally-occurring homing endonucleases that recognize 12-45 base-pair cleavage sites and are commonly grouped into five families based on sequence and structure motifs: LAGLIDADG, GIY-YIG, HNH, His-Cys box, and PD-(D/E)XK.

A "reference homing endonuclease" or "reference meganuclease" refers to a wild type homing endonuclease or a homing endonuclease found in nature. In one embodiment, a "reference homing endonuclease" refers to a wild type homing endonuclease that has been modified to increase basal activity.

An "engineered homing endonuclease," "reprogrammed homing endonuclease," "homing endonuclease variant," "engineered meganuclease," "reprogrammed meganuclease," or "meganuclease variant" refers to a homing endonuclease comprising one or more DNA binding domains and one or more DNA cleavage domains, wherein the homing endonuclease has been designed and/or modified from a parental or naturally occurring homing endonuclease, to bind and cleave a DNA target sequence in a CBLB gene. The homing endonuclease variant may be designed and/or modified from a naturally occurring homing endonuclease or from another homing endonuclease variant. Homing endonuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template dependent DNA polymerase or template-independent DNA polymerase activity.

Homing endonuclease (HE) variants do not exist in nature and can be obtained by recombinant DNA technology or by random mutagenesis. HE variants may be obtained by making one or more amino acid alterations, e.g., mutating, substituting, adding, or deleting one or more amino acids, in a naturally occurring HE or HE variant. In particular embodiments, a HE variant comprises one or more amino acid alterations to the DNA recognition interface.

HE variants contemplated in particular embodiments may further comprise one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. In particular embodiments, HE variants are introduced into a T cell with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. The HE variant and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or HE variant. By way of non-limiting example, a HE variant contemplated in particular embodiments may be derived by constructing libraries of HE variants in which one or more amino acid residues localized in the DNA recognition interface of the natural HE (or a previously generated HE variant) are varied. The libraries may be screened for target cleavage activity against each predicted CBLB target site using cleavage assays (see e.g., Jarjour et al., 2009. Nuc. Acids Res. 37(20): 6871-6880).

LAGLIDADG homing endonucleases (LHE) are the most well studied family of homing endonucleases, are primarily encoded in archaea and in organellar DNA in green algae and fungi, and display the highest overall DNA recognition specificity. LHEs comprise one or two LAGLIDADG catalytic motifs per protein chain and function as homodimers or single chain monomers, respectively. Structural studies of LAGLIDADG proteins identified a highly conserved core structure (Stoddard 2005), characterized by an αββαββα fold, with the LAGLIDADG motif belonging to the first helix of this fold. The highly efficient and specific cleavage of LHE's represent a protein scaffold to derive novel, highly specific endonucleases. However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

In one embodiment, LHEs from which reprogrammed LHEs or LHE variants may be designed include, but are not limited to I-CreI and I-SceI.

Illustrative examples of LHEs from which reprogrammed LHEs or LHE variants may be designed include, but are not limited to I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

In one embodiment, the reprogrammed LHE or LHE variant is selected from the group consisting of: an I-CpaMI variant, an I-HjeMI variant, an I-OnuI variant, an I-PanMI variant, and an I-SmaMI variant.

In one embodiment, the reprogrammed LHE or LHE variant is an I-OnuI variant. See e.g., SEQ ID NOs: 6-12.

In one embodiment, reprogrammed I-OnuI LHEs or I-OnuI variants targeting the CBLB gene were generated from a natural I-OnuI or biologically active fragment thereof (SEQ ID NOs: 1-5). In a preferred embodiment, reprogrammed I-OnuI LHEs or I-OnuI variants targeting the human CBLB gene were generated from an existing I-OnuI variant. In one embodiment, reprogrammed I-OnuI LHEs were generated against a human CBLB gene target site set forth in SEQ ID NO: 20.

In a particular embodiment, the reprogrammed I-OnuI LHE or I-OnuI variant that binds and cleaves a human CBLB gene comprises one or more amino acid substitutions in the DNA recognition interface. In particular embodiments, the I-OnuI LHE that binds and cleaves a human CBLB gene comprises at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the DNA recognition interface of I-OnuI (Taekuchi et al. 2011. *Proc Natl Acad Sci U.S.A* 2011 Aug. 9; 108(32): 13077-13082) or an I-OnuI LHE variant as set forth in any one of SEQ ID NOs: 6-12, biologically active fragments thereof, and/or further variants thereof.

In one embodiment, the I-OnuI LHE that binds and cleaves a human CBLB gene comprises at least 70%, more preferably at least 80%, more preferably at least 85%, more preferably at least 90%, more preferably at least 95%, more preferably at least 97%, more preferably at least 99% sequence identity with the DNA recognition interface of I-OnuI (Taekuchi et al. 2011. *Proc Natl Acad Sci U.S.A* 2011 Aug. 9; 108(32): 13077-13082) or an I-OnuI LHE variant as set forth in any one of SEQ ID NOs: 6-12, biologically active fragments thereof, and/or further variants thereof.

In a particular embodiment, an I-OnuI LHE variant that binds and cleaves a human CBLB gene comprises one or more amino acid substitutions or modifications in the DNA recognition interface of an I-OnuI as set forth in any one of SEQ ID NOs: 1-12, biologically active fragments thereof, and/or further variants thereof.

In a particular embodiment, an I-OnuI LHE variant that binds and cleaves a human CBLB gene comprises one or more amino acid substitutions or modifications in the DNA recognition interface, particularly in the subdomains situated from positions 24-50, 68 to 82, 180 to 203 and 223 to 240 of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant comprises one or more amino acid substitutions in the DNA recognition interface at amino acid positions selected from the group consisting of: 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant comprises one or more amino acid substitutions at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-12, biologically active fragments thereof, and/or further variants thereof.

In a particular embodiment, an I-OnuI LHE variant that binds and cleaves a human CBLB gene comprises 5, 10, 15, 20, 25, 30, 35, or 40 or more amino acid substitutions or modifications in the DNA recognition interface, particularly in the subdomains situated from positions 24-50, 68 to 82, 180 to 203 and 223 to 240 of I-OnuI (SEQ ID NOs: 1-5) or an I-OnuI variant as set forth in any one of SEQ ID NOs: 6-12, biologically active fragments thereof, and/or further variants thereof.

In a particular embodiment, an I-OnuI LHE variant that binds and cleaves a human CBLB gene comprises 5, 10, 15, 20, 25, 30, 35, or 40 or more amino acid substitutions or modifications at amino acid positions selected from the group consisting of: 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-12, biologically active fragments thereof, and/or further variants thereof.

In a particular embodiment, an I-OnuI LHE variant that binds and cleaves a human CBLB gene comprises 5, 10, 15, 20, 25, 30, 35, or 40 or more amino acid substitutions or modifications at amino acid positions selected from the group consisting of: 19, 24, 26, 28, 30, 32, 34, 35, 36, 37, 38, 40, 42, 44, 46, 48, 59, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-12, biologically active fragments thereof, and/or further variants thereof.

In one embodiment, an I-OnuI LHE variant that binds and cleaves a human CBLB gene comprises one or more amino acid substitutions or modifications at additional positions situated anywhere within the entire I-OnuI sequence. The residues which may be substituted and/or modified include but are not limited to amino acids that contact the nucleic acid target or that interact with the nucleic acid backbone or with the nucleotide bases, directly or via a water molecule. In one non-limiting example, an I-OnuI LHE variant contemplated herein that binds and cleaves a human CBLB gene comprises one or more substitutions and/or modifications, preferably at least 5, preferably at least 10, preferably at least 15, preferably at least 20, more preferably at least 25, more preferably at least 30, even more preferably at least 35, or even more preferably at least 40 or more amino acid substitutions in at least one position selected from the position group consisting of positions: 24, 26, 28, 30, 32, 34, 35, 36, 37, 38, 40, 42, 44, 46, 48, 68, 70, 72, 78, 80, 92, 116, 138, 143, 159, 168, 178, 180, 182, 184, 186, 188, 189, 190, 191, 192, 193, 195, 197, 199, 201, 203, 207, 223, 225, 227, 232, 236, and 238 of I-OnuI (SEQ ID NOs: 1-5) or an I-OnuI variant as set forth in any one of SEQ ID NOs: 6-12, biologically active fragments thereof, and/or further variants thereof.

In certain embodiments, the HE variant cleaves a CBLB exon 6 target site and comprises at least 5, at least 15, preferably at least 25, more preferably at least 35, or even more preferably at least 40 or more of the following amino acid substitutions: S24C, L26R, L26G, R28D, R28Y, R30H, N32A, N32S, K34D, K34V, S35L, S36R, V37A, V37S, S40R, E42R, G44A, G44S, Q46E, T48V, T48S, V68T, V68K, A70Y, S72A, S78R, K80Q, D92G, V116L, L138M, T143N, S159P, F168L, E178D, C180S, F182V, F182M, N184E, I186K, I186M, S188R, S188N, K189R, S190N, K191P, K191N, L192V, G193K, G193I, Q195G, Q195R, Q197R, V199R, S201G, T203S, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In some embodiments, the HE variant cleaves a CBLB target site and comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44A, Q46E, T48V, V68T, A70Y, S72A, S78R, K80Q, L138M, T143N, F168L, E178D, C180S, F182V, N184E, I186K, S188R, K189R, K191P, L192V, G193K, Q195G, Q197R, V199R, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant cleaves a CBLB target site and comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44A, Q46E, T48V, V68T, A70Y, S72A, S78R, K80Q, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant cleaves a CBLB target site and comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44S, Q46E, T48S, V68T, A70Y, S72A, S78R, K80Q, D92G, V116L, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant cleaves a CBLB target site and comprises at least 5, at least 15, preferably at least 25, more preferably at least 35, or even more preferably at least 40 or more of the following amino acid substitutions: S24C, L26R, R28D, R30H, N32A, K34V, S35L, S36R, V37S, S40R, E42R, G44S, Q46E, T48V, V68T, V68K, A70Y, S72A, S78R, K80Q, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant cleaves a CBLB target site and comprises at least 5, at least 15, preferably at least 25, more preferably at least 35, or even more preferably at least 40 or more of the following amino acid substitutions: S24C, L26G, R28Y, R30H, N32S, K34V, S35L, S36R, V37S, S40R, E42R, G44S, Q46E, T48S, V68T, A70Y, S72A, S78R, K80Q, V116L, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant cleaves a CBLB target site and comprises at least 5, at least 15, preferably at least 25, more preferably at least 35, or even more preferably at least 40 or more of the following amino acid substitutions: S24C, L26R, R28D, R30H, N32A, K34V, S35L, S36R, V37S, S40R, E42R, G44S, Q46E, T48V, V68T, A70Y, S72A, S78R, K80Q, V116L, L138M, T143N, S159P, F168L, E178D, C180S, F182V, N184E, I186K, S188R, K189R, K191P, L192V, G193K, Q195G, Q197R, V199R, S201G, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, the HE variant cleaves a CBLB target site and comprises at least 5, at least 15, preferably at least 25, more preferably at least 35, or even more preferably at least 40 or more of the following amino acid substitutions: S24C, L26R, R28D, N32A, K34D, S35L, S36R, V37A, S40R, E42R, G44A, Q46E, T48V, V68T, A70Y, S72A, S78R, K80Q, D92G, L138M, T143N, S159P, F168L, E178D, C180S, F182M, N184E, I186M, S188N, S190N, K191N, L192V, G193I, Q195R, Q197R, V199R, T203S, K207R, Y223R, K225V, K227N, F232H, D236E, and V238I of I-OnuI (SEQ ID NOs: 1-5) or an I-OnuI variant as set forth in any one of SEQ ID NOs: 6-12, biologically active fragments thereof, and/or further variants thereof.

In particular embodiments, an I-OnuI LHE variant that binds and cleaves a human CBLB gene comprises an amino acid sequence that is at least 80%, preferably at least 85%, more preferably at least 90%, or even more preferably at least 95% identical to the amino acid sequence set forth in any one of SEQ ID NOs: 6-12, or a biologically active fragment thereof.

In particular embodiments, an I-OnuI LHE variant comprises an amino acid sequence set forth in any one of SEQ ID NOs: 6-12, or a biologically active fragment thereof.

In particular embodiments, an I-OnuI LHE variant comprises an amino acid sequence set forth in SEQ ID NO: 6, or a biologically active fragment thereof.

In particular embodiments, an I-OnuI LHE variant comprises an amino acid sequence set forth in SEQ ID NO: 7, or a biologically active fragment thereof.

In particular embodiments, an I-OnuI LHE variant comprises an amino acid sequence set forth in SEQ ID NO: 8, or a biologically active fragment thereof.

In particular embodiments, an I-OnuI LHE variant comprises an amino acid sequence set forth in SEQ ID NO: 9, or a biologically active fragment thereof.

In particular embodiments, an I-OnuI LHE variant comprises an amino acid sequence set forth in SEQ ID NO: 10, or a biologically active fragment thereof.

In particular embodiments, an I-OnuI LHE variant comprises an amino acid sequence set forth in SEQ ID NO: 11, or a biologically active fragment thereof.

In particular embodiments, an I-OnuI LHE variant comprises an amino acid sequence set forth in SEQ ID NO: 12, or a biologically active fragment thereof.

2. megaTALs

In various embodiments, a megaTAL comprising a homing endonuclease variant is reprogrammed to introduce a double-strand break (DSB) in a target site in a CBLB gene. In particular embodiments, a megaTAL introduces a DSB in exon 6 of a CBLB gene, preferably at SEQ ID NO: 20 in exon 6 of a CBLB gene, and more preferably at the sequence "ATTC" in SEQ ID NO: 20 in exon 6 of a CBLB gene.

A "megaTAL" refers to a polypeptide comprising a TALE DNA binding domain and a homing endonuclease variant that binds and cleaves a DNA target sequence in a CBLB gene, and optionally comprises one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase or template-independent DNA polymerase activity.

In particular embodiments, a megaTAL can be introduced into a cell along with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase, or template-independent DNA polymerase activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs, e.g., AvrBs3 from *Xanthomonas campestris* pv. *vesicatoria*, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S* for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-15 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-15.5 repeat units, more preferably 7.5-15.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises a TAL effector architecture comprising an "N-terminal domain (NTD)" polypeptide, one or more TALE repeat domains/units, a "C-terminal domain (CTD)" polypeptide, and a homing endonuclease variant.

In some embodiments, the NTD, TALE repeats, and/or CTD domains are from the same species. In other embodiments, one or more of the NTD, TALE repeats, and/or CTD domains are from different species.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids +1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids +1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a homing endonuclease reprogrammed to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to a homing endonuclease variant. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the homing endonuclease variant. In this way, the megaTALs contemplated herein, increase the specificity and efficiency of genome editing.

In one embodiment, a megaTAL comprises a homing endonuclease variant and a TALE DNA binding domain that binds a nucleotide sequence that is within about 4, 5, or 6 nucleotides, preferably, 5 or 6 nucleotides upstream of the binding site of the reprogrammed homing endonuclease.

In one embodiment, a megaTAL comprises a homing endonuclease variant and a TALE DNA binding domain that binds the nucleotide sequence set forth in SEQ ID NO: 21, which is 5 nucleotides upstream (i.e., there are 4 nucleotides between the TALE binding site and the HE binding site) of the nucleotide sequence bound and cleaved by the homing endonuclease variant (SEQ ID NO: 20). In preferred embodiments, the megaTAL target sequence is SEQ ID NO: 22.

In particular embodiments, a megaTAL contemplated herein, comprises one or more TALE DNA binding repeat units and an LHE variant designed or reprogrammed from an LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD, one or more TALE DNA binding repeat units, a CTD, and an LHE variant selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD, about 9.5 to about 15.5 TALE DNA binding repeat units, and an LHE variant selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an I-OnuI LHE variant. In particular embodiments, any one of, two of, or all of the NTD, DNA binding domain, and CTD can be designed from the same species or different species, in any suitable combination.

In particular embodiments, a megaTAL contemplated herein, comprises the amino acid sequence set forth in any one of SEQ ID NOs: 13-19.

In particular embodiments, a megaTAL-Trex2 fusion protein contemplated herein, comprises the amino acid sequence set forth in any one of SEQ ID NOs: 13-19 and 38.

In certain embodiments, a megaTAL comprises a TALE DNA binding domain and an I-OnuI LHE variant binds and cleaves the nucleotide sequence set forth in SEQ ID NO: 22.

3. End-Processing Enzymes

Genome editing compositions and methods contemplated in particular embodiments comprise editing cellular genomes using a nuclease variant and one or more copies of an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme. In particular embodiments, genome editing compositions comprise a polynucleotide encoding a homing endonuclease variant and an end-processing enzyme in a single fusion polypeptide. In one embodiment, a fusion polypeptide comprises a megaTAL and one or more copies of an end-processing enzyme, each separated by a self-cleaving peptide.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a homing endonuclease variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a homing endonuclease variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, E. coli ExoI, hTREX2, mouse TREX2, rat TREX2, hTREX1, mouse TREX1, and rat TREX1.

In particular embodiments, the DNA end-processing enzyme is a 3' or 5' exonuclease, preferably Trex 1 or Trex2, more preferably Trex2, and even more preferably human or mouse Trex2.

D. Target Sites

Nuclease variants contemplated in particular embodiments can be designed to bind to any suitable target sequence and can have a novel binding specificity, compared to a naturally-occurring nuclease. In particular embodiments, the target site is a regulatory region of a gene including, but not limited to promoters, enhancers, repressor elements, and the like. In particular embodiments, the target site is a coding region of a gene or a splice site. In certain embodiments, nuclease variants are designed to down-regulate or decrease expression of a gene. In particular embodiments, a nuclease variant and donor repair template can be designed to repair or delete a desired target sequence.

In various embodiments, nuclease variants bind to and cleave a target sequence in a human casitas B-lineage (Cbl) lymphoma proto-oncogene B (CBLB) gene. CBL is also referred to as CBL2; Noonan syndrome-like disorder with or without juvenile myelomonocytic leukemia (NSLL); C-CBL; RING finger protein 55 (RNF55); fragile site, folic acid type, rare, fra(11)(q23.3) (FRA11B); E3 ubiquitin-protein ligase CBL; Cas-Br-M (murine) ecotropic retroviral transforming sequence; Cbl proto-oncogene, E3 ubiquitin protein ligase; RING-type E3 ubiquitin transferase CBL; casitas B-lineage lymphoma proto-oncogene; oncogene CBL2; proto-oncogene c-Cbl; and signal transduction protein CBL.

This gene is a proto-oncogene that encodes a RING finger E3 ubiquitin ligase. The encoded protein is one of the enzymes required for targeting substrates for degradation by the proteasome. This protein mediates the transfer of ubiquitin from ubiquitin conjugating enzymes (E2) to specific substrates. This protein also contains an N-terminal phosphotyrosine binding domain that allows it to interact with numerous tyrosine-phosphorylated substrates and target them for proteasome degradation. CBLB functions as a negative regulator of many signal transduction pathways, including T cell activation and persistence.

In particular embodiments, a homing endonuclease variant or megaTAL introduces a double-strand break (DSB) in a target site in a CBLB gene. In particular embodiments, a homing endonuclease variant or megaTAL introduces a DSB in exon 6 of a CBLB gene, preferably at SEQ ID NO: 20 in exon 6 of a CBLB gene, and more preferably at the sequence "ATTC" in SEQ ID NO: 20 in exon 6 of a CBLB gene.

In a preferred embodiment, a homing endonuclease variant or megaTAL cleaves double-stranded DNA and introduces a DSB into the polynucleotide sequence set forth in SEQ ID NO: 20 or 22.

In a preferred embodiment, the CBLB gene is a human CBLB gene.

E. Donor Repair Templates

Nuclease variants may be used to introduce a DSB in a target sequence; the DSB may be repaired through homology directed repair (HDR) mechanisms in the presence of one or more donor repair templates.

In various embodiments, the donor repair template comprises one or more polynucleotides encoding an immunopotency enhancer, an immunosuppressive signal damper, or an engineered antigen receptor.

In various embodiments, it is contemplated that providing a cell an engineered nuclease in the presence of a plurality of donor repair templates independently encoding immunopotency enhancers and/or immunosuppressive signal dampers targeting different immunosuppressive pathways, yields genome edited T cells with increased therapeutic efficacy and persistence. For example, immunopotency enhancers or immunosuppressive signal targeting combinations of PD-1, LAG-3, CTLA-4, TIM3, IL-10R, TIGIT, and TGFβRII pathways may be preferred in particular embodiments.

In particular embodiments, the donor repair template is used to insert a sequence into the genome. In particular preferred embodiments, the donor repair template is used to repair or modify a sequence in the genome.

In various embodiments, a donor repair template is introduced into a hematopoietic cell, e.g., a T cell, by transducing the cell with an adeno-associated virus (AAV), retrovirus, e.g., lentivirus, IDLV, etc., herpes simplex virus, adenovirus, or vaccinia virus vector comprising the donor repair template.

In particular embodiments, the donor repair template comprises one or more homology arms that flank the DSB site.

As used herein, the term "homology arms" refers to a nucleic acid sequence in a donor repair template that is identical, or nearly identical, to DNA sequence flanking the DNA break introduced by the nuclease at a target site. In one embodiment, the donor repair template comprises a 5' homology arm that comprises a nucleic acid sequence that is identical or nearly identical to the DNA sequence 5' of the DNA break site. In one embodiment, the donor repair template comprises a 3' homology arm that comprises a nucleic acid sequence that is identical or nearly identical to the DNA sequence 3' of the DNA break site. In a preferred embodiment, the donor repair template comprises a 5' homology arm and a 3' homology arm. The donor repair template may comprise homology to the genome sequence immediately adjacent to the DSB site, or homology to the genomic sequence within any number of base pairs from the DSB site. In particular embodiments, a pair of homology arms comprises a homology arm comprising a polynucleotide sequence that includes a target site for a double strand break with a mutation in the target site to minimize re-cleavage of the target site. In one embodiment, the donor repair template comprises a nucleic acid sequence that is homologous to a genomic sequence or homology arm of about 5 bp, about 10 bp, about 25 bp, about 50 bp, about 100 bp, about 250 bp, about 500 bp, about 1000 bp, about 2500 bp, about 5000 bp, about 10000 bp or more, including any intervening length of homologous sequence.

Illustrative examples of suitable lengths of homology arms contemplated in particular embodiments, may be independently selected, and include but are not limited to: 5 bp, about 10 bp, about 25 bp, about 50 bp, about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of the 5' and 3' homology arms are independently selected from about 500 bp to about 1500 bp. In one embodiment, the 5'homology arm is about 1500 bp and the 3' homology arm is about 1000 bp. In one embodiment, the 5'homology arm is between about 200 bp to about 600 bp and the 3' homology arm is between about 200 bp to about 600 bp. In one embodiment, the 5'homology arm is about 200 bp and the 3' homology arm is about 200 bp. In one embodiment, the 5'homology arm is about 300 bp and the 3' homology arm is about 300 bp. In one embodiment, the 5'homology arm is about 400 bp and the 3' homology arm is about 400 bp.

In one embodiment, the 5'homology arm is about 500 bp and the 3' homology arm is about 500 bp. In one embodiment, the 5'homology arm is about 600 bp and the 3' homology arm is about 600 bp.

Donor repair templates may comprise one or more expression cassettes in particular embodiments. In certain embodiments, donor repair templates may comprise one or homology arms and one or more polynucleotides including, but not limited to promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, polynucleotides encoding self-cleaving polypeptides, and epitope tags.

In various embodiments, the donor repair template comprises a 5' homology arm, an RNA polymerase II promoter, one or more polynucleotides encoding an immunopotency enhancer, an immunosuppressive signal damper, or an engineered antigen receptor, and a 3' homology arm.

In various embodiments, a target site is modified with a donor repair template comprising a 5' homology arm, one or more polynucleotides encoding self-cleaving viral peptide, e.g., T2A, an immunopotency enhancer, an immunosuppressive signal damper, or an engineered antigen receptor, optionally a poly(A) signal or self-cleaving peptide, and a 3' homology arm, wherein expression of the one or more polynucleotides is governed by the endogenous CBLB promoter.

1. Immunopotency Enhancers

In particular embodiments, the genome edited immune effector cells contemplated herein are made more potent and/or resistant to immunosuppressive factors by introducing a DSB in the CBLB gene in the presence of a donor repair template comprising a polynucleotide encoding an immunopotency enhancer. As used herein, the term "immunopotency enhancer" refers to non-naturally occurring molecules that stimulate and/or potentiate T cell activation and/or function, immunopotentiating factors, and non-naturally occurring polypeptides that convert the immunosuppressive signals from the tumor microenvironment to an immunostimulatory signal in a T cell or other immune cells.

In particular embodiments, the immunopotency enhancer is selected from the group consisting of: a bispecific T cell engager (BiTE) molecule; an immunopotentiating factor including, but not limited to, cytokines, chemokines, cytotoxins, and/or cytokine receptors; and a flip receptor.

In some embodiments, the immunopotency enhancer, immunopotentiating factor, or flip receptor are fusion polypeptides comprising a protein destabilization domain.

a. Bispecific T Cell Engager (BiTE) Molecules

In particular embodiments, the genome edited immune effector cells contemplated herein are made more potent by introducing a DSB in the CBLB gene in the presence of a donor repair template comprising a polynucleotide encoding a bispecific T cell engager (BiTE) molecules. BiTE molecules are bipartite molecules comprising a first binding domain that binds a target antigen, a linker or spacer as contemplated elsewhere herein, and a second binding domain that binds a stimulatory or costimulatory molecule on an immune effector cell. The first and second binding domains may be independently selected from ligands, receptors, antibodies or antigen binding fragments thereof, lectins, and carbohydrates.

In particular embodiments, the first and second binding domains are antigen binding domains.

In particular embodiments, the first and second binding domains are antibodies or antigen binding fragments thereof. In one embodiment, the first and second binding domains are single chain variable fragments (scFv).

Illustrative examples of target antigens that may be recognized and bound by the first binding domain in particular embodiments include, but are not limited to: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

Other illustrative embodiments of target antigens include MHC-peptide complexes, optionally wherein the peptide is processed from: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, GD2, GD3, Glypican-3 (GPC3), MAGE1, NY-ESO-1, IL-11Rα, IL-13Rα2, Lambda, Lewis-Y, Kappa, Mesothelin, Muc1, Muc16, NCAM, NKG2D Ligands, PRAME, PSCA, PSMA, ROR1, SSX, Survivin, TAG72, TEMs, VEGFR2, and WT-1.

Illustrative examples of stimulatory or co-stimulatory molecules on immune effector cells recognized and bound by the second binding domain in particular embodiments include, but are not limited to: CD3γ, CD3δ, CD3ε, CD3ζ, CD28, CD134, CD137, and CD278.

In particular embodiments, a DSB is induced in a CBLB gene by an engineered nuclease, and a donor repair template comprising a polynucleotide encoding a BiTE is introduced into the cell and is inserted into the CBLB gene by homologous recombination.

b. Immunopotentiating Factors

In particular embodiments, the genome edited immune effector cells contemplated herein are made more potent by increasing immunopotentiating factors either in the genome edited cells or cells in the tumor microenvironment. Immunopotentiating factors refer to particular cytokines, chemokines, cytoxins, and cytokine receptors that potentiate the immune response in immune effector cells. In one embodiment, T cells are engineered by introducing a DSB in the CBLB gene in the presence of a donor repair template comprising a polynucleotide encoding a cytokine, chemokine, cytotoxin, or cytokine receptor.

In particular embodiments, the donor repair template comprises a polynucleotide encoding a cytokine selected from the group consisting of: IL-2, insulin, IFN-γ, IL-7, IL-21, IL-10, IL-12, IL-15, and TNF-α.

In particular embodiments, the donor repair template comprises a polynucleotide encoding a chemokine selected from the group consisting of: MIP-1α, MIP-1β, MCP-1, MCP-3, and RANTES.

In particular embodiments, the donor repair template comprises a polynucleotide encoding a cytotoxin selected from the group consisting of: Perforin, Granzyme A, and Granzyme B.

In particular embodiments, the donor repair template comprises a polynucleotide encoding a cytokine receptor selected from the group consisting of: an IL-2 receptor, an IL-7 receptor, an IL-12 receptor, an IL-15 receptor, and an IL-21 receptor.

c. Flip Receptors

In particular embodiments, the genome edited immune effector cells contemplated herein are made more resistant to exhaustion by "flipping" or "reversing" the immunosuppressive signal by immunosuppressive factors elicited by the tumor microenvironment to a positive immunostimulatory signal. In one embodiment, T cells are engineered by introducing a DSB into a CBLB gene in the presence of a donor repair template comprising a polynucleotide encoding a flip receptor. As used herein, the term "flip receptor" refers to a non-naturally occurring polypeptide that converts the immunosuppressive signals from the tumor microenvironment to an immunostimulatory signal in a T cell. In preferred embodiments, a flip receptor refers to a polypeptide that comprises an exodomain that binds an immunosuppressive factor, a transmembrane domain, and an endodomain that transduces an immunostimulatory signal to a T cell.

In one embodiment, the donor repair template encodes a flip receptor comprising an exodomain or extracellular binding domain that binds an immunosuppressive cytokine, a transmembrane domain, and an endodomain of an immunopotentiating cytokine receptor.

In particular embodiments, a flip receptor comprises an exodomain that binds an immunosuppressive cytokine is the extracellular cytokine binding domain of an IL-4 receptor, IL-6 receptor, IL-8 receptor, IL-10 receptor, IL-13 receptor, TGFβ receptor 1, or TGFβ receptor 2; a transmembrane isolated from CD4, CD8a, CD27, CD28, CD134, CD137, CD3ζ, TGFβ receptor 1, TGFβ receptor 2, IL-2 receptor, IL-7 receptor, IL-12 receptor, IL-15 receptor, or IL-21 receptor; and an endodomain isolated from an IL-2 receptor, IL-7 receptor, IL-12 receptor, IL-15 receptor, or IL-21 receptor.

In particular embodiments, a flip receptor comprises an exodomain that binds an immunosuppressive cytokine is an antibody or antigen binding fragment thereof that binds IL-4, IL-6, IL-8, IL-10, IL-13, TGFβ receptor 1, or TGFβ receptor 2; a transmembrane isolated from CD4, CD8a, CD27, CD28, CD134, CD137, a CD3ζ, TGFβ receptor 1, or TGFβ receptor 2, IL-2 receptor, IL-7 receptor, IL-12 receptor, IL-15 receptor, or IL-21 receptor; and an endodomain isolated from an IL-2 receptor, IL-7 receptor, IL-12 receptor, IL-15 receptor, or IL-21 receptor.

In one embodiment, the donor repair template comprises a flip receptor comprising an exodomain that binds an immunosuppressive factor, a transmembrane domain, and one or more intracellular co-stimulatory signaling domains and/or primary signaling domains.

Illustrative examples of exodomains suitable for use in particular embodiments of flip receptors contemplated in particular embodiments include, but are not limited to: an extracellular ligand binding domain of a receptor that comprises an ITIM and/or an ITSM.

Further illustrative examples of exodomains suitable for use in particular embodiments of flip receptors contemplated in particular embodiments include, but are not limited to an extracellular ligand binding domain of: PD-1, LAG-3, TIM-3, CTLA-4, BTLA, CEACAM1, TIGIT, TGFβRI, TGFβRII, IL4R, IL6R, CXCR1, CXCR2, IL10R, IL13Rα2, TRAILR1, RCAS1R, and FAS.

In one embodiment, the exodomain comprises an extracellular ligand binding domain of a receptor selected from the group consisting of: PD-1, LAG-3, TIM-3, CTLA-4, IL10R, TIGIT, TGFβRI, and TGFβRII.

In one embodiment, the donor repair template comprises a flip receptor comprising an exodomain that binds an immunosuppressive cytokine, a transmembrane domain, and one or more intracellular co-stimulatory signaling domains and/or primary signaling domains.

Illustrative examples of transmembrane domains suitable for use in particular embodiments of flip receptors contemplated in particular embodiments include, but are not limited to transmembrane domains of the following proteins: PD-1, LAG-3, TIM-3, CTLA-4, IL1R, TIGIT, TGFβRI and TGFβRII alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, or CD154.

In various embodiments, the flip receptor comprises an endodomain that elicits an immunostimulatory signal. As used herein, the term "endodomain" refers to an immunostimulatory motif or domain, including but not limited to an immunoreceptor tyrosine activation motif (ITAM), a costimulatory signaling domain, a primary signaling domain, or another intracellular domain that is associated with eliciting immunostimulatory signals in T cells.

Illustrative examples of endodomains suitable for use in particular embodiments of flip receptors contemplated in particular embodiments include, but are not limited to domains comprising an ITAM motif.

Additional illustrative examples of endodomains suitable for use in particular embodiments of flip receptors contemplated in particular embodiments include, but are not limited to co-stimulatory signaling domains is isolated from: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, or ZAP70.

Additional illustrative examples of endodomains suitable for use in particular embodiments of flip receptors contemplated in particular embodiments include, but are not limited to: an endodomain isolated from an IL-2 receptor, IL-7 receptor, IL-12 receptor, IL-15 receptor, or IL-21 receptor.

Further illustrative examples of endodomains suitable for use in particular embodiments of flip receptors contemplated in particular embodiments include, but are not limited to primary signaling domains is isolated from: FcRγ, FcRβ, CD3γ, CD3δ, CD3ε, CD3ζ, CD22, CD79a, CD79b, and CD66d.

In particular embodiments, the flip receptor comprises an exodomain that comprises an extracellular domain from PD-1, LAG-3, TIM-3, CTLA-4, IL10R, TIGIT, TGFβRI or TGFβRII: an endodomain isolated from an IL-2 receptor, IL-7 receptor, IL-12 receptor, IL-15 receptor, or IL-21 receptor.

In particular embodiments, the flip receptor comprises an exodomain that comprises an extracellular domain from PD-1, LAG-3, TIM-3, CTLA-4, IL10R, TIGIT, TGFβRI or TGFβRII; a transmembrane domain from a CD3 polypeptide, CD4, CD8α, CD28, CD134, CD137, PD-1, LAG-3, TIM-3, CTLA-4, IL10R, TGFβRI and TGFβRII; and an endodomain from CD28, CD134, CD137, CD278, and/or CD3.

In particular embodiments, the flip receptor comprises an exodomain that comprises an extracellular domain from PD-1, LAG-3, TIM-3, CTLA-4, IL10R, TIGIT, or TGFβRII; a transmembrane domain from a CD3 polypeptide, CD4, CD8α, CD28, CD134, or CD137; and an endodomain from CD28, CD134, CD137, CD278, and/or CD3I.

2. Immunosuppressive Signal Dampers

One limitation or problem that vexes existing adoptive cell therapy is hyporesponsiveness of immune effector cells due to exhaustion mediated by the tumor microenvironment. Exhausted T cells have a unique molecular signature that is markedly distinct from naive, effector or memory T cells. They are defined as T cells with decreased cytokine expression and effector function.

In particular embodiments, genome edited immune effector cells contemplated herein are made more resistant to exhaustion by decreasing or damping signaling by immunosuppressive factors. In one embodiment, T cells are engineered by introducing a DSB in the CBLB gene in the presence of a donor repair template comprising a polynucleotide encoding an immunosuppressive signal damper.

As used herein, the term "immunosuppressive signal damper" refers to a non-naturally occurring polypeptide that decreases the transduction of immunosuppressive signals from the tumor microenvironment to a T cell. In one embodiment, the immunosuppressive signal damper is an antibody or antigen binding fragment thereof that binds an immunosuppressive factor. In preferred embodiments, an immunosuppressive signal damper refers to a polypeptide that elicits a suppressive, dampening, or dominant negative effect on a particular immunosuppressive factor or signaling pathway because the damper comprises and exodomain that binds an immunosuppressive factor, and optionally, a transmembrane domain, and optionally, a modified endodomain (e.g., intracellular signaling domain).

In particular embodiments, the exodomain is an extracellular binding domain that recognizes and binds and immunosuppressive factor.

In particular embodiments, the modified endodomain is mutated to decrease or inhibit immunosuppressive signals. Suitable mutation strategies include, but are not limited to amino acid substitution, addition, or deletion. Suitable mutations further include, but are not limited to endodomain truncation to remove signaling domains, mutating endodomains to remove residues important for signaling motif activity, and mutating endodomains to block receptor cycling. In particular embodiments, the endodomain, when present does not transduce immunosuppressive signals, or has substantially reduced signaling.

Thus, in some embodiments, an immunosuppressive signal damper acts as sink for one or more immunosuppressive factors from the tumor microenvironment and inhibits the corresponding immunosuppressive signaling pathways in the T cell.

One immunosuppressive signal is mediated by tryptophan catabolism. Tryptophan catabolism by indoleamine 2,3-dioxygenase (IDO) in cancer cells leads to the production of kynurenines which have been shown to have an immunosuppressive effect on T cells in the tumor microenvironment. See e.g., Platten et al. (2012) Cancer Res. 72(21):5435-40.

In one embodiment, a donor repair template comprises an enzyme with kynureninase activity.

Illustrative examples of enzymes having kynureninase activity suitable for use in particular embodiments include, but are not limited to, L-Kynurenine hydrolase.

In one embodiment, the donor repair template comprises one or more polynucleotides that encodes an immunosuppressive signal damper that decrease or block immunosuppressive signaling mediated by an immunosuppressive factor.

Illustrative examples of immunosuppressive factors targeted by the immunosuppressive signal dampers contemplated in particular embodiments include, but are not limited to: programmed death ligand 1 (PD-L1), programmed death ligand 2 (PD-L2), transforming growth factor β (TGFβ), macrophage colony-stimulating factor 1 (M-CSF1), tumor necrosis factor related apoptosis inducing ligand (TRAIL), receptor-binding cancer antigen expressed on SiSo cells ligand (RCAS1), Fas ligand (FasL), CD47, interleukin-4 (IL-4), interleukin-6 (IL-6), interleukin-8 (IL-8), interleukin-10 (IL-10), and interleukin-13 (IL-13).

In various embodiments, the immunosuppressive signal damper comprises an antibody or antigen binding fragment thereof that binds an immunosuppressive factor.

In various embodiments, the immunosuppressive signal damper comprises an exodomain that binds an immunosuppressive factor.

In particular embodiments, the immunosuppressive signal damper comprises an exodomain that binds an immunosuppressive factor and a transmembrane domain.

In another embodiment, the immunosuppressive signal damper comprises an exodomain that binds an immunosuppressive factor, a transmembrane domain, and a modified endodomain that does not transduce or that has substantially reduced ability to transduce immunosuppressive signals.

As used herein, the term "exodomain" refers to an antigen binding domain. In one embodiment, the exodomain is an extracellular ligand binding domain of an immunosuppressive receptor that transduces immunosuppressive signals from the tumor microenvironment to a T cell. In particular embodiments, an exodomain refers to an extracellular ligand binding domain of a receptor that comprises an immunoreceptor tyrosine inhibitory motif (ITIM) and/or an immunoreceptor tyrosine switch motif (ITSM).

Illustrative examples of exodomains suitable for use in particular embodiments of immunosuppressive signal dampers include, but are not limited to antibodies or antigen binding fragments thereof, or extracellular ligand binding domains isolated from the following polypeptides: programmed cell death protein 1 (PD-1), lymphocyte activation gene 3 protein (LAG-3), T cell immunoglobulin domain and mucin domain protein 3 (TIM3), cytotoxic T lymphocyte antigen-4 (CTLA-4), band T lymphocyte attenuator (BTLA), T cell immunoglobulin and immunoreceptor tyrosine-based inhibitory motif domain (TIGIT), transforming growth factor β receptor 1 (TGFβRI), transforming growth factor β receptor 2 (TGFβRII), macrophage colony-stimulating factor 1 receptor (CSF1R), interleukin 4 receptor (IL4R), interleukin 6 receptor (IL6R), chemokine (C-X-C motif) receptor 1 (CXCR1), chemokine (C-X-C motif) receptor 2 (CXCR2), interleukin 10 receptor subunit alpha (IL10R), interleukin 13 receptor subunit alpha 2 (IL13Rα2), tumor necrosis factor related apoptosis inducing ligand (TRAILR1), receptor-binding cancer antigen expressed on SiSo cells (RCAS1R), and Fas cell surface death receptor (FAS).

In one embodiment, the exodomain comprises an extracellular ligand binding domain of a receptor selected from the group consisting of: PD-1, LAG-3, TIM3, CTLA-4, IL10R, TIGIT, CSF1R, TGFβRII and TGFβRII.

A number of transmembrane domains may be used in particular embodiments. Illustrative examples of transmembrane domains suitable for use in particular embodiments of immunosuppressive signal dampers contemplated in particular embodiments include, but are not limited to transmembrane domains of the following proteins: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, CD152, CD154, and PD-1.

3. Engineered Antigen Receptors

In particular embodiments, the genome edited immune effector cells contemplated herein comprise an engineered antigen receptor. In one embodiment, T cells comprising a polynucleotide encoding an engineered antigen receptor are edited by introducing a DSB in a CBLB gene. In one embodiment, T cells are engineered by introducing a DSB in a CBLB gene in the presence of a donor repair template comprising a polynucleotide encoding an engineered antigen receptor.

In particular embodiments, the engineered antigen receptor is an engineered T cell receptor (TCR), a chimeric antigen receptor (CAR), a Daric receptor or components thereof, or a chimeric cytokine receptor.

a. Engineered TCRs

In particular embodiments, the genome edited immune effector cells contemplated herein comprise a polynucleotide encoding an engineered TCR. In one embodiment, T cells comprising a polynucleotide encoding an engineered TCR are edited by introducing a DSB in a CBLB gene. In one embodiment, T cells are engineered by introducing a DSB in a CBLB gene in the presence of a donor repair template encoding an engineered TCR. In a particular embodiment, an engineered TCR is inserted at a DSB in a single CBLB allele. Another embodiment, the alpha chain of an engineered TCR is inserted into a DSB in one CBLB allele and the beta chain of the engineered TCR is inserted into a DSB in the other CBLB allele.

In one embodiment, the engineered T cells contemplated herein comprise a polynucleotide encoding an engineered TCR that is not inserted at a CBLB gene and/or one or more of an immunosuppressive signal damper, a flip receptor, an alpha and/or beta chain of an engineered T cell receptor (TCR), a chimeric antigen receptor (CAR), a Daric receptor or components thereof, or a chimeric cytokine receptor is inserted into a DSB in one or more CBLB alleles.

Naturally occurring T cell receptors comprise two subunits, an alpha chain and a beta chain subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing donor repair template comprising a polynucleotide encoding a subunit of a TCR at a DSB in one or more CBLB alleles, wherein the TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the inventive alpha chain or beta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, a donor repair template comprises a polynucleotide encoding an RNA polymerase II promoter or a first self-cleaving viral peptide and a polynucleotide encoding the alpha chain and/or the beta chain of the engineered TCR integrated into one modified and/or non-functional CBLB gene.

In one embodiment, a donor repair template comprises a polynucleotide encoding an RNA polymerase II promoter or a first self-cleaving viral peptide and a polynucleotide encoding the alpha chain and the beta chain of the engineered TCR integrated into one modified and/or non-functional CBLB gene.

In a particular embodiment, the donor repair template comprises from 5' to 3', a polynucleotide encoding a first self-cleaving viral peptide, a polynucleotide encoding the alpha chain of the engineered TCR, a polynucleotide encoding a second self-cleaving viral peptide, and a polynucleotide encoding the beta chain of the engineered TCR integrated into one modified and/or non-functional CBLB gene. In such a case, the other CBLB gene may be functional or may have decreased function or been rendered non-functional by a DSB and repair by NHEJ. In one embodiment, the other CBLB gene has been modified by an engineered nuclease contemplated herein and may have decreased function or been rendered non-functional.

In a certain embodiment, both CBLB genes are modified and have decreased function or are non-functional: the first modified CBLB gene comprises a nucleic acid comprising a polynucleotide encoding a first self-cleaving viral peptide and a polynucleotide encoding the alpha chain of the engineered TCR, and the second modified CBLB gene comprises a polynucleotide encoding a second self-cleaving viral peptide and a polynucleotide encoding the beta chain of the engineered TCR.

b. Chimeric Antigen Receptors (CARs)

In particular embodiments, the engineered immune effector cells contemplated herein comprise one or more chimeric antigen receptors (CARs). In one embodiment, T cells comprising a polynucleotide encoding one or more CARs are edited by introducing a DSB in a CBLB gene. In one embodiment, T cells are engineered by introducing a DSB in one or more CBLB genes in the presence of a donor repair template encoding a CAR. In a particular embodiment, a CAR is inserted at a DSB in a single CBLB gene.

In one embodiment, the engineered T cells contemplated herein a CAR that is not inserted at a CBLB gene and one or more of an immunosuppressive signal damper, a flip receptor, an alpha and/or beta chain of an engineered T cell receptor (TCR), a chimeric antigen receptor (CAR), a Daric receptor or components thereof, or a chimeric cytokine receptor is inserted into a DSB in one or more CBLB genes.

In various embodiments, the genome edited T cells express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In various embodiments, a CAR comprises an extracellular domain that binds to a specific target antigen (also referred to as a binding domain or antigen-specific binding domain), a transmembrane domain and an intracellular signaling domain. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular binding domain that specifically binds to a target polypeptide, e.g., target antigen, expressed on tumor cell. As used herein, the terms, "binding domain," "extracellular domain," "extracellular binding domain," "antigen binding domain," "antigen-specific binding domain," and "extracellular antigen specific binding domain," are used interchangeably and provide a chimeric receptor, e.g., a CAR or Daric, with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the CAR comprises an extracellular domain that binds an antigen selected from the group consisting of: alpha folate receptor, 5T4, $\alpha v\beta 6$ integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In certain embodiments, the CARs comprise linker residues between the various domains. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In particular embodiments, CARs comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1, IgG4, or IgD.

In one embodiment, the binding domain of the CAR is linked to one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8a hinge region.

In one embodiment, the hinge is a PD-1 hinge or CD152 hinge.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a CAR comprises a TM domain derived from CD8α. In another embodiment, a CAR contemplated herein comprises a TM domain derived from CD8a and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In particular embodiments, a CAR comprises an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR comprises an intracellular signaling domain that comprises one or more "costimulatory signaling domains" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more costimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

c. Daric Receptors

In particular embodiments, the engineered immune effector cells comprise one or more Daric receptors. As used herein, the term "Daric receptor" refers to a multi-chain engineered antigen receptor. In one embodiment, T cells comprising a polynucleotide encoding one or more Daric receptor components are edited by introducing a DSB in a CBLB gene. In one embodiment, T cells are engineered by introducing a DSB in one or more CBLB alleles in the presence of a donor repair template encoding one or more components of a Daric. In a particular embodiment, a Daric or one or more components thereof is inserted at a DSB in a single CBLB allele.

In one embodiment, the engineered T cells comprise a Daric that is not inserted at a CBLB gene and one or more of an immunosuppressive signal damper, a flip receptor, an alpha and/or beta chain of an engineered T cell receptor (TCR), a chimeric antigen receptor (CAR), or a Daric receptor or components thereof is inserted into a DSB in one or more CBLB alleles.

Illustrative examples of Daric architectures and components are disclosed in PCT Publication No. WO2015/017214 and U.S. Patent Publication No. 20150266973, each of which is incorporated here by reference in its entirety.

In one embodiment, a donor repair template comprises the following Daric components: a signaling polypeptide comprising a first multimerization domain, a first transmembrane domain, and one or more intracellular co-stimulatory signaling domains and/or primary signaling domains; and a binding polypeptide comprising a binding domain, a second multimerization domain, and optionally a second transmembrane domain. A functional Daric comprises a bridging factor that promotes the formation of a Daric receptor complex on the cell surface with the bridging factor associated with and disposed between the multimerization domains of the signaling polypeptide and the binding polypeptide.

In particular embodiments, the first and second multimerization domains associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, and any combination thereof.

Illustrative examples of rapamycin analogs (rapalogs) include those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an EC50 value in such an in vitro assay that is at least 10 to 250 times larger than the EC50 value observed for rapamycin in the same assay.

Other illustrative examples of rapalogs include, but are not limited to everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT1, or RAFT) from human and other species; yeast proteins including Tor1 and Tor2; and a *Candida* FRAP homolog. Information concerning the nucleotide sequences, cloning, and other aspects of these proteins is already known in the art. For example, a protein sequence accession number for a human mTOR is GenBank Accession No. L34075.1 (Brown et al., Nature 369:756, 1994).

FRB domains suitable for use in particular embodiments contemplated herein generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. An FRB domain for use in Darics contemplated in particular embodiments will be capable of binding to a complex of an FKBP protein bound to rapamycin or a rapalog thereof. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain." Information concerning the nucleotide sequences, cloning, and other aspects of various FKBP species is known in the art (see, e.g., Staendart et al., Nature 346:671, 1990 (human FKBP12); Kay, Biochem. J. 314:361, 1996). Homologous FKBP proteins in other mammalian species, in yeast, and in other organisms are also known in the art and may be used in the fusion proteins disclosed herein. An FKBP domain contemplated in particular embodiments will be capable of binding to rapamycin or a rapalog thereof and participating in a tripartite complex with an FRB-containing protein (as may be determined by any means, direct or indirect, for detecting such binding).

Illustrative examples of FKBP domains suitable for use in a Daric contemplated in particular embodiments include, but are not limited to: a naturally occurring FKBP peptide sequence, preferably isolated from the human FKBP12 protein (GenBank Accession No. AAA58476.1) or a peptide sequence isolated therefrom, from another human FKBP, from a murine or other mammalian FKBP, or from some other animal, yeast or fungal FKBP; a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other illustrative examples of multimerization domain pairs suitable for use in a Daric contemplated in particular embodiments include, but are not limited to include from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In yet other embodiments, an anti-bridging factor blocks the association of a signaling polypeptide and a binding polypeptide with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the Daric components contemplated in particular embodiments and at the same time inhibit or block an unwanted or pathological inflammatory response in a clinical setting.

In one embodiment, the first multimerization domain comprises FRB T2098L, the second multimerization domain comprises FKBP12, and the bridging factor is rapalog AP21967.

In another embodiment, the first multimerization domain comprises FRB, the second multimerization domain comprises FKBP12, and the bridging factor is Rapamycin, temsirolimus or everolimus.

In particular embodiments, a signaling polypeptide a first transmembrane domain and a binding polypeptide comprises a second transmembrane domain or GPI anchor. Illustrative examples of the first and second transmembrane domains are isolated from a polypeptide independently selected from the group consisting of: CD3δ, CD3ζ, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a signaling polypeptide comprises one or more intracellular co-stimulatory signaling domains and/or primary signaling domains.

Illustrative examples of primary signaling domains suitable for use in Daric signaling components contemplated in particular embodiments include those derived from FcRγ, FcRβ, CD3γ, CD3δ, CD3ε, CD3ζ, CD22, CD79a, CD79b, and CD66d. In particular preferred embodiments, a Daric signaling component comprises a CD3ζ primary signaling domain and one or more costimulatory signaling domains. The intracellular primary signaling and costimulatory signaling domains may be linked in any order in tandem to the carboxyl terminus of the transmembrane domain.

Illustrative examples of such costimulatory molecules suitable for use in Daric signaling components contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a Daric signaling component comprises one or more costimulatory signaling domains selected from the group consisting of CD28, CD137, and CD134, and a CD3ζ primary signaling domain.

In particular embodiments, a Daric binding component comprises a binding domain. In one embodiment, the binding domain is an antibody or antigen binding fragment thereof.

The antibody or antigen binding fragment thereof comprises at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the Daric binding component comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, the Daric binding component comprises an extracellular domain, e.g., antibody or antigen binding fragment thereof that binds an MHC-peptide complex, such as a class I MHC-peptide complex or class II MHC-peptide complex.

In particular embodiments, the Daric components contemplated herein comprise a linker or spacer that connects two proteins, polypeptides, peptides, domains, regions, or motifs. In certain embodiments, a linker comprises about two to about 35 amino acids, or about four to about 20 amino acids or about eight to about 15 amino acids or about 15 to about 25 amino acids. In other embodiments, a spacer may have a particular structure, such as an antibody CH2CH3 domain, hinge domain or the like. In one embodiment, a spacer comprises the CH2 and CH3 domains of IgG1, IgG4, or IgD.

In particular embodiments, the Daric components contemplated herein comprise one or more "hinge domains," which plays a role in positioning the domains to enable proper cell/cell contact, antigen binding and activation. A Daric may comprise one or more hinge domains between the binding domain and the multimerization domain and/or the transmembrane domain (TM) or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region. In particular embodiment, the hinge is a CD8α hinge or a CD4 hinge.

In one embodiment, a Daric comprises a signaling polypeptide comprises a first multimerization domain of FRB T2098L, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is rapalog AP21967.

In one embodiment, a Daric comprises a signaling polypeptide comprises a first multimerization domain of FRB, a CD8 transmembrane domain, a 4-1BB costimulatory domain, and a CD3 primary signaling domain; the binding polypeptide comprises an scFv that binds CD19, a second multimerization domain of FKBP12 and a CD4 transmembrane domain; and the bridging factor is Rapamycin, temsirolimus or everolimus.

d. Zetakines

In particular embodiments, the engineered immune effector cells contemplated herein comprise one or more chimeric cytokine receptors. In one embodiment, T cells comprising a polynucleotide encoding a zetakine are edited by introducing a DSB in a CBLB gene. In one embodiment, T cells are engineered by introducing a DSB in one or more CBLB alleles in the presence of a donor repair template encoding a CAR. In a particular embodiment, a chimeric cytokine receptor is inserted at a DSB in a single CBLB allele.

In one embodiment, the engineered T cells contemplated herein a chimeric cytokine receptor that is not inserted at a CBLB gene and one or more of an immunosuppressive signal damper, a flip receptor, an alpha and/or beta chain of an engineered T cell receptor (TCR), a chimeric antigen receptor (CAR), a Daric receptor or components thereof, or a chimeric cytokine receptor is inserted into a DSB in one or more CBLB alleles.

In various embodiments, the genome edited T cells express chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, the chimeric cytokine receptor comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3ε, CD3ζ, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more costimulatory signaling domains selected from the group consisting of CD28, CD137, and CD134, and a CD3ζ primary signaling domain.

F. Polypeptides

Various polypeptides are contemplated herein, including, but not limited to, homing endonuclease variants, megaTALs, and fusion polypeptides. In preferred embodiments, a polypeptide comprises the amino acid sequence set forth in SEQ ID NOs: 1-19 and 38. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Illustrative examples of polypeptides contemplated in particular embodiments include, but are not limited to homing endonuclease variants, megaTALs, BiTEs, cytokines, chemokines, cytotoxins, and cytokine receptors, flip receptors, immunosuppressive signal dampers, CARs, DARICs, TCRs, and zetakines.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a homing endonuclease, megaTAL or the like that binds and cleaves a target site in the human CBLB gene by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

Polypeptide variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

In particular embodiments, a polypeptide comprises a biologically active fragment of a homing endonuclease variant, e.g., SEQ ID NOs: 3-12, or a megaTAL (SEQ ID NOs: 13-19). The biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a homing endonuclease variant compared to a corresponding wild type homing endonuclease sequence, more preferably a deletion of the 4 N-terminal amino acids of a homing endonuclease variant compared to a corresponding wild type homing endonuclease sequence. In a particular embodiment, a biologically active fragment lacks or comprises a deletion of the 1, 2, 3, 4, or 5 C-terminal amino acids of a homing endonuclease variant compared to a corresponding wild type homing endonuclease sequence, more preferably a deletion of the 2 C-terminal amino acids of a homing endonuclease variant compared to a corresponding wild type homing endonuclease sequence. In a particular preferred embodiment, a biologically active fragment lacks or comprises a deletion of the 4 N-terminal amino acids and 2 C-terminal amino acids of a homing endonuclease variant compared to a corresponding wild type homing endonuclease sequence.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1, 2, 3, 4, or 5 C-terminal amino acids: R, G, S, F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1, 2, 3, 4, or 5 C-terminal amino acids: R, G, S, F, V.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (*Natl. Biomed. Res. Found.*, Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | |
|---|---|---|---|---|---|---|
| Alanine | A | Ala | GCA | GCC | GCG | GCU |
| Cysteine | C | Cys | UGC | UGU | | |
| Aspartic acid | D | Asp | GAC | GAU | | |
| Glutamic acid | E | Glu | GAA | GAG | | |
| Phenylalanine | F | Phe | UUC | UUU | | |
| Glycine | G | Gly | GGA | GGC | GGG | GGU |
| Histidine | H | His | CAC | CAU | | |
| Isoleucine | I | Iso | AUA | AUC | AUU | |
| Lysine | K | Lys | AAA | AAG | | |
| Leucine | L | Leu | UUA | UUG | CUA | CUC | CUG | CUU |
| Methionine | M | Met | AUG | | | |
| Asparagine | N | Asn | AAC | AAU | | |
| Proline | P | Pro | CCA | CCC | CCG | CCU |
| Glutamine | Q | Gln | CAA | CAG | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU |
| Valine | V | Val | GUA | GUC | GUG | GUU |
| Tryptophan | W | Trp | UGG | | | |
| Tyrosine | Y | Tyr | UAC | UAU | | |

Guidance in determining which amino acid residues can be substituted, inserted, or deleted without abolishing biological activity can be found using computer programs well known in the art, such as DNASTAR, GCG, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers $(G)_n$; glycine-serine polymers $(G_{1-5}S_{1-5})_n$, where n is an integer of at least one, two, three, four, or five; glycine-alanine polymers; alanine-serine polymers; GGG (SEQ ID NO: 39); DGGGS (SEQ ID NO: 40); TGEKP (SEQ ID NO: 41) (see e.g., Liu et al., *PNAS* 5525-5530 (1997)); GGRR (SEQ ID NO: 42) (Pomerantz et al. 1995, supra); $(GGGGS)_n$ wherein n=1, 2, 3, 4 or 5 (SEQ ID NO: 43) (Kim et al., PNAS 93, 1156-1160 (1996); EGKSSGSGSESKVD (SEQ ID NO: 44) (Chaudhary et al., 1990, *Proc. Natl. Acad. Sci. U.S.A.* 87:1066-1070); KESGSVSSEQLAQFRSLD (SEQ ID NO: 45) (Bird et al., 1988, Science 242:423-426), GGRRGGGS (SEQ ID NO: 46); LRQRDGERP (SEQ ID NO: 47); LRQKDGGGSERP (SEQ ID NO: 48); LRQKD $(GGGS)_2$ERP (SEQ ID NO: 49). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) *Nature Biotech.* 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3 C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 50), for example, ENLYFQG (SEQ ID NO: 51) and ENLYFQS (SEQ ID NO: 52), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

TABLE 2

Exemplary 2A sites include the following sequences:

| | |
|---|---|
| SEQ ID NO: 53 | GSGATNFSLLKQAGDVEENPGP |
| SEQ ID NO: 54 | ATNFSLLKQAGDVEENPGP |
| SEQ ID NO: 55 | LLKQAGDVEENPGP |
| SEQ ID NO: 56 | GSGEGRGSLLTCGDVEENPGP |
| SEQ ID NO: 57 | EGRGSLLTCGDVEENPGP |
| SEQ ID NO: 58 | LLTCGDVEENPGP |
| SEQ ID NO: 59 | GSGQCTNYALLKLAGDVESNPGP |
| SEQ ID NO: 60 | QCTNYALLKLAGDVESNPGP |
| SEQ ID NO: 61 | LLKLAGDVESNPGP |
| SEQ ID NO: 62 | GSGVKQTLNFDLLKLAGDVESNPGP |
| SEQ ID NO: 63 | VKQTLNFDLLKLAGDVESNPGP |
| SEQ ID NO: 64 | LLKLAGDVESNPGP |
| SEQ ID NO: 65 | LLNFDLLKLAGDVESNPGP |
| SEQ ID NO: 66 | TLNFDLLKLAGDVESNPGP |
| SEQ ID NO: 67 | LLKLAGDVESNPGP |
| SEQ ID NO: 68 | NFDLLKLAGDVESNPGP |
| SEQ ID NO: 69 | QLLNFDLLKLAGDVESNPGP |
| SEQ ID NO: 70 | APVKQTLNFDLLKLAGDVESNPGP |

TABLE 2-continued

Exemplary 2A sites include the following sequences:

| | |
|---|---|
| SEQ ID NO: 71 | VTELLYRMKRAETYCPRPLLAIHPTEARHKQKIVAPVKQT |
| SEQ ID NO: 72 | LNFDLLKLAGDVESNPGP |
| SEQ ID NO: 73 | LLAIHPTEARHKQKIVAPVKQTLNFDLLKLAGDVESNPGP |
| SEQ ID NO: 74 | EARHKQKIVAPVKQTLNFDLLKLAGDVESNPGP |

G. Polynucleotides

In particular embodiments, polynucleotides encoding one or more homing endonuclease variants, megaTALs, end-processing enzymes, and fusion polypeptides or one or more biologically active fragments or variants contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. In particular embodiments, a polynucleotides is a polynucleotide fragments that encodes one or more biologically active polypeptide fragments or variants. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include, but are not limited to polynucleotides encoding SEQ ID NOs: 1-19 and 38, and polynucleotide sequences set forth in SEQ ID NOs: 20-37.

In various illustrative embodiments, polynucleotides contemplated herein include, but are not limited to polynucleotides encoding homing endonuclease variants, megaTALs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

Polynucleotide variants include polynucleotide fragments that encode biologically active polypeptide fragments or variants. As used herein, the term "polynucleotide fragment" refers to a polynucleotide fragment at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more nucleotides in length that encodes a polypeptide variant that retains at least 100%, at least 90%, at least 80%, at least 70%, at least 60%, at least 50%, at least 40%, at least 30%, at least 20%, at least 10%, or at least 5% of the naturally occurring polypeptide activity. Polynucleotide fragments refer to a polynucleotide that encodes a polypeptide that has an amino-terminal deletion, a carboxyl-terminal deletion, and/or an internal deletion or substitution of one or more amino acids of a naturally-occurring or recombinantly-produced polypeptide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in for example, DNASTAR, GCG, DNA Strider, Geneious, Mac Vector, or Vector NTI software) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man.

In various embodiments, a polynucleotide comprises an mRNA encoding a polypeptide contemplated herein including, but not limited to, a homing endonuclease variant, a megaTAL, and an end-processing enzyme. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, a mRNA contemplated herein comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5')ppp(5')G, G(5')ppp(5')C, G(5')ppp(5')A; methylated 5' cap analogs, e.g., m$^7$G(5')ppp(5')G, m$^7$G(5')ppp(5')C, and m$^7$G(5')ppp(5')A; dimethylated 5' cap analogs, e.g., m$^{2,7}$G(5')ppp(5')G, m$^{2,7}$G(5')ppp(5')C, and m$^{2,7}$G(5')ppp(5')A; trimethylated 5' cap analogs, e.g., m$^{2,2,7}$G(5')ppp(5')G, m$^{2,2,7}$G(5')ppp(5')C, and m$^{2,2,7}$G(5')ppp(5')A; dimethylated symmetrical 5' cap analogs, e.g., m$^7$G(5')pppm$^7$(5')G, m$^7$G(5')pppm$^7$(5')C, and m$^7$G(5')pppm$^7$(5')A; and anti-reverse 5' cap analogs, e.g, Anti-Reverse Cap Analog (ARCA) cap, designated 3'O-Me-m$^7$G(5')ppp(5')G, 2'O-Me-m$^7$G(5')ppp(5')G, 2'O-Me-m$^7$G(5')ppp(5')C, 2'O-Me-m$^7$G(5')ppp(5')A, m$^7$2'd(5')ppp(5')G, m$^7$2'd(5')ppp(5')C, m$^7$2'd(5')ppp(5')A, 3'O-Me-m$^7$G(5')ppp(5')C, 3'O-Me-m$^7$G(5')ppp(5')A, m$^7$3'd(5')ppp(5')G, m$^7$3'd(5')ppp(5')C, m$^7$3'd(5')ppp(5')A and their tetraphosphate derivatives) (see, e.g., Jemiety et al., RNA, 9: 1108-1122 (2003)).

In particular embodiments, mRNAs comprise a 5' cap that is a 7-methyl guanylate ("m$^7$G") linked via a triphosphate bridge to the 5'-end of the first transcribed nucleotide, resulting in m$^7$G(5')ppp(5')N, where N is any nucleoside.

In some embodiments, mRNAs comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m$^7$G(5')ppp(5')G cap.

In one embodiment, an mRNA comprises an ARCA cap.

In particular embodiments, an mRNA contemplated herein comprises one or more modified nucleosides.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA comprises one or more modified nucleosides selected from the group consisting of: 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA comprises one or more modified nucleosides selected from the group consisting of: 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA comprises one or more modified nucleosides selected from the group consisting of: inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acid bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, in some embodiments, the cassette has its 3' and 5' ends adapted for ready insertion into a vector and/or genome, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide-of-interest comprises a donor repair template.

In a certain embodiment, a polynucleotide-of-interest comprises an inhibitory polynucleotide including, but not limited to, an siRNA, an miRNA, an shRNA, a ribozyme or another inhibitory RNA.

In one embodiment, a donor repair template comprising an inhibitory RNA comprises one or more regulatory sequences, such as, for example, a strong constitutive pol III, e.g., human or mouse U6 snRNA promoter, the human and mouse H1 RNA promoter, or the human tRNA-val promoter, or a strong constitutive pol II promoter, as described elsewhere herein.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1a-short) promoter, a long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., *J Virol.* 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc.

Conditional expression can also be achieved by using a site specific DNA recombinase. According to certain embodiments, polynucleotides comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s)

required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (Sauer, B., Current Opinion in Biotechnology 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), F1, F2, F3 (Schlake and Bode, 1994), F4, F5 (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

In one embodiment, a polynucleotide contemplated herein comprises a donor repair template polynucleotide flanked by a pair of recombinase recognition sites. In particular embodiments, the repair template polynucleotide is flanked by LoxP sites, FRT sites, or att sites.

In particular embodiments, polynucleotides contemplated herein, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. *Mol Cell Biol* 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO:75), where R is a purine (A or G) (Kozak, 1986. Cell. 44(2):283-92, and Kozak, 1987. *Nucleic Acids Res.* 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the genetically modified cells contemplated herein to be susceptible to negative selection in vivo. "Negative selection" refers to an infused cell that can be eliminated as a result of a change in the in vivo condition of the individual. The negative selectable phenotype may result from the insertion of a gene that confers sensitivity to an administered agent, for example, a compound. Negative selection genes are known in the art, and include, but are not limited to: the Herpes simplex virus type I thymidine kinase (HSV-I TK) gene which confers ganciclovir sensitivity; the cellular hypoxanthine phosphribosyltransferase (HPRT) gene, the cellular adenine phosphoribosyltransferase (APRT) gene, and bacterial cytosine deaminase.

In some embodiments, genetically modified cells comprise a polynucleotide further comprising a positive marker that enables the selection of cells of the negative selectable phenotype in vitro. The positive selectable marker may be a gene, which upon being introduced into the host cell, expresses a dominant phenotype permitting positive selection of cells carrying the gene. Genes of this type are known in the art, and include, but are not limited to hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides encoding one or more nuclease variants, megaTALs, end-processing enzymes, or fusion polypeptides may be introduced into hematopoietic cells, e.g., T cells, by both non-viral and viral methods. In particular embodiments, delivery of one or more polynucleotides encoding nucleases and/or donor repair templates may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising nuclease variants and/or donor repair templates are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated herein include, but are not limited to adeno-associated virus (AAV), retrovirus, herpes simplex virus, adenovirus, and vaccinia virus vectors.

In various embodiments, one or more polynucleotides encoding a nuclease variant and/or donor repair template are introduced into a hematopoietic cell, e.g., a T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding a nuclease variant and/or donor repair template are introduced into a hematopoietic cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D1161, D116A, E152G, or E152A mutation; D64V, D1161, and E152G mutations; or D64V, D116A, and E152A mutations.

In one embodiment, the HIV-1 integrase deficient pol gene comprises a D64V mutation.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173. In another embodiment, a lentiviral vector contains a FLAP element with one or more mutations in the cPPT and/or CTS elements. In yet another embodiment, a lentiviral vector comprises either a cPPT or CTS element. In yet another embodiment, a lentiviral vector does not comprise a cPPT or CTS element.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol*. 65: 1053; and Cullen et al., 1991. Cell 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., in which the right (3') LTR enhancer-promoter region, known as the U3 region, has been modified (e.g., by deletion or substitution) to prevent viral transcription beyond the first round of viral replication. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4$^+$ presenting cells.

In certain embodiments, lentiviral vectors are produced according to known methods. See e.g., Kutner et al., *BMC Biotechnol.* 2009; 9: 10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides encoding a nuclease variant and/or donor repair template are introduced into a hematopoietic cell by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides encoding nuclease variant and/or donor repair template are introduced into a hematopoietic cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

H. Genome Edited Cells

The genome edited cells manufactured by the methods contemplated in particular embodiments comprise one or more gene edits in a CBLB gene and provide improved cell-based therapeutics for the prevention, treatment, or amelioration of at least one symptom, of a cancer, GVHD, infectious disease, autoimmune disease, immunodeficiency or condition associated therewith. Without wishing to be bound by any particular theory, it is believed that the compositions and methods contemplated herein increase the efficacy of adoptive cell therapies, in part, by making the therapeutic cells more persistent and more resistant to immunosuppressive signals and exhaustion.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

As used herein, the term "population of cells" refers to a plurality of cells that may be made up of any number and/or combination of homogenous or heterogeneous cell types, as described elsewhere herein. For example, for transduction of T cells, a population of cells may be isolated or obtained from peripheral blood. A population of cells may comprise about 10%, about 20%, about 30%, about 40%, about 50%, about 60%, about 70%, about 80%, about 90%, or about 100% of the target cell type to be edited. In certain embodiments, T cells may be isolated or purified from a population of heterogeneous cells using methods known in the art.

Illustrative examples of cell types whose genome can be edited using the compositions and methods contemplated herein include, but are not limited to, cell lines, primary cells, stem cells, progenitor cells, and differentiated cells, and mixtures thereof.

In a preferred embodiment, the genome editing compositions and methods are used to edit hematopoietic cells, more preferably immune cells, and even more preferably T cells.

The terms "T cell" or "T lymphocyte" are art-recognized and are intended to include thymocytes, immune effector cells, regulatory T cells, naïve T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), a tumor infiltrating cytotoxic T cell (TIL; $CD8^+$ T cell), $CD4^+CD8^+$ T cell, $CD4^-CD8^-$ T cell, or any other subset of T cells. In one embodiment, the T cell is an immune effector cell. In one embodiment, the T cell is an NKT cell. Other illustrative populations of T cells suitable for use in particular embodiments include naïve T cells and memory T cells.

In various embodiments, genome edited cells comprise immune effector cells comprising a CBLB gene edited by the compositions and methods contemplated herein. An "immune effector cell," is any cell of the immune system that has one or more effector functions (e.g., cytotoxic cell killing activity, secretion of cytokines, induction of ADCC and/or CDC). Illustrative immune effector cells contemplated in particular embodiments are T lymphocytes, in particular cytotoxic T cells (CTLs; $CD8^+$ T cells), TILs, and helper T cells (HTLs; $CD4^+$ T cells). In one embodiment, immune effector cells comprise T cells. In one embodiment, immune effector cells comprise natural killer (NK) cells. In one embodiment, immune effector cells comprise natural killer T (NKT) cells.

"Potent T cells," and "young T cells," are used interchangeably in particular embodiments and refer to T cell phenotypes wherein the T cell is capable of proliferation and a concomitant decrease in differentiation. In particular embodiments, the young T cell has the phenotype of a "naïve T cell." In particular embodiments, young T cells comprise one or more of, or all of the following biological markers: CD62L, CCR7, CD28, CD27, CD122, CD127, CD197, and CD38. In one embodiment, young T cells comprise one or more of, or all of the following biological markers: CD62L, CD127, CD197, and CD38. In one embodiment, the young T cells lack expression of CD57, CD244, CD160, PD-1, CTLA4, PD-1, and LAG3.

T cells can be obtained from a number of sources including, but not limited to, peripheral blood mononuclear cells, bone marrow, lymph nodes tissue, cord blood, thymus tissue, tissue from a site of infection, ascites, pleural effusion, spleen tissue, and tumors.

In particular embodiments, a population of cells comprising immune effector cells or T cells comprises an edited CBLB gene, wherein the edit is a DSB repaired by NHEJ. In particular embodiments, an immune effector cell or T cell comprises an edited CBLB gene, wherein the edit is a DSB repaired by NHEJ. In particular embodiments, the edit is an insertion or deletion (INDEL) of about 1, 2, 3, 4, 5, 6, 7, 8, 9, 10, 11, 12, 13, 14 15, 16, 17, 18, 19, 20, 21, 22, 23, 24, 25 or more nucleotides in a coding sequence of the CBLB gene, preferably in exon 6 of the CBLB gene, more preferably at SEQ ID NO: 20 (or SEQ ID NO: 22) in exon 6 of the CBLB gene.

In particular embodiments, a population of cells comprising immune effector cells or T cells comprises an edited CBLB gene comprising a donor repair template incorporated at a DSB repaired by HDR.

In particular embodiments, a population of cells comprising immune effector cells or T cells comprises an edited CBLB gene comprising a donor repair template comprising a CBLB gene or portion thereof and is designed to introduce one or more mutations in a genomic CBLB sequence to modify CBLB expression activity, or signaling, and preferably, to decrease or eliminate CBLB expression, activity, and/or signaling.

In various embodiments, a genome edited cell comprises an edit in the CBLB gene and further comprises a polynucleotide encoding a flip receptor, a bispecific T cell engager (BiTE) molecule; a cytokine (e.g., IL-2, insulin, IFN-γ, IL-7, IL-21, IL-10, IL-12, IL-15, and TNF-α), a chemokine (e.g., MIP-1α, MIP-1β, MCP-1, MCP-3, and RANTES), a cytotoxin (e.g., Perforin, Granzyme A, and Granzyme B), a cytokine receptor (e.g., an IL-2 receptor, an IL-7 receptor, an IL-12 receptor, an IL-15 receptor, and an IL-21 receptor), or an engineered antigen receptor (e.g., an engineered T cell receptor (TCR), a chimeric antigen receptor (CAR), a Daric receptor or components thereof, or a chimeric cytokine receptor). In one embodiment, a donor repair template comprising the polynucleotide and a nuclease variant are introduced into the cell and the polynucleotide is incorporated into the cell's genome at the DSB site in the CBLB gene by HDR repair. The polynucleotide may also be introduced into the cell at a site other than the CBLB gene, e.g., by transducing the cell with a vector comprising the polynucleotide.

I. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in the human CBLB gene in a cell or a population of cells. In preferred embodiments, a genome editing composition is used to edit a CBLB gene in a hematopoietic cell, e.g., a T cell or an immune effector cell.

In various embodiments, the compositions contemplated herein comprise a nuclease variant, and optionally an end-processing enzyme, e.g., a 3'-5' exonuclease (Trex2). The nuclease variant may be in the form of an mRNA that is introduced into a cell via polynucleotide delivery methods disclosed supra, e.g., electroporation, lipid nanoparticles, etc. In one embodiment, a composition comprising an mRNA encoding a homing endonuclease variant or megaTAL, and optionally a 3'-5' exonuclease, is introduced in a cell via polynucleotide delivery methods disclosed supra. The composition may be used to generate a genome edited cell or population of genome edited cells by error prone NHEJ.

In various embodiments, the compositions contemplated herein comprise a donor repair template. The composition may be delivered to a cell that expresses or will express nuclease variant, and optionally an end-processing enzyme. In one embodiment, the composition may be delivered to a cell that expresses or will express a homing endonuclease variant or megaTAL, and optionally a 3'-5' exonuclease. Expression of the gene editing enzymes in the presence of the donor repair template can be used to generate a genome edited cell or population of genome edited cells by HDR.

In particular embodiments, the compositions contemplated herein comprise a population of cells, a nuclease variant, and optionally, a donor repair template. In particular embodiments, the compositions contemplated herein comprise a population of cells, a nuclease variant, an end-processing enzyme, and optionally, a donor repair template. The nuclease variant and/or end-processing enzyme may be in the form of an mRNA that is introduced into the cell via polynucleotide delivery methods disclosed supra.

In particular embodiments, the compositions contemplated herein comprise a population of cells, a homing endonuclease variant or megaTAL, and optionally, a donor repair template. In particular embodiments, the compositions contemplated herein comprise a population of cells, a homing endonuclease variant or megaTAL, a 3'-5' exonuclease, and optionally, a donor repair template. The homing endonuclease variant, megaTAL, and/or 3'-5' exonuclease may be in the form of an mRNA that is introduced into the cell via polynucleotide delivery methods disclosed supra., e.g., electroporation.

In particular embodiments, the population of cells comprise genetically modified immune effector cells.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising genome edited T cells are formulated in PlasmaLyte.

In various embodiments, compositions comprising genome edited T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. $22^{nd}$ Edition. Edited by Loyd V. Allen Jr. Philadelphia, Pa.: Pharmaceutical Press; 2012, which is incorporated by reference herein, in its entirety.

J. Genome Edited Cell Therapies

Cells comprising an edited CBLB gene that are manufactured by the compositions and methods contemplated herein provide improved drug products for use in the prevention, treatment, or amelioration of at least one symptom of a cancer, GVHD, an infectious disease, an autoimmune disease, an inflammatory disease, or an immunodeficiency. As used herein, the term "drug product" refers to genetically modified cells produced using the compositions and methods contemplated herein. In particular embodiments, the drug product comprises genetically edited immune effector cells or T cells. In preferred embodiments, the drug product comprises genetically edited immune effector cells or T cells that express an engineered TCR or CAR or other engineered antigen receptor. Moreover, the genome edited T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of genome edited immune effector cells or T cells comprising an edited CBLB gene are administered to a subject to prevent, treat, or ameliorate at least one symptom of a cancer, GVHD, an infectious disease, an autoimmune disease, an inflammatory disease, or an immunodeficiency.

In particular embodiments, the CBLB edited cells do not substantially express, or lack expression of, CBLB and therefore lack or substantially lack functional CBLB expression and/or activity, e.g., lack the ability to increase T cell exhaustion and to inhibit expression of proinflammatory cytokines. In particular embodiments, genome edited immune effector cells that lack CBLB are more resistant to immunosuppressive signals from the tumor microenvironment and display increased persistence and resistance to T cell exhaustion.

In particular embodiments, a method of preventing, treating, or ameliorating at least one symptom of a cancer comprises administering the subject an effective amount of genome edited immune effector cells or T cells comprising an edited CBLB gene and an engineered TCR, CAR, or Daric, or other therapeutic transgene to redirect the cells to a tumor or cancer. The genetically modified cells are a more durable and persistent drug product because the cells are more resistant to immunosuppressive signals from the tumor microenvironment by virtue of editing the CBLB gene to decrease or eliminate CBLB expression.

In particular embodiments, genome edited cells contemplated herein are used in the treatment of solid tumors or cancers.

In particular embodiments, genome edited cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, genome edited cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, genome edited cells contemplated herein are used in the treatment of various cancers including but not limited to pancreatic, bladder, and lung.

In particular embodiments, genome edited cells contemplated herein are used in the treatment of liquid cancers or hematological cancers.

In particular embodiments, genome edited cells contemplated herein are used in the treatment of B-cell malignancies, including but not limited to: leukemias, lymphomas, and multiple myeloma.

In particular embodiments, genome edited cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sezary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

Preferred cells for use in the genome editing methods contemplated herein include autologous/autogeneic ("self") cells, preferably hematopoietic cells, more preferably T cells, and more preferably immune effector cells. In one embodiment, the cells are Treg cells.

In particular embodiments, methods comprising administering a therapeutically effective amount of genome edited cells contemplated herein or a composition comprising the same, to a patient in need thereof, alone or in combination with one or more therapeutic agents, are provided. In certain embodiments, the cells are used in the treatment of patients at risk for developing a cancer, GVHD, an infectious disease, an autoimmune disease, an inflammatory disease, or an immunodeficiency. Thus, particular embodiments comprise the treatment or prevention or amelioration of at least one symptom of a cancer, an infectious disease, an autoimmune disease, an inflammatory disease, or an immunodeficiency comprising administering to a subject in need thereof, a therapeutically effective amount of the genome edited cells contemplated herein.

In one embodiment, a method of treating a cancer, GVHD, an infectious disease, an autoimmune disease, an inflammatory disease, or an immunodeficiency in a subject in need thereof comprises administering an effective amount, e.g., therapeutically effective amount of a composition comprising genome edited cells contemplated herein. The quantity and frequency of administration will be determined by such factors as the condition of the patient, and the type and severity of the patient's disease, although appropriate dosages may be determined by clinical trials.

In one illustrative embodiment, the effective amount of genome edited cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of genome edited cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of genome edited cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

The administration of the compositions contemplated in particular embodiments may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a method of treating a subject diagnosed with a cancer, comprises removing immune effector cells from the subject, editing the genome of said immune effector cells and producing a population of genome edited immune effector cells, and administering the population of genome edited immune effector cells to the same subject. In a preferred embodiment, the immune effector cells comprise T cells.

The methods for administering the cell compositions contemplated in particular embodiments include any method which is effective to result in reintroduction of ex vivo genome edited immune effector cells or on reintroduction of the genome edited progenitors of immune effector cells that on introduction into a subject differentiate into mature immune effector cells. One method comprises genome editing peripheral blood T cells ex vivo and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Figure 2:
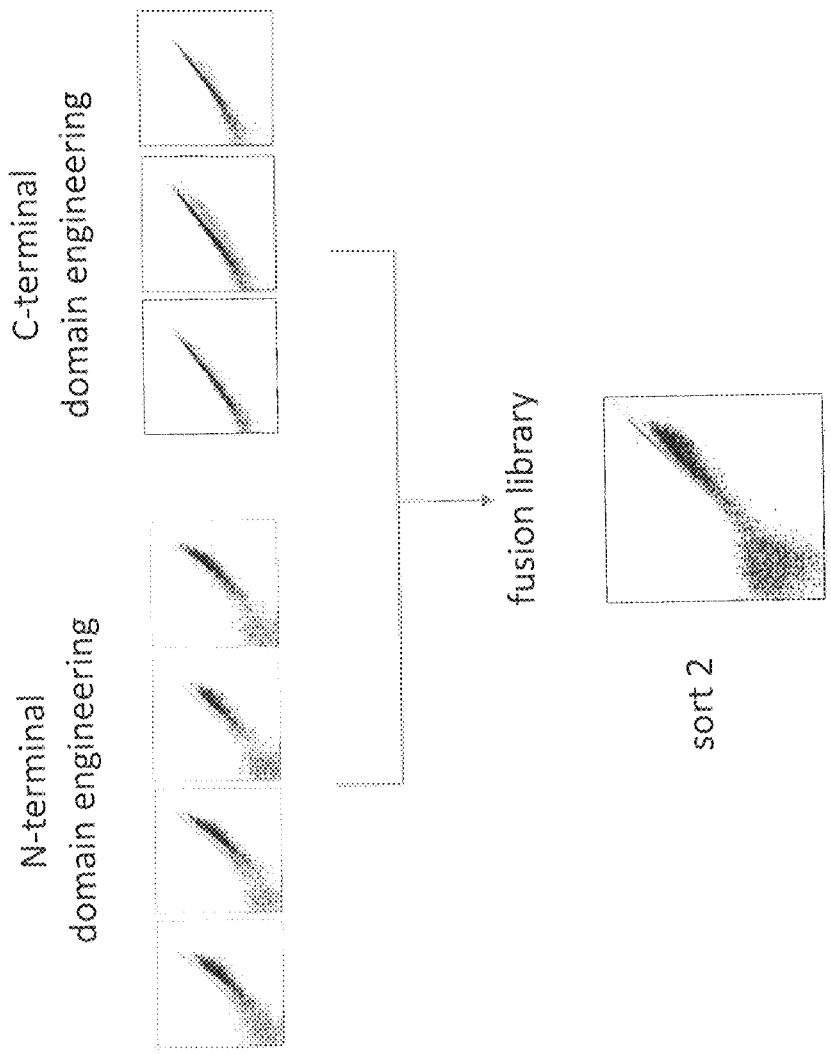
FIG. 2 shows how the CBLB HE was reprogrammed via engineering of the NTD and CTD against chimeric 'half-sites' through three rounds of sorting, followed by fusion of the reprogrammed domains and screening against the complete CBLB target site to isolate a fully reprogrammed HE.

Reprogramming I-OnuI to Disrupt the Human Casitas B-Lineage (CBL) Lymphoma Proto-Oncogene B (CBLB) Gene I-OnuI was reprogrammed to target exon 6 of the CBLB gene (FIG. 1) by constructing modular libraries containing variable amino acid residues in the DNA recognition interface. To construct the variants, degenerate codons were incorporated into I-OnuI DNA binding domains using oligonucleotides. The oligonucleotides encoding the degenerate codons were used as PCR templates to generate variant libraries by gap recombination in the yeast strain *S. cerevisiae*. Each variant library spanned either the N- or C-terminal I-OnuI DNA recognition domain and contained ~$10^7$ to $10^8$ unique transformants. The resulting surface display libraries were screened by flow cytometry for cleavage activity against target sites comprising the corresponding domains' "half-sites" (SEQ ID NOs: 23-29), as shown in FIG. 2.

Yeast displaying the N- and C-terminal domain reprogrammed I-OnuI HEs were purified and the plasmid DNA was extracted. PCR reactions were performed to amplify the reprogrammed domains, which were subsequently fused and transformed into *S. cerevisiae* to create a library of reprogrammed domain combinations. Fully reprogrammed I-OnuI variants that recognize the complete target site (SEQ ID NO: 20) present in exon 6 of the CBLB gene were identified from this library and purified.

Example 2

Reprogrammed I-OnuI Homing Endonucleases that Target Exon 6 of the CBLB Gene

Figure 3:
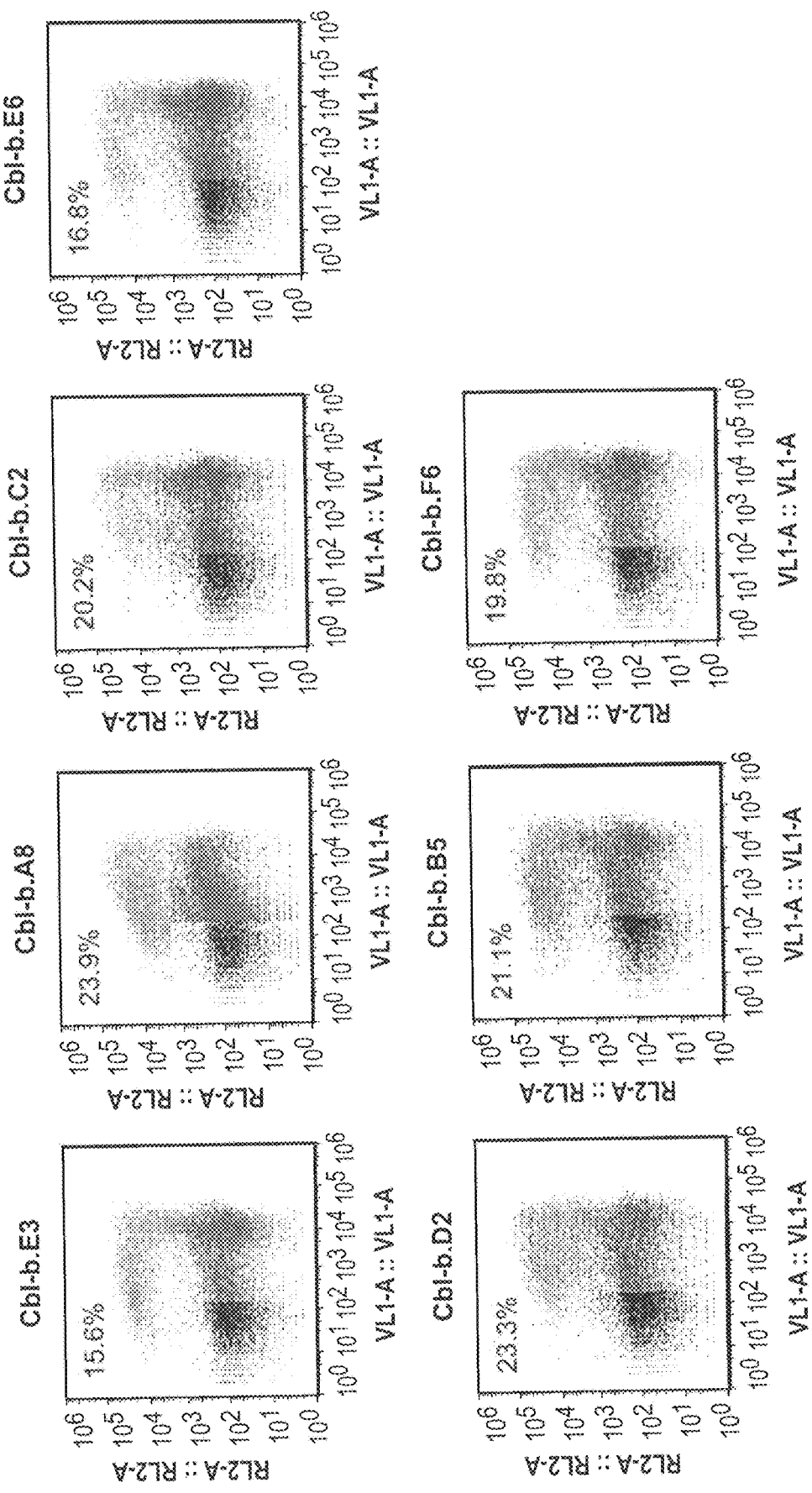
FIG. 3 shows the activity of CBLB HE variants in a chromosomal reporter assay.

The activity of reprogrammed I-OnuI HEs that target exon 6 of the CBLB gene was measured using a chromosomally integrated fluorescent reporter system (Certo et. al., 2011). Fully reprogrammed I-OnuI HEs that bind and cleave the CBLB target sequence (SEQ ID NO: 20) were cloned into mammalian expression plasmids and then individually transfected into a HEK 293T fibroblast cell line that contained the CBLB target sequence upstream of an out-of-frame gene encoding the fluorescent iRFP protein. Cleavage of the embedded target site by the HE and the accumulation of indels following DNA repair via the non-homologous end joining (NHEJ) pathway results in approximately one out of three repaired loci placing the fluorescent reporter gene back "in-frame". The percentage of iRFP fluorescing HEK 293T cells is therefore used a readout of endonuclease activity at the chromosomally embedded target sequence. The fully reprogrammed I-OnuI HEs that bind and cleave the CBLB target sequence showed high frequency iRFP expression in a cellular chromosomal context, which indicates that the HE variants had the desired property of high editing efficiency in a cellular chromosomal context. FIG. 3.

Figure 4:
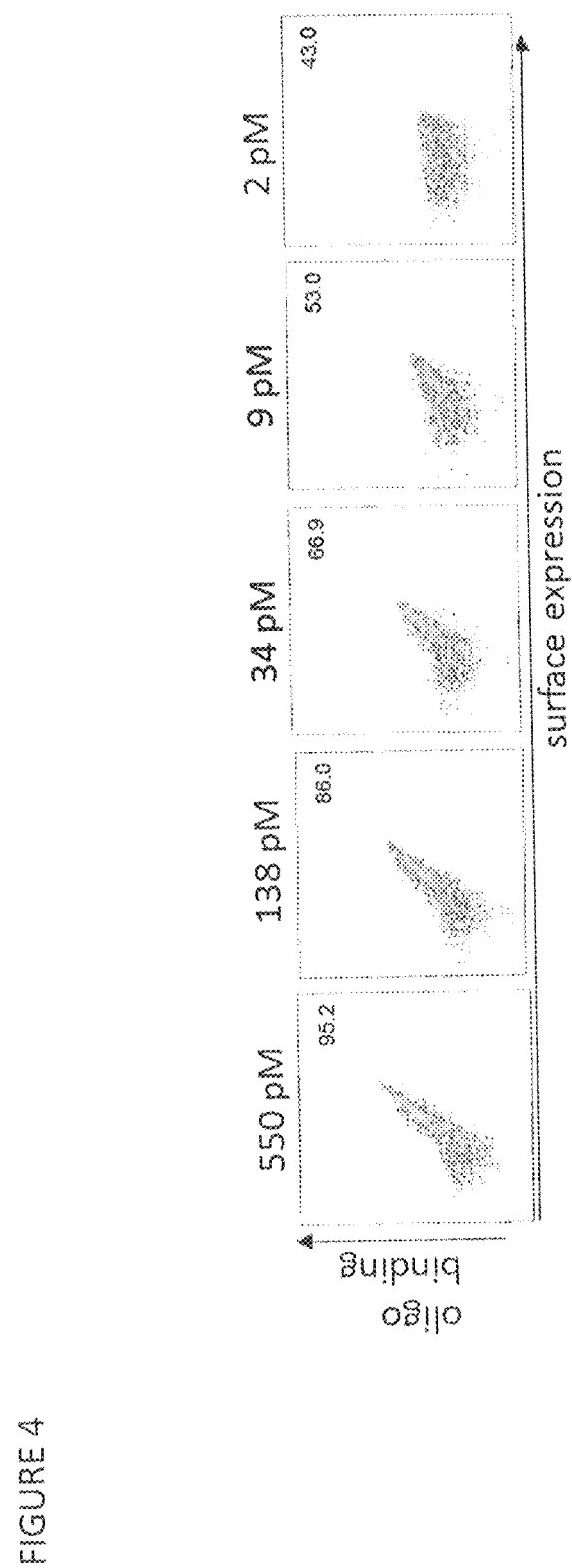
FIG. 4 shows a yeast surface affinity titration of the CBLB.E3 HE variant.

The CBLB.E3 HE variant had sub-nanomolar affinity for the exon 6 target site. FIG. 4. FIG. 5 shows the relative alignments of representative I-OnuI variants as well as the positional information of the residues comprising the DNA recognition interface.

Example 3

Characterization of megaTALs that Target CBLB Exon 6

Figure 6:
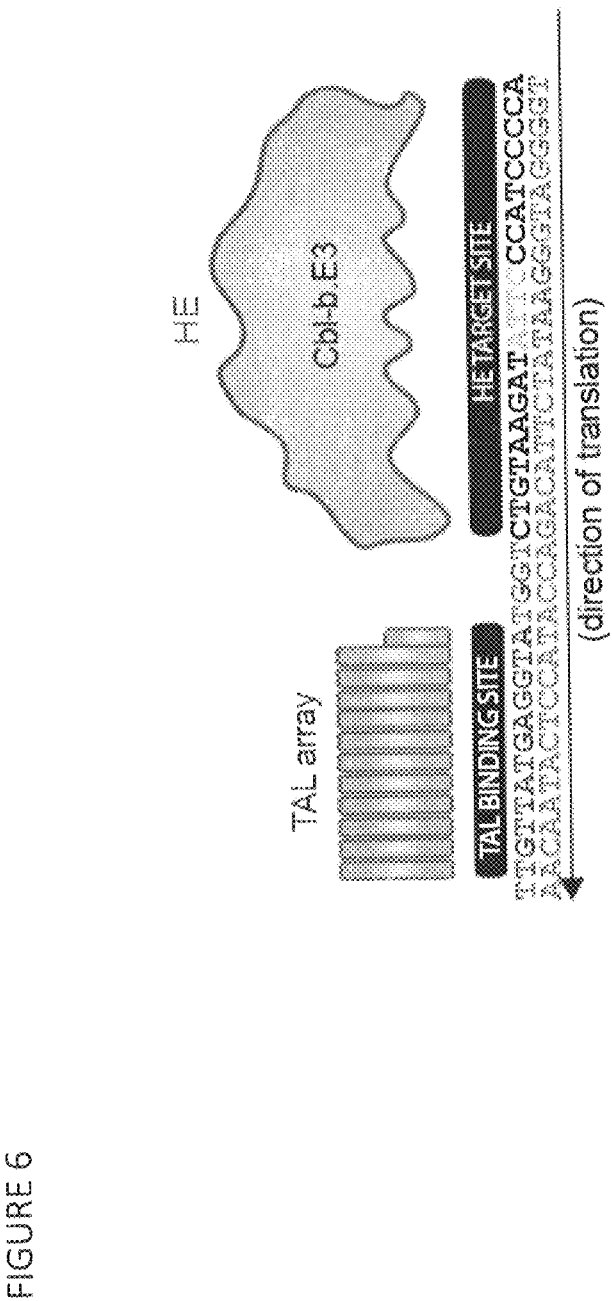
FIG. 6 shows the binding site (SEQ ID NOs: 22 and 84) for the TAL RVDs fused to the CBLB.E3 HE variant to generate a CBLB.E3 megaTAL.

The CBLB.E3, CBLB.A8, CBLB.B5, CBLB.D2, and CBLB.F6 HE variants were formatted as megaTALs (SEQ ID NOs: 13-19) by appending an 11.5 unit TAL array, corresponding to an 12 base pair TAL array target site (SEQ ID NO: 21), to the N-terminus of the meganuclease domain (as described in Boissel et al., 2013). FIG. 6. The megaTAL target site sequence is set forth in SEQ ID NO: 22.

The megaTAL editing efficiency was assessed by pre-stimulating primary human T cells with anti-CD3 and anti-CD28 antibodies in cytokine-supplemented media for 48-72 hours, and then electroporating the cells with in vitro transcribed (IVT), capped, and polyadenylated mRNA encoding a megaTAL. Additionally, IVT-mRNA encoding the 3' to 5' exonuclease Trex2 was added to enhance break processing by the non-homologous end-joining (NHEJ) pathway (see Certo et al., 2012).

Figure 7:
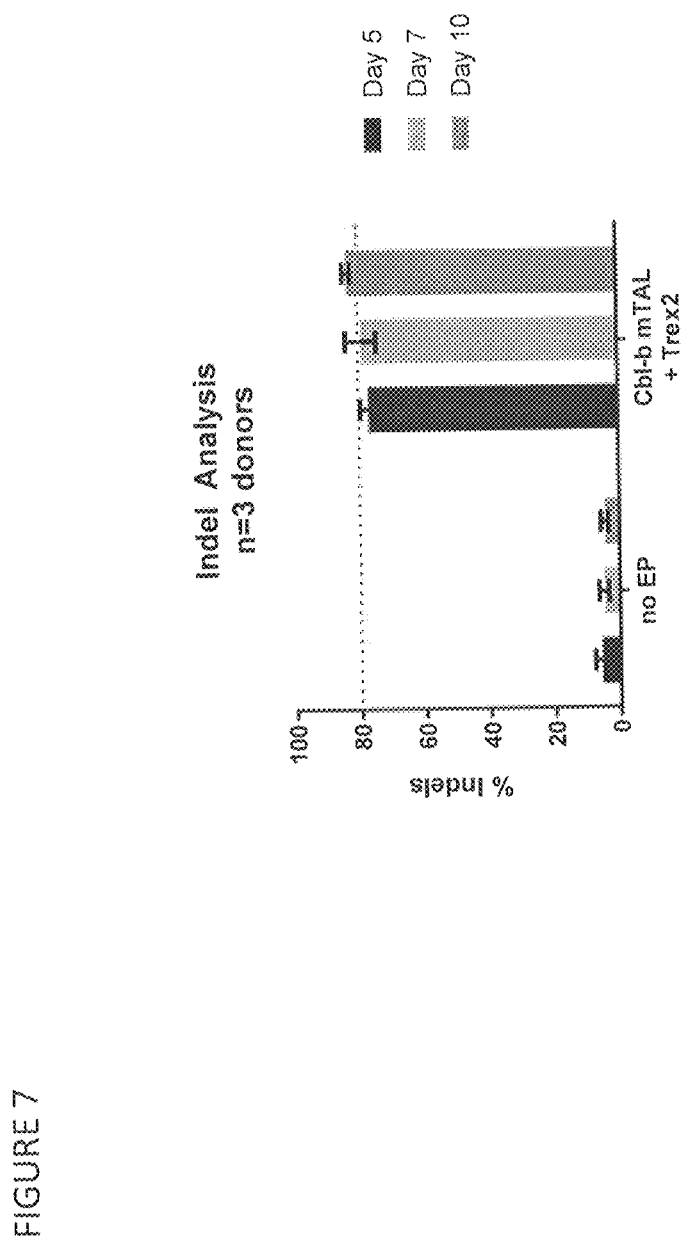
FIG. 7 shows consistent CBLB gene editing rates in CAR T cells using a CBLB megaTAL.
Figure 8:
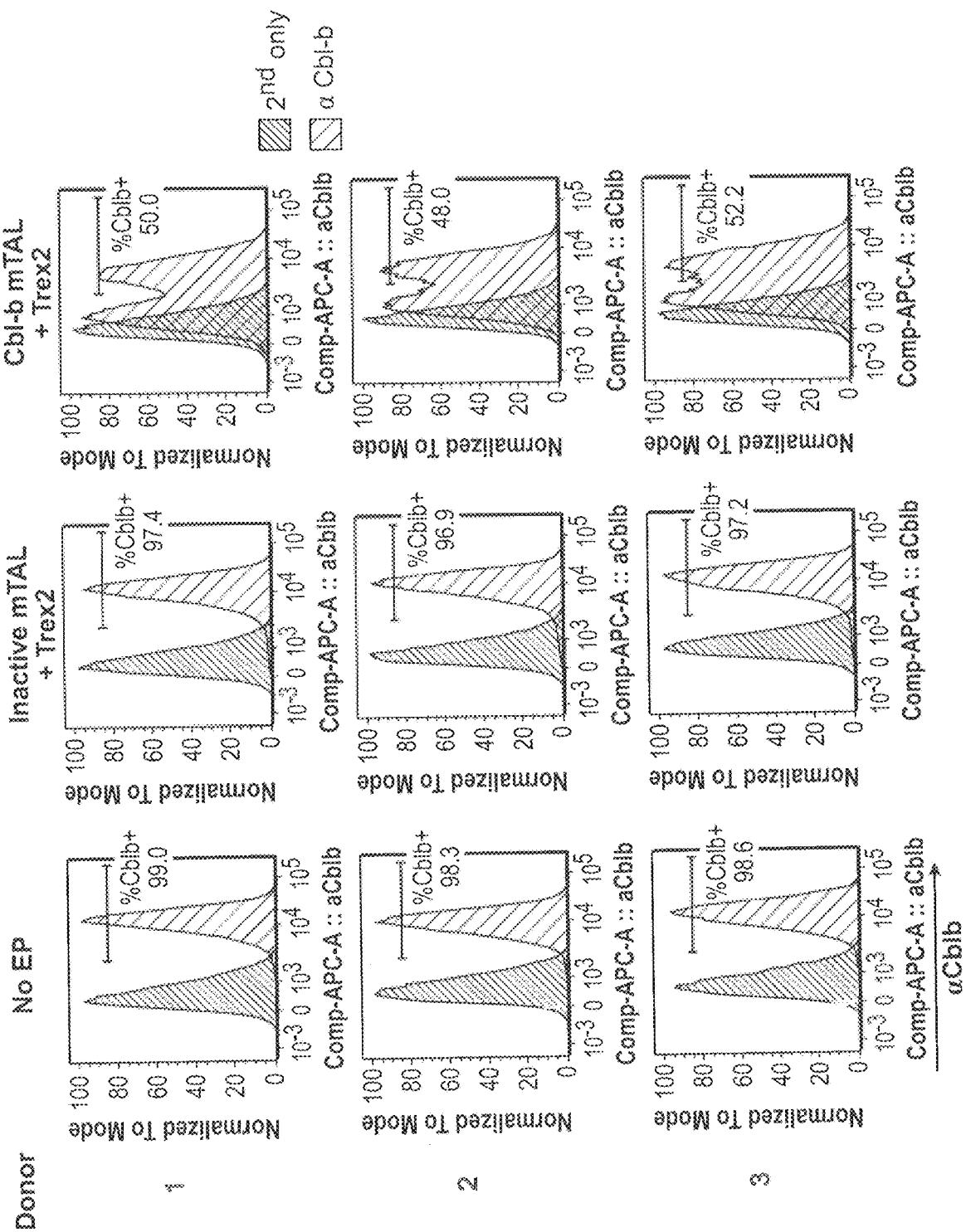
FIG. 8 shows decreased intracellular CBLB protein expression in T cells treated with a CBLB megaTAL.

In one set of experiments, cells were cultured for 7 days post-electroporation (10 day total culture) and editing efficiency was measured by isolating genomic DNA on days 5, 7 and 10 of culture and sequencing across the CBLB target site to measure indel frequency. FIG. 7. CBLB protein levels were measured by intracellular FACS analysis of CD3+ T cells. FIG. 8.

Figure 9:
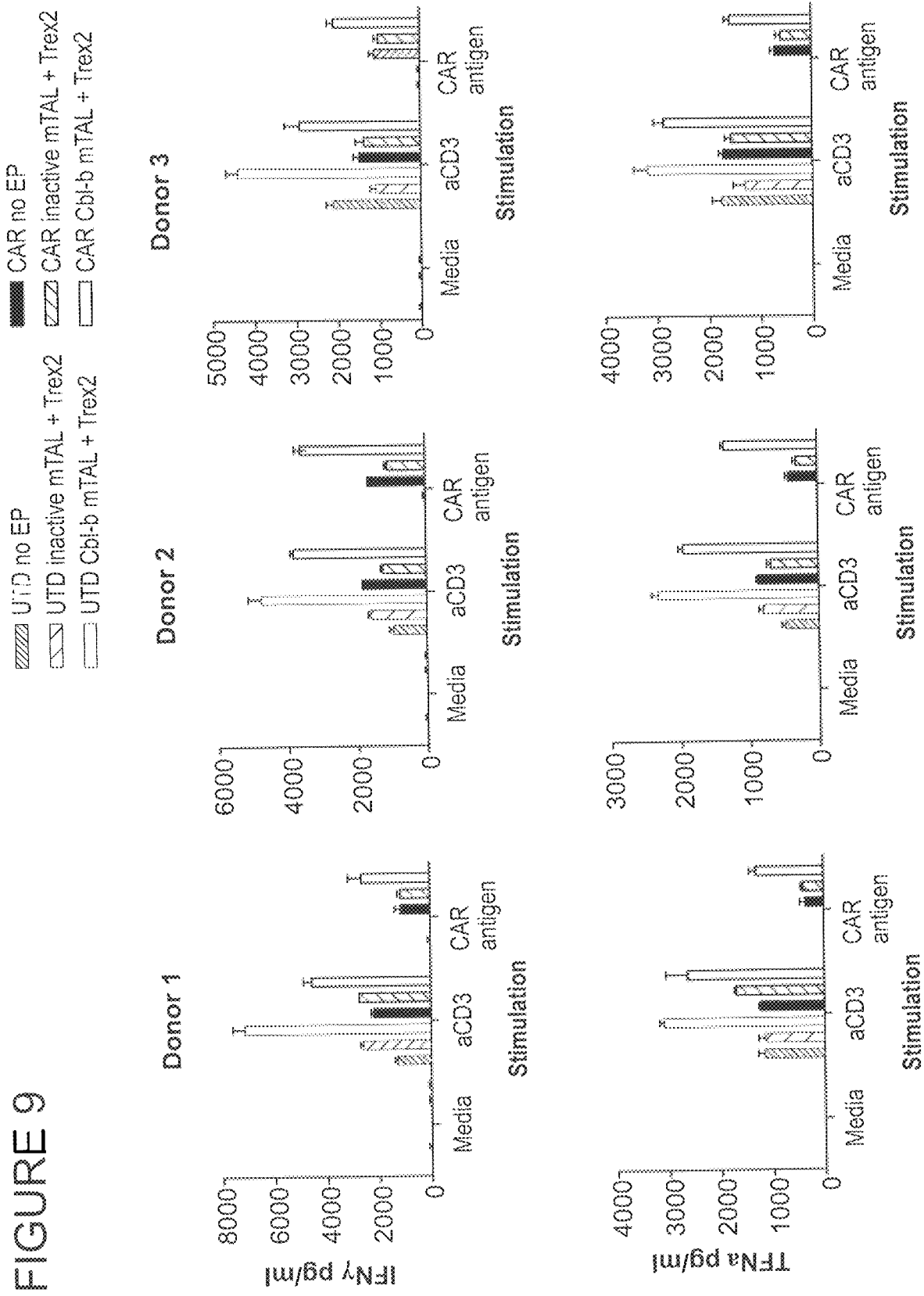
FIG. 9 shows that CBL-edited T cells produce more IFNγ and TNFα when stimulated by an anti-CD3 antibody, or by a CAR specific antigen.

T cells or CAR T cells edited with a CBLB megaTAL showed increased levels of cytokine production when stimulated with anti-CD3 agonistic antibodies or CAR-specific antigen, respectively, compared to unedited T cells and CAR T cells that either lacked active megaTAL (electroporated with inactive megaTAL) or lacked megaTAL altogether (no EP). FIG. 9.

Figure 10:
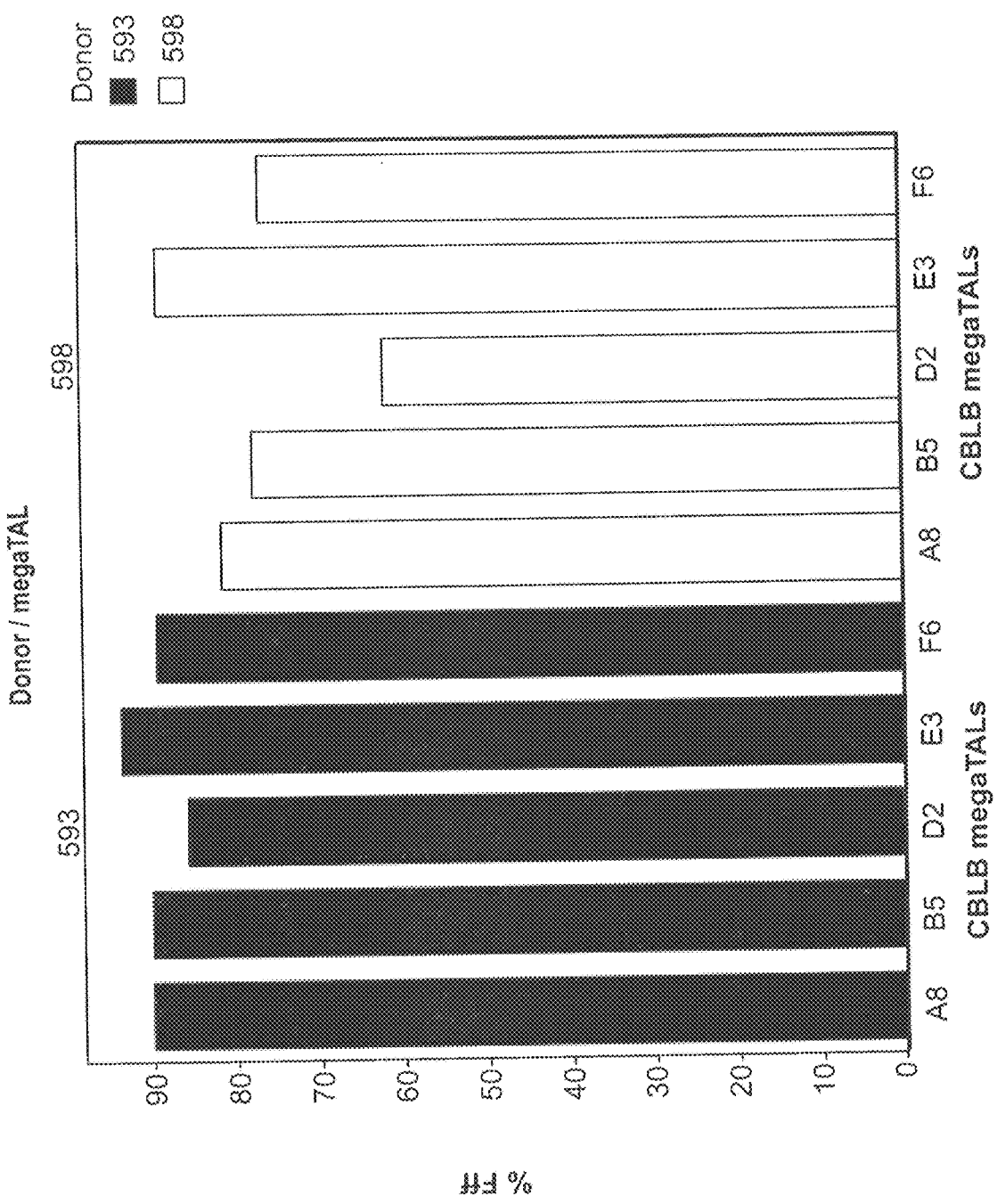
FIG. 10 shows a TIDE analysis of T cells edited by co-delivery of mRNAs encoding various CBLB megaTALs and TREX2. Editing rate at the target locus was 61-93%.

In another set of experiments, cells were cultured for 7-10 days in cytokine-supplemented media. At day 7 post-electoporation, genomic DNA was isolated followed by PCR amplification across the CBLB exon 6 target site. The frequency of indels was measured using Tracking of Indels by DEcomposition (TIDE, see Brinkman et al., 2014). FIG. 10 shows a representative TIDE analysis.

Example 4

Illustrative Homology Directed Repair Strategy Using a CBLB megaTAL

Figure 11:
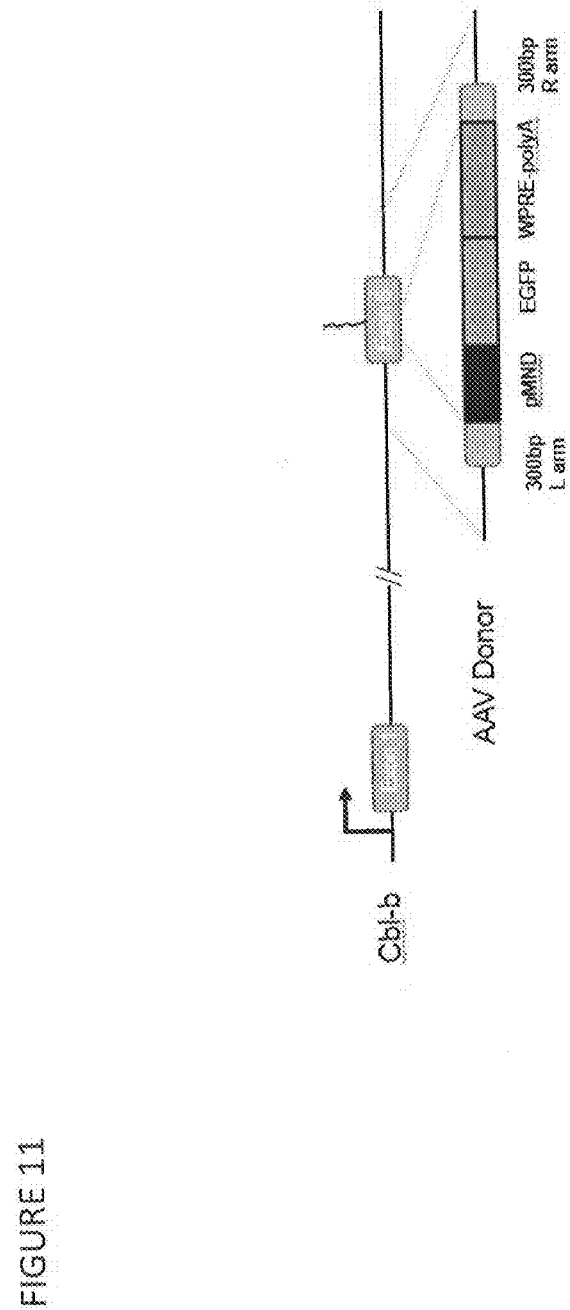
FIG. 11 shows a diagram of an HDR strategy to insert a MND-GFP expression cassette into a CBLB target site using a CBLB megaTAL and an AAV donor.
Figure 12:
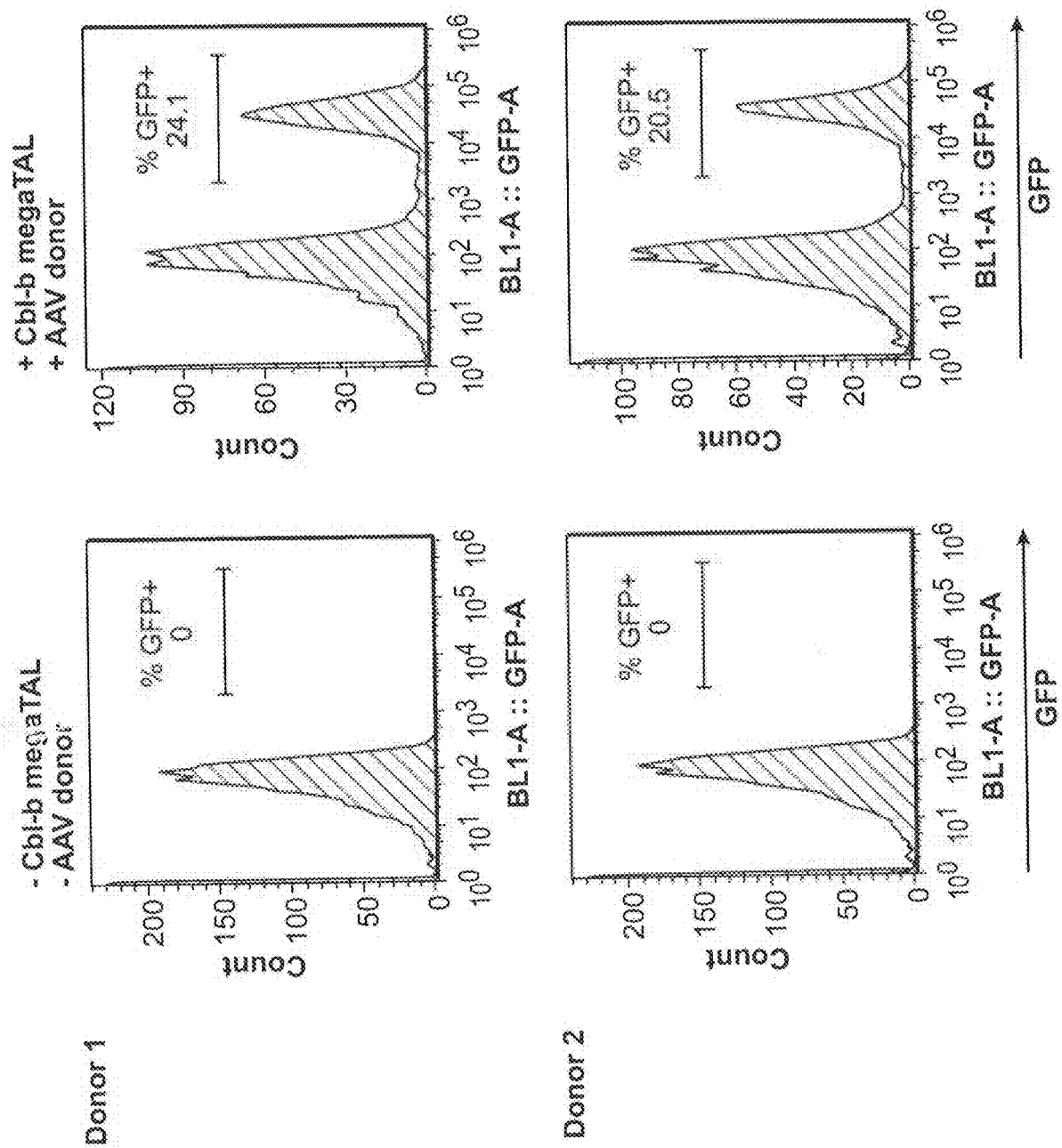
FIG. 12 shows a stable increase in GFP expression in T cells edited using the HDR strategy depicted in FIG. 11 compared to mock edited T cells.
Figure 13:
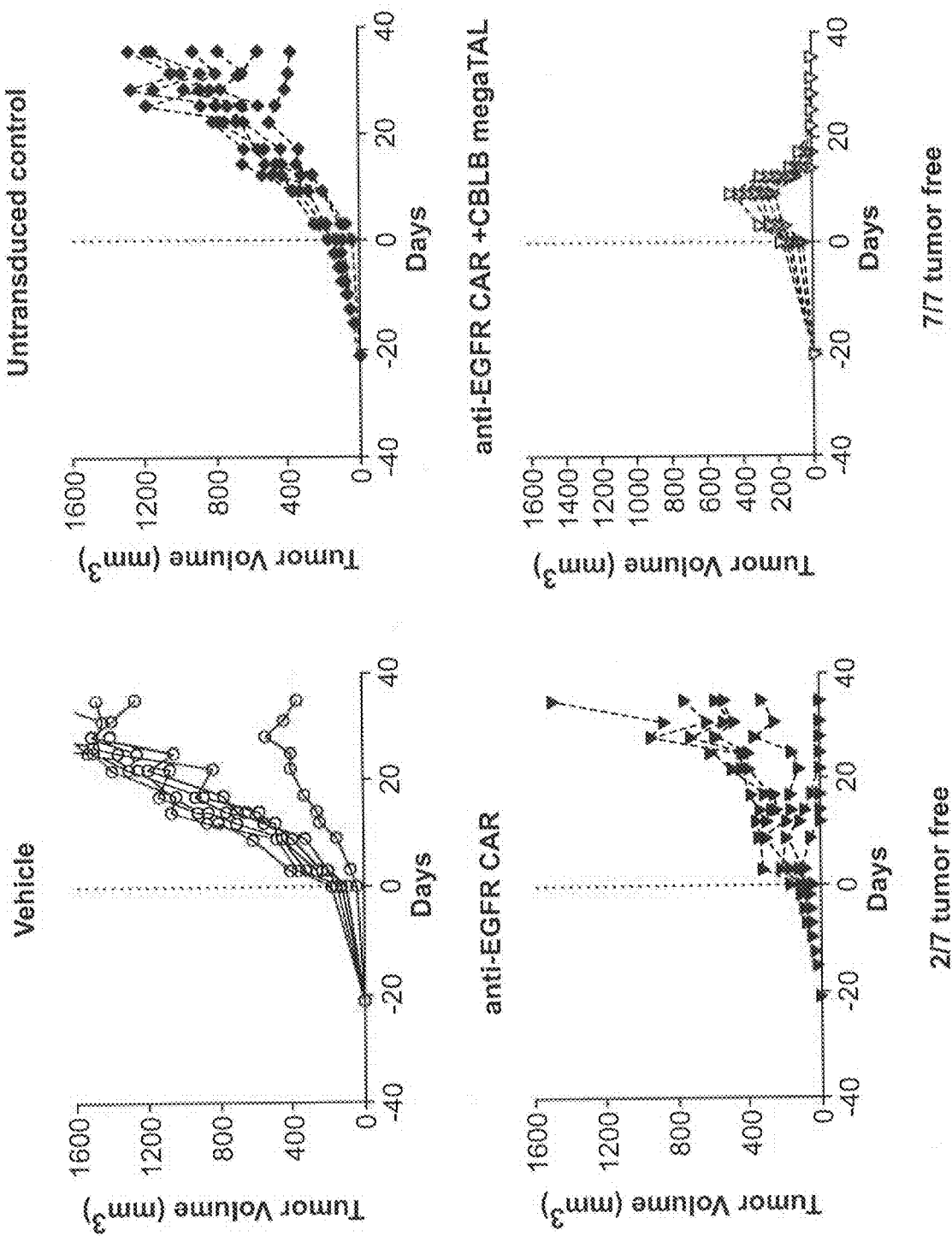
FIG. 13 shows results of an in vivo mouse study. Mice with A549 tumors were treated with vehicle treated T cells (upper left panel), T cells edited with a CBLB megaTAL (upper right panel), anti-EGFR CAR T cells (lower left panel), and anti-EGFR CAR T cells edited with a CBLB megaTAL (lower right panel). Mean tumor volume was measured over time.

An adeno-associated virus (AAV) plasmid containing transgene cassettes comprising a myeloproliferative sarcoma virus enhancer, negative control region deleted, dl587rev primer-binding site substituted (MND) promoter operably linked to a transgene encoding a fluorescent protein (GFP), posttranscriptional regulatory element of woodchuck hepatitis virus (WPRE) and an SV40 late polyadenylation signal was designed and constructed (FIG. 11, AAV donor). The integrity of AAV plasmid was confirmed with XmaI digest and sequencing. The transgene cassette was placed between two 0.3 kb homology regions flanking the CBLB megaTAL cleavage site (SEQ ID NO: 20, 22). Neither homology region contained the complete megaTAL target site.

Recombinant AAV (rAAV) was prepared by transiently co-transfecting HEK 293T cells with one or more plasmids providing the replication, capsid, and adenoviral helper elements necessary. Recombinant AAV was purified from the co-transfected HEK 293T cell culture using ultracentrifugation in an iodixanol-based gradient.

megaTAL-induced homologous recombination was evaluated in primary human T cells activated with CD3 and CD28 and cultured in complete media supplemented with IL-2. After 3 days, T cells were washed and electroporated with in vitro transcribed mRNA encoding the CBLB.A8 megaTAL (SEQ ID NO: 32), and subsequently transduced with purified recombinant AAV encoding the DNA donor repair template comprising the MND-GFP transgene cassette described above. Flow cytometry was used at multiple time points to measure the frequency of T cells expressing the fluorescent protein and to differentiate transient expression of the fluorescent protein from the non-integrated rAAV targeting vector.

Long-term transgene expression was observed in 21-24% of the T cells that were treated with both the megaTAL and the rAAV targeting vector. In constrast, untreated control samples did not express detectable levels of fluorescent protein. Results were confirmed in experiments performed on T cells isolated from independent donors.

Example 5

CBL-B Edited Anti-EGFR CAR T Cells Show Increased Anti-Tumor Efficacy in an In Vivo Tumor Model Anti-EGFR CAR T cells were used to test the effect of CBLB gene editing on CAR T cell pharmacology in an in vivo A549 tumor model in mice.

Human PBMCs (1×10⁶ cells/mL) were activated with soluble anti-CD3 and anti-CD28 antibodies on day 0. After 24 hr incubation, 1×10⁶ cells were transduced with an anti-EGFR CAR lentivirus. Seventy-two hours post-antibody stimulation, transduced PBMCs or untransduced control PBMCs were electroporated (Lonza Nucleofector) with or without in vitro transcribed mRNA encoding a CBLB.E3 megaTAL (SEQ ID NO: 31). Electroporated cells were cultured in media containing IL-2 for 10 days. After culture, 71% of the T cells were CBLB-negative as assessed by next generation sequencing (NGS) indel analysis.

Mice received a subcutaneous administration of an epithelial carcinoma cell line (A549) and tumor growth was monitored using caliper measurements. Mice were infused with equivalent CAR⁺ T cell doses (3×10⁷ CAR⁺ T cells) when mean tumor volume reached 120 mm³. Vehicle treated T cells and untransduced control T cells had minimal impact on tumor growth. Animals treated with anti-EGFR CAR T cells without a CBLB edit were able to delay tumor outgrowth compared to the control groups; two of the seven mice exhibited complete tumor control. In contrast, all seven mice receiving CBLB edited anti-EGFR CAR T cells fully cleared the A549 tumors and remained tumor-free for the duration of the study (35 days post CAR T cell injection).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A polypeptide comprising an I-OnuI homing endonuclease (HE) variant that comprises an amino acid sequence that is at least 90% identical to SEQ ID NO: 6 and that binds and cleaves a target site in the human casitas B-lineage (Cbl) lymphoma proto-oncogene B (CBLB) gene, wherein the target site is SEQ ID NO: 20.

2. The polypeptide of claim 1, wherein the I-OnuI HE variant comprises an amino acid sequence that is at least 95% identical to SEQ ID NO: 6.

3. The polypeptide of claim 1, wherein the I-OnuI HE variant comprises an amino acid sequence that is at least 99% identical to SEQ ID NO: 6.

4. The polypeptide of claim 1, wherein the I-OnuI HE variant comprises the amino acid sequence set forth in SEQ ID NO: 6.

5. The polypeptide of claim 1, further comprising a TALE DNA binding domain, wherein the polypeptide binds and cleaves a target site in the human CBLB gene, wherein the target site is SEQ ID NO: 22.

6. The polypeptide of claim 5, wherein the TALE DNA binding domain comprises about 9.5 TALE repeat units to about 15.5 TALE repeat units.

7. The polypeptide of claim 5, wherein the TALE DNA binding domain comprises about 12.5 TALE repeat units.

8. The polypeptide of claim 5, wherein the TALE DNA binding domain comprises 12.5 TALE repeat units.

9. The polypeptide of claim 5, wherein the TALE DNA binding domain binds the polynucleotide sequence set forth in SEQ ID NO: 21.

10. The polypeptide of claim 5, wherein the I-OnuI HE variant comprises an amino acid sequence that is at least 95% identical to SEQ ID NO: 6.

11. The polypeptide of claim 5, wherein the I-OnuI HE variant comprises an amino acid sequence that is at least 99% identical to SEQ ID NO: 6.

12. The polypeptide of claim 5, wherein the I-OnuI HE variant comprises the amino acid sequence set forth in SEQ ID NO: 6.

* * * * *

```
                      SEQUENCE LISTING

<160> NUMBER OF SEQ ID NOS: 84

<210> SEQ ID NO 1
<211> LENGTH: 303
<212> TYPE: PRT
<213> ORGANISM: Ophiostoma novo-ulmi

<400> SEQUENCE: 1

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Met Leu Phe Lys Gln
            100                 105                 110

Ala Phe Cys Val Met Glu Asn Lys Glu His Leu Lys Ile Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Ile Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255
```

```
Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Val Phe
            290                 295                 300

<210> SEQ ID NO 2
<211> LENGTH: 303
<212> TYPE: PRT
<213> ORGANISM: Ophiostoma novo-ulmi

<400> SEQUENCE: 2

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
            35                  40                  45

Leu His Asn Lys Asp Lys Ser Ile Leu Glu Asn Ile Gln Ser Thr Trp
        50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
            115                 120                 125

Lys Glu Leu Val Arg Ile Lys Ala Lys Leu Asn Trp Gly Leu Thr Asp
        130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Val Phe
            290                 295                 300

<210> SEQ ID NO 3
<211> LENGTH: 303
<212> TYPE: PRT
<213> ORGANISM: Ophiostoma novo-ulmi
```

```
<220> FEATURE:
<221> NAME/KEY: MOD_RES
<222> LOCATION: (1)..(3)
<223> OTHER INFORMATION: Any amino acid or absent

<400> SEQUENCE: 3
```

| Xaa | Xaa | Xaa | Met | Ser | Arg | Arg | Glu | Ser | Ile | Asn | Pro | Trp | Ile | Leu | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Phe | Ala | Asp | Ala | Glu | Gly | Ser | Phe | Leu | Leu | Arg | Ile | Arg | Asn | Asn |
|     |     |     | 20  |     |     |     |     | 25  |     |     |     |     | 30  |     |     |
| Asn | Lys | Ser | Ser | Val | Gly | Tyr | Ser | Thr | Glu | Leu | Gly | Phe | Gln | Ile | Thr |
|     |     | 35  |     |     |     |     | 40  |     |     |     |     | 45  |     |     |     |
| Leu | His | Asn | Lys | Asp | Lys | Ser | Ile | Leu | Glu | Asn | Ile | Gln | Ser | Thr | Trp |
| 50  |     |     |     |     | 55  |     |     |     |     | 60  |     |     |     |     |     |
| Lys | Val | Gly | Val | Ile | Ala | Asn | Ser | Gly | Asp | Asn | Ala | Val | Ser | Leu | Lys |
| 65  |     |     |     | 70  |     |     |     |     | 75  |     |     |     |     | 80  |     |
| Val | Thr | Arg | Phe | Glu | Asp | Leu | Lys | Val | Ile | Ile | Asp | His | Phe | Glu | Lys |
|     |     |     |     | 85  |     |     |     |     | 90  |     |     |     |     | 95  |     |
| Tyr | Pro | Leu | Ile | Thr | Gln | Lys | Leu | Gly | Asp | Tyr | Lys | Leu | Phe | Lys | Gln |
|     |     |     | 100 |     |     |     |     | 105 |     |     |     |     | 110 |     |     |
| Ala | Phe | Ser | Val | Met | Glu | Asn | Lys | Glu | His | Leu | Lys | Glu | Asn | Gly | Ile |
|     |     | 115 |     |     |     |     | 120 |     |     |     |     | 125 |     |     |     |
| Lys | Glu | Leu | Val | Arg | Ile | Lys | Ala | Lys | Leu | Asn | Trp | Gly | Leu | Thr | Asp |
| 130 |     |     |     |     | 135 |     |     |     |     | 140 |     |     |     |     |     |
| Glu | Leu | Lys | Lys | Ala | Phe | Pro | Glu | Asn | Ile | Ser | Lys | Glu | Arg | Ser | Leu |
| 145 |     |     |     | 150 |     |     |     |     | 155 |     |     |     |     | 160 |     |
| Ile | Asn | Lys | Asn | Ile | Pro | Asn | Phe | Lys | Trp | Leu | Ala | Gly | Phe | Thr | Ser |
|     |     |     | 165 |     |     |     |     | 170 |     |     |     |     | 175 |     |     |
| Gly | Glu | Gly | Cys | Phe | Phe | Val | Asn | Leu | Ile | Lys | Ser | Lys | Ser | Lys | Leu |
|     |     |     | 180 |     |     |     |     | 185 |     |     |     |     | 190 |     |     |
| Gly | Val | Gln | Val | Gln | Leu | Val | Phe | Ser | Ile | Thr | Gln | His | Ile | Lys | Asp |
|     |     |     | 195 |     |     |     |     | 200 |     |     |     |     | 205 |     |     |
| Lys | Asn | Leu | Met | Asn | Ser | Leu | Ile | Thr | Tyr | Leu | Gly | Cys | Gly | Tyr | Ile |
| 210 |     |     |     |     | 215 |     |     |     |     | 220 |     |     |     |     |     |
| Lys | Glu | Lys | Asn | Lys | Ser | Glu | Phe | Ser | Trp | Leu | Asp | Phe | Val | Val | Thr |
| 225 |     |     |     | 230 |     |     |     |     | 235 |     |     |     |     | 240 |     |
| Lys | Phe | Ser | Asp | Ile | Asn | Asp | Lys | Ile | Ile | Pro | Val | Phe | Gln | Glu | Asn |
|     |     |     |     | 245 |     |     |     |     | 250 |     |     |     |     | 255 |     |
| Thr | Leu | Ile | Gly | Val | Lys | Leu | Glu | Asp | Phe | Glu | Asp | Trp | Cys | Lys | Val |
|     |     |     | 260 |     |     |     |     | 265 |     |     |     |     | 270 |     |     |
| Ala | Lys | Leu | Ile | Glu | Glu | Lys | Lys | His | Leu | Thr | Glu | Ser | Gly | Leu | Asp |
|     |     | 275 |     |     |     |     | 280 |     |     |     |     | 285 |     |     |     |
| Glu | Ile | Lys | Lys | Ile | Lys | Leu | Asn | Met | Asn | Lys | Gly | Arg | Val | Phe |     |
|     | 290 |     |     |     |     | 295 |     |     |     |     | 300 |     |     |     |     |

```
<210> SEQ ID NO 4
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 4
```

Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
            35                  40                  45

Leu His Asn Lys Asp Lys Ser Ile Leu Glu Asn Ile Gln Ser Thr Trp
50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
            115                 120                 125

Lys Glu Leu Val Arg Ile Lys Ala Lys Leu Asn Trp Gly Leu Thr Asp
130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
            195                 200                 205

Lys Asn Leu Met Asn Ser Leu Ile Thr Tyr Leu Gly Cys Gly Tyr Ile
210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa
290                 295                 300

<210> SEQ ID NO 5
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(8)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 5

Xaa Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
            35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Asp His Phe Glu Lys
                85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
            115                 120                 125

Lys Glu Leu Val Arg Ile Lys Ala Lys Leu Asn Trp Gly Leu Thr Asp
            130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
            195                 200                 205

Lys Asn Leu Met Asn Ser Leu Ile Thr Tyr Leu Gly Cys Gly Tyr Ile
            210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa
            290                 295                 300

<210> SEQ ID NO 6
<211> LENGTH: 306
<212> TYPE: PRT
<213> ORGANISM: Artificial Sequence
<220> FEATURE:
<223> OTHER INFORMATION: Synthesized I-OnuI variant CBLB.E3
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 6

Xaa Xaa Xaa Xaa Ser Arg Arg Glu Ser Ile Asn Pro Trp Ile Leu Thr
1               5                   10                  15

Gly Phe Ala Asp Ala Glu Gly Cys Phe Arg Leu Asp Ile Arg Asn Ala
            20                  25                  30

Asn Asp Leu Arg Ala Gly Tyr Arg Thr Arg Leu Ala Phe Glu Ile Val
            35                  40                  45

```
Leu His Asn Lys Asp Lys Ser Ile Leu Glu Asn Ile Gln Ser Thr Trp
 50                  55                  60

Lys Val Gly Thr Ile Tyr Asn Ala Gly Asp Asn Ala Val Arg Leu Gln
 65                  70                  75                  80

Val Thr Arg Phe Glu Asp Leu Lys Val Ile Asp His Phe Glu Lys
                 85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Leu Lys Trp Leu Ala Gly Phe Thr Ser
                165                 170                 175

Gly Asp Gly Ser Phe Val Val Glu Leu Lys Lys Arg Arg Ser Pro Val
                180                 185                 190

Lys Val Gly Val Arg Leu Arg Phe Ser Ile Thr Gln His Ile Arg Asp
                195                 200                 205

Lys Asn Leu Met Asn Ser Leu Ile Thr Tyr Leu Gly Cys Gly Arg Ile
210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
                275                 280                 285

Glu Ile Lys Lys Ile Lys Leu Asn Met Asn Lys Gly Arg Xaa Xaa Xaa
                290                 295                 300

Xaa Xaa
305

<210> SEQ ID NO 7
<211> LENGTH: 306
<212> TYPE: PRT
<213> ORGANISM: Artificial Sequence
<220> FEATURE:
<223> OTHER INFORMATION: Synthesized I-OnuI variant CBLB.F6
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 7

Xaa Xaa Xaa Xaa Ser Arg Arg Glu Ser Ile Asn Pro Trp Ile Leu Thr
 1               5                  10                  15

Gly Phe Ala Asp Ala Glu Gly Cys Phe Arg Leu Asp Ile Arg Asn Ala
                 20                  25                  30

Asn Asp Leu Arg Ala Gly Tyr Arg Thr Arg Leu Ala Phe Glu Ile Val
                 35                  40                  45

Leu His Asn Lys Asp Lys Ser Ile Leu Glu Asn Ile Gln Ser Thr Trp
```

```
            50                  55                  60
Lys Val Gly Thr Ile Tyr Asn Ala Gly Asp Asn Ala Val Arg Leu Gln
 65                  70                  75                  80

Val Thr Arg Phe Glu Asp Leu Lys Val Ile Ile Asp His Phe Glu Lys
                 85                  90                  95

Tyr Pro Leu Ile Thr Gln Lys Leu Gly Asp Tyr Lys Leu Phe Lys Gln
             100                 105                 110

Ala Phe Ser Val Met Glu Asn Lys Glu His Leu Lys Glu Asn Gly Ile
         115                 120                 125

Lys Glu Leu Val Arg Ile Lys Ala Lys Met Asn Trp Gly Leu Asn Asp
     130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175

Gly Asp Gly Ser Phe Met Val Glu Leu Met Lys Asn Lys Asn Asn Val
            180                 185                 190

Ile Val Arg Val Arg Leu Arg Phe Ser Ile Ser Gln His Ile Arg Asp
        195                 200                 205

Lys Asn Leu Met Asn Ser Leu Ile Thr Tyr Leu Gly Cys Gly Arg Ile
    210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Xaa Xaa Xaa
    290                 295                 300

Xaa Xaa
305

<210> SEQ ID NO 8
<211> LENGTH: 306
<212> TYPE: PRT
<213> ORGANISM: Artificial Sequence
<220> FEATURE:
<223> OTHER INFORMATION: Synthesized I-OnuI variant CBLB.E6
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 8

Xaa Xaa Xaa Xaa Ser Arg Arg Glu Ser Ile Asn Pro Trp Ile Leu Thr
 1               5                  10                  15

Gly Phe Ala Asp Ala Glu Gly Cys Phe Arg Leu Asp Ile Arg Asn Ala
             20                  25                  30

Asn Asp Leu Arg Ala Gly Tyr Arg Thr Arg Leu Ser Phe Glu Ile Ser
         35                  40                  45

Leu His Asn Lys Asp Lys Ser Ile Leu Glu Asn Ile Gln Ser Thr Trp
     50                  55                  60
```

-continued

Lys Val Gly Thr Ile Tyr Asn Ala Gly Asp Asn Ala Val Arg Leu Gln
 65                  70                  75                  80

Val Thr Arg Phe Glu Asp Leu Lys Val Ile Asp His Phe Glu Lys
             85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
                115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Gly Arg Pro Leu
145                 150                 155                 160

Ile Asn Lys Asn Ile Pro Asn Leu Lys Trp Leu Ala Gly Phe Thr Ser
                165                 170                 175

Gly Asp Gly Ser Phe Met Val Glu Leu Met Lys Asn Lys Asn Asn Val
                180                 185                 190

Ile Val Arg Val Arg Leu Arg Phe Ser Ile Ser Gln His Ile Arg Asp
            195                 200                 205

Lys Asn Leu Met Asn Ser Leu Ile Thr Tyr Leu Gly Cys Gly Arg Ile
210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa Xaa
    290                 295                 300

Xaa Xaa
305

<210> SEQ ID NO 9
<211> LENGTH: 306
<212> TYPE: PRT
<213> ORGANISM: Artificial Sequence
<220> FEATURE:
<223> OTHER INFORMATION: Synthesized I-OnuI variant CBLB.D2
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 9

Xaa Xaa Xaa Xaa Ser Arg Arg Glu Ser Ile Asn Pro Trp Ile Leu Thr
  1               5                  10                  15

Gly Phe Ala Asp Ala Glu Gly Cys Phe Arg Leu Asp Ile His Asn Ala
             20                  25                  30

Asn Val Leu Arg Ser Gly Tyr Arg Thr Arg Leu Ser Phe Glu Ile Val
         35                  40                  45

Leu His Asn Lys Asp Lys Ser Ile Leu Glu Asn Ile Gln Ser Thr Trp
     50                  55                  60

Lys Val Gly Lys Ile Tyr Asn Ala Gly Asp Asn Ala Val Arg Leu Gln
65                  70                  75                  80

Val Thr Arg Phe Glu Asp Leu Lys Val Ile Ile Asp His Phe Glu Lys
            85                  90                  95

Tyr Pro Leu Ile Thr Gln Lys Leu Gly Asp Tyr Lys Leu Phe Lys Gln
        100                 105                 110

Ala Phe Ser Val Met Glu Asn Lys Glu His Leu Lys Glu Asn Gly Ile
    115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175

Gly Asp Gly Ser Phe Met Val Glu Leu Met Lys Asn Lys Asn Asn Val
            180                 185                 190

Ile Val Arg Val Arg Leu Arg Phe Ser Ile Ser Gln His Ile Arg Asp
        195                 200                 205

Lys Asn Leu Met Asn Ser Leu Ile Thr Tyr Leu Gly Cys Gly Arg Ile
210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Xaa Xaa Xaa
    290                 295                 300

Xaa Xaa
305

<210> SEQ ID NO 10
<211> LENGTH: 306
<212> TYPE: PRT
<213> ORGANISM: Artificial Sequence
<220> FEATURE:
<223> OTHER INFORMATION: Synthesized I-OnuI variant CBLB.C2
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 10

Xaa Xaa Xaa Xaa Ser Arg Arg Glu Ser Ile Asn Pro Trp Ile Leu Thr
1               5                   10                  15

Gly Phe Ala Asp Ala Glu Gly Cys Phe Gly Leu Tyr Ile His Asn Ser
            20                  25                  30

Asn Val Leu Arg Ser Gly Tyr Arg Thr Arg Leu Ser Phe Glu Ile Ser
        35                  40                  45

Leu His Asn Lys Asp Lys Ser Ile Leu Glu Asn Ile Gln Ser Thr Trp
    50                  55                  60

Lys Val Gly Thr Ile Tyr Asn Ala Gly Asp Asn Ala Val Arg Leu Gln

```
                65                  70                  75                  80
Val Thr Arg Phe Glu Asp Leu Lys Val Ile Ile Asp His Phe Glu Lys
                    85                  90                  95

Tyr Pro Leu Ile Thr Gln Lys Leu Gly Asp Tyr Lys Leu Phe Lys Gln
                100                 105                 110

Ala Phe Ser Leu Met Glu Asn Lys Glu His Leu Lys Glu Asn Gly Ile
                115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175

Gly Asp Gly Ser Phe Met Val Glu Leu Met Lys Asn Lys Asn Asn Val
                180                 185                 190

Ile Val Arg Val Arg Leu Arg Phe Ser Ile Ser Gln His Ile Arg Asp
                195                 200                 205

Lys Asn Leu Met Asn Ser Leu Ile Thr Tyr Leu Gly Cys Gly Arg Ile
210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
                275                 280                 285

Glu Ile Lys Lys Ile Lys Leu Asn Met Asn Lys Gly Arg Xaa Xaa Xaa
                290                 295                 300

Xaa Xaa
305

<210> SEQ ID NO 11
<211> LENGTH: 306
<212> TYPE: PRT
<213> ORGANISM: Artificial Sequence
<220> FEATURE:
<223> OTHER INFORMATION: Synthesized I-OnuI variant CBLB.B5
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 11

Xaa Xaa Xaa Xaa Ser Arg Arg Glu Ser Ile Asn Pro Trp Ile Leu Thr
1               5                   10                  15

Gly Phe Ala Asp Ala Glu Gly Cys Phe Arg Leu Asp Ile His Asn Ala
                20                  25                  30

Asn Val Leu Arg Ser Gly Tyr Arg Thr Arg Leu Ser Phe Glu Ile Val
                35                  40                  45

Leu His Asn Lys Asp Lys Ser Ile Leu Glu Asn Ile Gln Ser Thr Trp
                50                  55                  60

Lys Val Gly Thr Ile Tyr Asn Ala Gly Asp Asn Ala Val Arg Leu Gln
65                  70                  75                  80
```

```
Val Thr Arg Phe Glu Asp Leu Lys Val Ile Ile Asp His Phe Glu Lys
            85                  90                  95

Tyr Pro Leu Ile Thr Gln Lys Leu Gly Asp Tyr Lys Leu Phe Lys Gln
            100                 105                 110

Ala Phe Ser Leu Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
            165                 170                 175

Gly Asp Gly Ser Phe Val Val Glu Leu Lys Lys Arg Arg Ser Pro Val
            180                 185                 190

Lys Val Gly Val Arg Leu Arg Phe Gly Ile Thr Gln His Ile Arg Asp
            195                 200                 205

Lys Asn Leu Met Asn Ser Leu Ile Thr Tyr Leu Gly Cys Gly Arg Ile
            210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
            245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa Xaa
            290                 295                 300

Xaa Xaa
305

<210> SEQ ID NO 12
<211> LENGTH: 306
<212> TYPE: PRT
<213> ORGANISM: Artificial Sequence
<220> FEATURE:
<223> OTHER INFORMATION: Synthesized I-OnuI variant CBLB.A8
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(306)
<223> OTHER INFORMATION: Any amino acid or absent

<400> SEQUENCE: 12

Xaa Xaa Xaa Xaa Ser Arg Arg Glu Ser Ile Asn Pro Trp Ile Leu Thr
1               5                   10                  15

Gly Phe Ala Asp Ala Glu Gly Cys Phe Arg Leu Asp Ile Arg Asn Ala
            20                  25                  30

Asn Asp Leu Arg Ala Gly Tyr Arg Thr Arg Leu Ala Phe Glu Ile Val
            35                  40                  45

Leu His Asn Lys Asp Lys Ser Ile Leu Glu Asn Ile Gln Ser Thr Trp
        50                  55                  60

Lys Val Gly Thr Ile Tyr Asn Ala Gly Asp Asn Ala Val Arg Leu Gln
65                  70                  75                  80
```

```
Val Thr Arg Phe Glu Asp Leu Lys Val Ile Gly His Phe Glu Lys
            85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
            130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175

Gly Asp Gly Ser Phe Met Val Glu Leu Met Lys Asn Lys Asn Asn Val
            180                 185                 190

Ile Val Arg Val Arg Leu Arg Phe Ser Ile Ser Gln His Ile Arg Asp
            195                 200                 205

Lys Asn Leu Met Asn Ser Leu Ile Thr Tyr Leu Gly Cys Gly Arg Ile
210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa Xaa
            290                 295                 300

Xaa Xaa
305

<210> SEQ ID NO 13
<211> LENGTH: 914
<212> TYPE: PRT
<213> ORGANISM: Artificial Sequence
<220> FEATURE:
<223> OTHER INFORMATION: Made in Lab - synthesized megaTAL CBLB.E3
      construct

<400> SEQUENCE: 13

Met Gly Ser Ala Pro Pro Lys Lys Lys Arg Lys Val Val Asp Leu Arg
1               5                   10                  15

Thr Leu Gly Tyr Ser Gln Gln Gln Gln Glu Lys Ile Lys Pro Lys Val
            20                  25                  30

Arg Ser Thr Val Ala Gln His His Glu Ala Leu Val Gly His Gly Phe
            35                  40                  45

Thr His Ala His Ile Val Ala Leu Ser Gln His Pro Ala Ala Leu Gly
            50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
            85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
            115                 120                 125
```

```
Val Thr Ala Met Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
210                 215                 220

Ile Ala Ser Asn Gly Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Lys Gln Ala Leu Glu Thr Val
            260                 265                 270

Gln Arg Leu Leu Pro Val Leu Cys Gln Asp His Gly Leu Thr Pro Asp
            275                 280                 285

Gln Val Val Ala Ile Ala Ser Asn Ile Gly Gly Lys Gln Ala Leu Glu
    290                 295                 300

Thr Val Gln Arg Leu Leu Pro Val Leu Cys Gln Asp His Gly Leu Thr
305                 310                 315                 320

Pro Asp Gln Val Val Ala Ile Ala Ser Asn Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Asn Gly Gly Lys
        355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Ile Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Asn Gly Gly Lys Gln Ala Leu Glu Thr Val Gln Arg Leu Leu Pro Val
        435                 440                 445

Leu Cys Gln Asp His Gly Leu Thr Pro Asp Gln Val Val Ala Ile Ala
450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Gly Gly Gly Lys Gln Ala Leu Glu Thr Val Gln Arg
            500                 505                 510

Leu Leu Pro Val Leu Cys Gln Asp His Gly Leu Thr Pro Asp Gln Val
        515                 520                 525

Val Ala Ile Ala Ser Asn Ile Gly Gly Lys Gln Ala Leu Glu Ser Ile
    530                 535                 540
```

Val Ala Gln Leu Ser Arg Pro Asp Pro Ala Leu Ala Leu Thr Asn
545                 550                 555                 560

Asp His Leu Val Ala Leu Ala Cys Leu Gly Gly Arg Pro Ala Met Asp
            565                 570                 575

Ala Val Lys Lys Gly Leu Pro His Ala Pro Glu Leu Ile Arg Arg Val
        580                 585                 590

Asn Arg Arg Ile Gly Glu Arg Thr Ser His Arg Val Ala Ile Ser Arg
    595                 600                 605

Val Gly Gly Ser Ser Arg Arg Glu Ser Ile Asn Pro Trp Ile Leu Thr
610                 615                 620

Gly Phe Ala Asp Ala Glu Gly Cys Phe Arg Leu Asp Ile Arg Asn Ala
625                 630                 635                 640

Asn Asp Leu Arg Ala Gly Tyr Arg Thr Arg Leu Ala Phe Glu Ile Val
            645                 650                 655

Leu His Asn Lys Asp Lys Ser Ile Leu Glu Asn Ile Gln Ser Thr Trp
        660                 665                 670

Lys Val Gly Thr Ile Tyr Asn Ala Gly Asp Asn Ala Val Arg Leu Gln
    675                 680                 685

Val Thr Arg Phe Glu Asp Leu Lys Val Ile Ile Asp His Phe Glu Lys
690                 695                 700

Tyr Pro Leu Ile Thr Gln Lys Leu Gly Asp Tyr Lys Leu Phe Lys Gln
705                 710                 715                 720

Ala Phe Ser Val Met Glu Asn Lys Glu His Leu Lys Glu Asn Gly Ile
            725                 730                 735

Lys Glu Leu Val Arg Ile Lys Ala Lys Met Asn Trp Gly Leu Asn Asp
        740                 745                 750

Glu Leu Lys Lys Ala Phe Pro Glu Asn Ile Ser Lys Glu Arg Ser Leu
    755                 760                 765

Ile Asn Lys Asn Ile Pro Asn Leu Lys Trp Leu Ala Gly Phe Thr Ser
770                 775                 780

Gly Asp Gly Ser Phe Val Val Glu Leu Lys Lys Arg Arg Ser Pro Val
785                 790                 795                 800

Lys Val Gly Val Arg Leu Arg Phe Ser Ile Thr Gln His Ile Arg Asp
            805                 810                 815

Lys Asn Leu Met Asn Ser Leu Ile Thr Tyr Leu Gly Cys Gly Arg Ile
        820                 825                 830

Val Glu Asn Asn Lys Ser Glu His Ser Trp Leu Glu Phe Ile Val Thr
    835                 840                 845

Lys Phe Ser Asp Ile Asn Asp Lys Ile Ile Pro Val Phe Gln Glu Asn
850                 855                 860

Thr Leu Ile Gly Val Lys Leu Glu Asp Phe Glu Asp Trp Cys Lys Val
865                 870                 875                 880

Ala Lys Leu Ile Glu Glu Lys Lys His Leu Thr Glu Ser Gly Leu Asp
            885                 890                 895

Glu Ile Lys Lys Ile Lys Leu Asn Met Asn Lys Gly Arg Val Phe Ser
        900                 905                 910

Gly Arg

<210> SEQ ID NO 14
<211> LENGTH: 914
<212> TYPE: PRT
<213> ORGANISM: Artificial Sequence
<220> FEATURE:
<223> OTHER INFORMATION: Made in Lab - synthesized megaTAL CBLB.F6
      construct

<400> SEQUENCE: 14

Met Gly Ser Ala Pro Pro Lys Lys Arg Lys Val Val Asp Leu Arg
1               5                   10                  15

Thr Leu Gly Tyr Ser Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
                100                 105                 110

Leu Gln Leu Asp Thr Gly Gln Leu Val Lys Ile Ala Lys Arg Gly Gly
            115                 120                 125

Val Thr Ala Met Glu Ala Val His Ala Ser Arg Asn Ala Leu Thr Gly
130                 135                 140

Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
210                 215                 220

Ile Ala Ser Asn Gly Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Gly Lys Gln Ala Leu Glu Thr Val
            260                 265                 270

Gln Arg Leu Leu Pro Val Leu Cys Gln Asp His Gly Leu Thr Pro Asp
        275                 280                 285

Gln Val Val Ala Ile Ala Ser Asn Ile Gly Gly Lys Gln Ala Leu Glu
    290                 295                 300

Thr Val Gln Arg Leu Leu Pro Val Leu Cys Gln Asp His Gly Leu Thr
305                 310                 315                 320

Pro Asp Gln Val Val Ala Ile Ala Ser Asn Gly Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Asn Gly Gly Lys
        355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Ile Gly
385                 390                 395                 400

Gly Lys Gln Ala Leu Glu Thr Val Gln Arg Leu Leu Pro Val Leu Cys

-continued

```
                405                 410                 415
Gln Asp His Gly Leu Thr Pro Asp Gln Val Ala Ile Ala Ser Asn
            420                 425                 430

Asn Gly Gly Lys Gln Ala Leu Glu Thr Val Gln Arg Leu Leu Pro Val
            435                 440                 445

Leu Cys Gln Asp His Gly Leu Thr Pro Asp Gln Val Ala Ile Ala
            450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Ala
            485                 490                 495

Ile Ala Ser Asn Gly Gly Lys Gln Ala Leu Glu Thr Val Gln Arg
            500                 505                 510

Leu Leu Pro Val Leu Cys Gln Asp His Gly Leu Thr Pro Asp Gln Val
            515                 520                 525

Val Ala Ile Ala Ser Asn Ile Gly Gly Lys Gln Ala Leu Glu Ser Ile
            530                 535                 540

Val Ala Gln Leu Ser Arg Pro Asp Pro Ala Leu Ala Ala Leu Thr Asn
545                 550                 555                 560

Asp His Leu Val Ala Leu Ala Cys Leu Gly Gly Arg Pro Ala Met Asp
                565                 570                 575

Ala Val Lys Lys Gly Leu Pro His Ala Pro Glu Leu Ile Arg Arg Val
            580                 585                 590

Asn Arg Arg Ile Gly Glu Arg Thr Ser His Arg Val Ala Ile Ser Arg
            595                 600                 605

Val Gly Gly Ser Ser Arg Arg Glu Ser Ile Asn Pro Trp Ile Leu Thr
            610                 615                 620

Gly Phe Ala Asp Ala Glu Gly Cys Phe Arg Leu Asp Ile Arg Asn Ala
625                 630                 635                 640

Asn Asp Leu Arg Ala Gly Tyr Arg Thr Arg Leu Ala Phe Glu Ile Val
                645                 650                 655

Leu His Asn Lys Asp Lys Ser Ile Leu Glu Asn Ile Gln Ser Thr Trp
            660                 665                 670

Lys Val Gly Thr Ile Tyr Asn Ala Gly Asp Asn Ala Val Arg Leu Gln
            675                 680                 685

Val Thr Arg Phe Glu Asp Leu Lys Val Ile Asp His Phe Glu Lys
            690                 695                 700

Tyr Pro Leu Ile Thr Gln Lys Leu Gly Asp Tyr Lys Leu Phe Lys Gln
705                 710                 715                 720

Ala Phe Ser Val Met Glu Asn Lys Glu His Leu Lys Glu Asn Gly Ile
                725                 730                 735

Lys Glu Leu Val Arg Ile Lys Ala Lys Met Asn Trp Gly Leu Asn Asp
            740                 745                 750

Glu Leu Lys Lys Ala Phe Pro Glu Asn Ile Ser Lys Glu Arg Pro Leu
            755                 760                 765

Ile Asn Lys Asn Ile Pro Asn Leu Lys Trp Leu Ala Gly Phe Thr Ser
            770                 775                 780

Gly Asp Gly Ser Phe Met Val Glu Leu Met Lys Asn Lys Asn Val
785                 790                 795                 800

Ile Val Arg Val Arg Leu Arg Phe Ser Ile Ser Gln His Ile Arg Asp
                805                 810                 815

Lys Asn Leu Met Asn Ser Leu Ile Thr Tyr Leu Gly Cys Gly Arg Ile
            820                 825                 830
```

Val Glu Asn Asn Lys Ser Glu His Ser Trp Leu Glu Phe Ile Val Thr
            835                 840                 845

Lys Phe Ser Asp Ile Asn Asp Lys Ile Ile Pro Val Phe Gln Glu Asn
        850                 855                 860

Thr Leu Ile Gly Val Lys Leu Glu Asp Phe Glu Asp Trp Cys Lys Val
865                 870                 875                 880

Ala Lys Leu Ile Glu Glu Lys His Leu Thr Glu Ser Gly Leu Asp
            885                 890                 895

Glu Ile Lys Lys Ile Lys Leu Asn Met Asn Lys Gly Arg Val Phe Ser
            900                 905                 910

Gly Arg

<210> SEQ ID NO 15
<211> LENGTH: 914
<212> TYPE: PRT
<213> ORGANISM: Artificial Sequence
<220> FEATURE:
<223> OTHER INFORMATION: Made in Lab - synthesized megaTAL CBLB.E6
      construct

<400> SEQUENCE: 15

Met Gly Ser Ala Pro Pro Lys Lys Lys Arg Lys Val Val Asp Leu Arg
1               5                   10                  15

Thr Leu Gly Tyr Ser Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

Val Thr Ala Met Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
    210                 215                 220

Ile Ala Ser Asn Gly Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Gly Lys Gln Ala Leu Glu Thr Val
            260                 265                 270

-continued

```
Gln Arg Leu Leu Pro Val Leu Cys Gln Asp His Gly Leu Thr Pro Asp
            275                 280                 285

Gln Val Val Ala Ile Ala Ser Asn Ile Gly Gly Lys Gln Ala Leu Glu
        290                 295                 300

Thr Val Gln Arg Leu Leu Pro Val Leu Cys Gln Asp His Gly Leu Thr
305                 310                 315                 320

Pro Asp Gln Val Val Ala Ile Ala Ser Asn Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Asn Gly Gly Lys
        355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Ile Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Asn Gly Gly Lys Gln Ala Leu Glu Thr Val Gln Arg Leu Leu Pro Val
        435                 440                 445

Leu Cys Gln Asp His Gly Leu Thr Pro Asp Gln Val Val Ala Ile Ala
    450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Gly Gly Gly Lys Gln Ala Leu Glu Thr Val Gln Arg
            500                 505                 510

Leu Leu Pro Val Leu Cys Gln Asp His Gly Leu Thr Pro Asp Gln Val
        515                 520                 525

Val Ala Ile Ala Ser Asn Ile Gly Gly Lys Gln Ala Leu Glu Ser Ile
    530                 535                 540

Val Ala Gln Leu Ser Arg Pro Asp Pro Ala Leu Ala Ala Leu Thr Asn
545                 550                 555                 560

Asp His Leu Val Ala Leu Ala Cys Leu Gly Gly Arg Pro Ala Met Asp
                565                 570                 575

Ala Val Lys Lys Gly Leu Pro His Ala Pro Glu Leu Ile Arg Arg Val
            580                 585                 590

Asn Arg Arg Ile Gly Glu Arg Thr Ser His Arg Val Ala Ile Ser Arg
        595                 600                 605

Val Gly Gly Ser Ser Arg Arg Glu Ser Ile Asn Pro Trp Ile Leu Thr
    610                 615                 620

Gly Phe Ala Asp Ala Glu Gly Cys Phe Arg Leu Asp Ile Arg Asn Ala
625                 630                 635                 640

Asn Asp Leu Arg Ala Gly Tyr Arg Thr Arg Leu Ser Phe Glu Ile Ser
                645                 650                 655

Leu His Asn Lys Asp Lys Ser Ile Leu Glu Asn Ile Gln Ser Thr Trp
            660                 665                 670

Lys Val Gly Thr Ile Tyr Asn Ala Gly Asp Asn Ala Val Arg Leu Gln
        675                 680                 685
```

-continued

Val Thr Arg Phe Glu Asp Leu Lys Val Ile Ile Asp His Phe Glu Lys
690                 695                 700

Tyr Pro Leu Ile Thr Gln Lys Leu Gly Asp Tyr Lys Leu Phe Lys Gln
705                 710                 715                 720

Ala Phe Ser Val Met Glu Asn Lys Glu His Leu Lys Glu Asn Gly Ile
            725                 730                 735

Lys Glu Leu Val Arg Ile Lys Ala Lys Met Asn Trp Gly Leu Asn Asp
            740                 745                 750

Glu Leu Lys Lys Ala Phe Pro Glu Asn Ile Ser Lys Glu Arg Pro Leu
        755                 760                 765

Ile Asn Lys Asn Ile Pro Asn Leu Lys Trp Leu Ala Gly Phe Thr Ser
770                 775                 780

Gly Asp Gly Ser Phe Met Val Glu Leu Met Lys Asn Lys Asn Asn Val
785                 790                 795                 800

Ile Val Arg Val Arg Leu Arg Phe Ser Ile Ser Gln His Ile Arg Asp
                805                 810                 815

Lys Asn Leu Met Asn Ser Leu Ile Thr Tyr Leu Gly Cys Gly Arg Ile
            820                 825                 830

Val Glu Asn Asn Lys Ser Glu His Ser Trp Leu Glu Phe Ile Val Thr
835                 840                 845

Lys Phe Ser Asp Ile Asn Asp Lys Ile Ile Pro Val Phe Gln Glu Asn
850                 855                 860

Thr Leu Ile Gly Val Lys Leu Glu Asp Phe Glu Asp Trp Cys Lys Val
865                 870                 875                 880

Ala Lys Leu Ile Glu Glu Lys Lys His Leu Thr Glu Ser Gly Leu Asp
                885                 890                 895

Glu Ile Lys Lys Ile Lys Leu Asn Met Asn Lys Gly Arg Val Phe Ser
        900                 905                 910

Gly Arg

<210> SEQ ID NO 16
<211> LENGTH: 914
<212> TYPE: PRT
<213> ORGANISM: Artificial Sequence
<220> FEATURE:
<223> OTHER INFORMATION: Made in Lab - synthesized megaTAL CBLB.D2
      construct

<400> SEQUENCE: 16

Met Gly Ser Ala Pro Pro Lys Lys Arg Lys Val Val Asp Leu Arg
1               5                   10                  15

Thr Leu Gly Tyr Ser Gln Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

```
Val Thr Ala Met Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
    210                 215                 220

Ile Ala Ser Asn Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Lys Gln Ala Leu Glu Thr Val
            260                 265                 270

Gln Arg Leu Leu Pro Val Leu Cys Gln Asp His Gly Leu Thr Pro Asp
        275                 280                 285

Gln Val Val Ala Ile Ala Ser Asn Ile Gly Gly Lys Gln Ala Leu Glu
    290                 295                 300

Thr Val Gln Arg Leu Leu Pro Val Leu Cys Gln Asp His Gly Leu Thr
305                 310                 315                 320

Pro Asp Gln Val Val Ala Ile Ala Ser Asn Gly Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Asn Gly Gly Lys
        355                 360                 365

Gln Ala Leu Glu Thr Val Gln Arg Leu Leu Pro Val Leu Cys Gln Asp
    370                 375                 380

His Gly Leu Thr Pro Asp Gln Val Val Ala Ile Ala Ser Asn Ile Gly
385                 390                 395                 400

Gly Lys Gln Ala Leu Glu Thr Val Gln Arg Leu Leu Pro Val Leu Cys
                405                 410                 415

Gln Asp His Gly Leu Thr Pro Asp Gln Val Val Ala Ile Ala Ser Asn
            420                 425                 430

Asn Gly Gly Lys Gln Ala Leu Glu Thr Val Gln Arg Leu Leu Pro Val
        435                 440                 445

Leu Cys Gln Asp His Gly Leu Thr Pro Asp Gln Val Val Ala Ile Ala
    450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Gly Gly Gly Lys Gln Ala Leu Glu Thr Val Gln Arg
            500                 505                 510

Leu Leu Pro Val Leu Cys Gln Asp His Gly Leu Thr Pro Asp Gln Val
        515                 520                 525

Val Ala Ile Ala Ser Asn Ile Gly Gly Lys Gln Ala Leu Glu Ser Ile
    530                 535                 540

Val Ala Gln Leu Ser Arg Pro Asp Pro Ala Leu Ala Ala Leu Thr Asn
```

```
            545                 550                 555                 560
Asp His Leu Val Ala Leu Ala Cys Leu Gly Gly Arg Pro Ala Met Asp
                565                 570                 575

Ala Val Lys Lys Gly Leu Pro His Ala Pro Glu Leu Ile Arg Arg Val
            580                 585                 590

Asn Arg Arg Ile Gly Glu Arg Thr Ser His Arg Val Ala Ile Ser Arg
        595                 600                 605

Val Gly Gly Ser Ser Arg Arg Glu Ser Ile Asn Pro Trp Ile Leu Thr
    610                 615                 620

Gly Phe Ala Asp Ala Glu Gly Cys Phe Arg Leu Asp Ile His Asn Ala
625                 630                 635                 640

Asn Val Leu Arg Ser Gly Tyr Arg Thr Arg Leu Ser Phe Glu Ile Val
                645                 650                 655

Leu His Asn Lys Asp Lys Ser Ile Leu Glu Asn Ile Gln Ser Thr Trp
            660                 665                 670

Lys Val Gly Lys Ile Tyr Asn Ala Gly Asp Asn Ala Val Arg Leu Gln
        675                 680                 685

Val Thr Arg Phe Glu Asp Leu Lys Val Ile Ile Asp His Phe Glu Lys
    690                 695                 700

Tyr Pro Leu Ile Thr Gln Lys Leu Gly Asp Tyr Lys Leu Phe Lys Gln
705                 710                 715                 720

Ala Phe Ser Val Met Glu Asn Lys Glu His Leu Lys Glu Asn Gly Ile
                725                 730                 735

Lys Glu Leu Val Arg Ile Lys Ala Lys Met Asn Trp Gly Leu Asn Asp
            740                 745                 750

Glu Leu Lys Lys Ala Phe Pro Glu Asn Ile Ser Lys Glu Arg Pro Leu
        755                 760                 765

Ile Asn Lys Asn Ile Pro Asn Leu Lys Trp Leu Ala Gly Phe Thr Ser
    770                 775                 780

Gly Asp Gly Ser Phe Met Val Glu Leu Met Lys Asn Lys Asn Asn Val
785                 790                 795                 800

Ile Val Arg Val Arg Leu Arg Phe Ser Ile Ser Gln His Ile Arg Asp
                805                 810                 815

Lys Asn Leu Met Asn Ser Leu Ile Thr Tyr Leu Gly Cys Gly Arg Ile
            820                 825                 830

Val Glu Asn Asn Lys Ser Glu His Ser Trp Leu Glu Phe Ile Val Thr
        835                 840                 845

Lys Phe Ser Asp Ile Asn Asp Lys Ile Ile Pro Val Phe Gln Glu Asn
    850                 855                 860

Thr Leu Ile Gly Val Lys Leu Glu Asp Phe Glu Asp Trp Cys Lys Val
865                 870                 875                 880

Ala Lys Leu Ile Glu Glu Lys Lys His Leu Thr Glu Ser Gly Leu Asp
                885                 890                 895

Glu Ile Lys Lys Ile Lys Leu Asn Met Asn Lys Gly Arg Val Phe Ser
            900                 905                 910

Gly Arg

<210> SEQ ID NO 17
<211> LENGTH: 914
<212> TYPE: PRT
<213> ORGANISM: Artificial Sequence
<220> FEATURE:
<223> OTHER INFORMATION: Made in Lab - synthesized megaTAL CBLB.C2
      construct
```

<400> SEQUENCE: 17

```
Met Gly Ser Ala Pro Pro Lys Lys Arg Lys Val Val Asp Leu Arg
 1               5                  10                  15

Thr Leu Gly Tyr Ser Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

Val Thr Ala Met Glu Ala Val His Ala Ser Arg Asn Ala Leu Thr Gly
130                 135                 140

Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
210                 215                 220

Ile Ala Ser Asn Gly Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Gly Lys Gln Ala Leu Glu Thr Val
            260                 265                 270

Gln Arg Leu Leu Pro Val Leu Cys Gln Asp His Gly Leu Thr Pro Asp
        275                 280                 285

Gln Val Val Ala Ile Ala Ser Asn Ile Gly Gly Lys Gln Ala Leu Glu
290                 295                 300

Thr Val Gln Arg Leu Leu Pro Val Leu Cys Gln Asp His Gly Leu Thr
305                 310                 315                 320

Pro Asp Gln Val Val Ala Ile Ala Ser Asn Gly Gly Gly Lys Gln Ala
                325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Asn Gly Gly Lys
        355                 360                 365

Gln Ala Leu Glu Thr Val Gln Arg Leu Leu Pro Val Leu Cys Gln Asp
370                 375                 380

His Gly Leu Thr Pro Asp Gln Val Val Ala Ile Ala Ser Asn Ile Gly
385                 390                 395                 400

Gly Lys Gln Ala Leu Glu Thr Val Gln Arg Leu Leu Pro Val Leu Cys
                405                 410                 415
```

```
Gln Asp His Gly Leu Thr Pro Asp Gln Val Val Ala Ile Ala Ser Asn
            420                 425                 430

Asn Gly Gly Lys Gln Ala Leu Glu Thr Val Gln Arg Leu Leu Pro Val
        435                 440                 445

Leu Cys Gln Asp His Gly Leu Thr Pro Asp Gln Val Val Ala Ile Ala
450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
                485                 490                 495

Ile Ala Ser Asn Gly Gly Lys Gln Ala Leu Glu Thr Val Gln Arg
            500                 505                 510

Leu Leu Pro Val Leu Cys Gln Asp His Gly Leu Thr Pro Asp Gln Val
        515                 520                 525

Val Ala Ile Ala Ser Asn Ile Gly Gly Lys Gln Ala Leu Glu Ser Ile
530                 535                 540

Val Ala Gln Leu Ser Arg Pro Asp Pro Ala Leu Ala Ala Leu Thr Asn
545                 550                 555                 560

Asp His Leu Val Ala Leu Ala Cys Leu Gly Gly Arg Pro Ala Met Asp
                565                 570                 575

Ala Val Lys Lys Gly Leu Pro His Ala Pro Glu Leu Ile Arg Arg Val
            580                 585                 590

Asn Arg Arg Ile Gly Glu Arg Thr Ser His Arg Val Ala Ile Ser Arg
        595                 600                 605

Val Gly Gly Ser Ser Arg Arg Glu Ser Ile Asn Pro Trp Ile Leu Thr
            610                 615                 620

Gly Phe Ala Asp Ala Glu Gly Cys Phe Gly Leu Tyr Ile His Asn Ser
625                 630                 635                 640

Asn Val Leu Arg Ser Gly Tyr Arg Thr Arg Leu Ser Phe Glu Ile Ser
                645                 650                 655

Leu His Asn Lys Asp Lys Ser Ile Leu Glu Asn Ile Gln Ser Thr Trp
            660                 665                 670

Lys Val Gly Thr Ile Tyr Asn Ala Gly Asp Asn Ala Val Arg Leu Gln
        675                 680                 685

Val Thr Arg Phe Glu Asp Leu Lys Val Ile Asp His Phe Glu Lys
690                 695                 700

Tyr Pro Leu Ile Thr Gln Lys Leu Gly Asp Tyr Lys Leu Phe Lys Gln
705                 710                 715                 720

Ala Phe Ser Leu Met Glu Asn Lys Glu His Leu Lys Glu Asn Gly Ile
                725                 730                 735

Lys Glu Leu Val Arg Ile Lys Ala Lys Met Asn Trp Gly Leu Asn Asp
            740                 745                 750

Glu Leu Lys Lys Ala Phe Pro Glu Asn Ile Ser Lys Glu Arg Pro Leu
        755                 760                 765

Ile Asn Lys Asn Ile Pro Asn Leu Lys Trp Leu Ala Gly Phe Thr Ser
            770                 775                 780

Gly Asp Gly Ser Phe Met Val Glu Leu Met Lys Asn Lys Asn Val
785                 790                 795                 800

Ile Val Arg Val Arg Leu Arg Phe Ser Ile Ser Gln His Ile Arg Asp
                805                 810                 815

Lys Asn Leu Met Asn Ser Leu Ile Thr Tyr Leu Gly Cys Gly Arg Ile
            820                 825                 830
```

-continued

```
Val Glu Asn Asn Lys Ser Glu His Ser Trp Leu Glu Phe Ile Val Thr
            835                 840                 845

Lys Phe Ser Asp Ile Asn Asp Lys Ile Ile Pro Val Phe Gln Glu Asn
850                 855                 860

Thr Leu Ile Gly Val Lys Leu Glu Asp Phe Glu Asp Trp Cys Lys Val
865                 870                 875                 880

Ala Lys Leu Ile Glu Glu Lys His Leu Thr Glu Ser Gly Leu Asp
                885                 890                 895

Glu Ile Lys Lys Ile Lys Leu Asn Met Asn Lys Gly Arg Val Phe Ser
                900                 905                 910

Gly Arg

<210> SEQ ID NO 18
<211> LENGTH: 914
<212> TYPE: PRT
<213> ORGANISM: Artificial Sequence
<220> FEATURE:
<223> OTHER INFORMATION: Made in Lab - synthesized megaTAL CBLB.B5
      construct

<400> SEQUENCE: 18

Met Gly Ser Ala Pro Pro Lys Lys Arg Lys Val Val Asp Leu Arg
1               5                   10                  15

Thr Leu Gly Tyr Ser Gln Gln Gln Glu Lys Ile Lys Pro Lys Val
                20                  25                  30

Arg Ser Thr Val Ala Gln His His Glu Ala Leu Val Gly His Gly Phe
            35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

Val Thr Ala Met Glu Ala Val His Ala Ser Arg Asn Ala Leu Thr Gly
    130                 135                 140

Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
        195                 200                 205

Pro Val Leu Cys Gln Asp His Gly Leu Thr Pro Asp Gln Val Val Ala
    210                 215                 220

Ile Ala Ser Asn Gly Gly Gly Lys Gln Ala Leu Glu Thr Val Gln Arg
225                 230                 235                 240

Leu Leu Pro Val Leu Cys Gln Asp His Gly Leu Thr Pro Asp Gln Val
                245                 250                 255

Val Ala Ile Ala Ser Asn Gly Gly Gly Lys Gln Ala Leu Glu Thr Val
            260                 265                 270
```

```
Gln Arg Leu Leu Pro Val Leu Cys Gln Asp His Gly Leu Thr Pro Asp
            275                 280                 285
Gln Val Val Ala Ile Ala Ser Asn Ile Gly Gly Lys Gln Ala Leu Glu
        290                 295                 300
Thr Val Gln Arg Leu Leu Pro Val Leu Cys Gln Asp His Gly Leu Thr
305                 310                 315                 320
Pro Asp Gln Val Val Ala Ile Ala Ser Asn Gly Gly Lys Gln Ala
                325                 330                 335
Leu Glu Thr Val Gln Arg Leu Leu Pro Val Leu Cys Gln Asp His Gly
                340                 345                 350
Leu Thr Pro Asp Gln Val Val Ala Ile Ala Ser Asn Asn Gly Gly Lys
            355                 360                 365
Gln Ala Leu Glu Thr Val Gln Arg Leu Leu Pro Val Leu Cys Gln Asp
        370                 375                 380
His Gly Leu Thr Pro Asp Gln Val Val Ala Ile Ala Ser Asn Ile Gly
385                 390                 395                 400
Gly Lys Gln Ala Leu Glu Thr Val Gln Arg Leu Leu Pro Val Leu Cys
                405                 410                 415
Gln Asp His Gly Leu Thr Pro Asp Gln Val Val Ala Ile Ala Ser Asn
            420                 425                 430
Asn Gly Gly Lys Gln Ala Leu Glu Thr Val Gln Arg Leu Leu Pro Val
        435                 440                 445
Leu Cys Gln Asp His Gly Leu Thr Pro Asp Gln Val Val Ala Ile Ala
    450                 455                 460
Ser Asn Asn Gly Gly Lys Gln Ala Leu Glu Thr Val Gln Arg Leu Leu
465                 470                 475                 480
Pro Val Leu Cys Gln Asp His Gly Leu Thr Pro Asp Gln Val Val Ala
                485                 490                 495
Ile Ala Ser Asn Gly Gly Gly Lys Gln Ala Leu Glu Thr Val Gln Arg
            500                 505                 510
Leu Leu Pro Val Leu Cys Gln Asp His Gly Leu Thr Pro Asp Gln Val
        515                 520                 525
Val Ala Ile Ala Ser Asn Ile Gly Gly Lys Gln Ala Leu Glu Ser Ile
    530                 535                 540
Val Ala Gln Leu Ser Arg Pro Asp Pro Ala Leu Ala Ala Leu Thr Asn
545                 550                 555                 560
Asp His Leu Val Ala Leu Ala Cys Leu Gly Gly Arg Pro Ala Met Asp
                565                 570                 575
Ala Val Lys Lys Gly Leu Pro His Ala Pro Glu Leu Ile Arg Arg Val
            580                 585                 590
Asn Arg Arg Ile Gly Glu Arg Thr Ser His Arg Val Ala Ile Ser Arg
        595                 600                 605
Val Gly Gly Ser Ser Arg Arg Glu Ser Ile Asn Pro Trp Ile Leu Thr
    610                 615                 620
Gly Phe Ala Asp Ala Glu Gly Cys Phe Arg Leu Asp Ile His Asn Ala
625                 630                 635                 640
Asn Val Leu Arg Ser Gly Tyr Arg Thr Arg Leu Ser Phe Glu Ile Val
                645                 650                 655
Leu His Asn Lys Asp Lys Ser Ile Leu Glu Asn Ile Gln Ser Thr Trp
            660                 665                 670
Lys Val Gly Thr Ile Tyr Asn Ala Gly Asp Asn Ala Val Arg Leu Gln
        675                 680                 685
Val Thr Arg Phe Glu Asp Leu Lys Val Ile Ile Asp His Phe Glu Lys
```

```
                690             695             700
Tyr Pro Leu Ile Thr Gln Lys Leu Gly Asp Tyr Lys Leu Phe Lys Gln
705                 710             715                 720

Ala Phe Ser Leu Met Glu Asn Lys Glu His Leu Lys Glu Asn Gly Ile
                725             730                 735

Lys Glu Leu Val Arg Ile Lys Ala Lys Met Asn Trp Gly Leu Asn Asp
            740             745                 750

Glu Leu Lys Lys Ala Phe Pro Glu Asn Ile Ser Lys Glu Arg Pro Leu
            755             760                 765

Ile Asn Lys Asn Ile Pro Asn Leu Lys Trp Leu Ala Gly Phe Thr Ser
            770             775             780

Gly Asp Gly Ser Phe Val Val Glu Leu Lys Lys Arg Arg Ser Pro Val
785             790             795                 800

Lys Val Gly Val Arg Leu Arg Phe Gly Ile Thr Gln His Ile Arg Asp
                805             810              815

Lys Asn Leu Met Asn Ser Leu Ile Thr Tyr Leu Gly Cys Gly Arg Ile
                820             825             830

Val Glu Asn Asn Lys Ser Glu His Ser Trp Leu Glu Phe Ile Val Thr
            835             840             845

Lys Phe Ser Asp Ile Asn Asp Lys Ile Ile Pro Val Phe Gln Glu Asn
850             855             860

Thr Leu Ile Gly Val Lys Leu Glu Asp Phe Glu Asp Trp Cys Lys Val
865             870             875             880

Ala Lys Leu Ile Glu Glu Lys His Leu Thr Glu Ser Gly Leu Asp
                885             890             895

Glu Ile Lys Lys Ile Lys Leu Asn Met Asn Lys Gly Arg Val Phe Ser
                900             905             910

Gly Arg

<210> SEQ ID NO 19
<211> LENGTH: 914
<212> TYPE: PRT
<213> ORGANISM: Artificial Sequence
<220> FEATURE:
<223> OTHER INFORMATION: Made in Lab - synthesized megaTAL CBLB.A8
      construct

<400> SEQUENCE: 19

Met Gly Ser Ala Pro Pro Lys Lys Lys Arg Lys Val Val Asp Leu Arg
1               5                   10                  15

Thr Leu Gly Tyr Ser Gln Gln Gln Gln Glu Lys Ile Lys Pro Lys Val
            20                  25                  30

Arg Ser Thr Val Ala Gln His His Glu Ala Leu Val Gly His Gly Phe
        35                  40                  45

Thr His Ala His Ile Val Ala Leu Ser Gln His Pro Ala Ala Leu Gly
    50                  55                  60

Thr Val Ala Val Thr Tyr Gln His Ile Ile Thr Ala Leu Pro Glu Ala
65                  70                  75                  80

Thr His Glu Asp Ile Val Gly Val Gly Lys Gln Trp Ser Gly Ala Arg
                85                  90                  95

Ala Leu Glu Ala Leu Leu Thr Asp Ala Gly Glu Leu Arg Gly Pro Pro
            100                 105                 110

Leu Gln Leu Asp Thr Gly Gln Leu Val Lys Ile Ala Lys Arg Gly Gly
        115                 120                 125

Val Thr Ala Met Glu Ala Val His Ala Ser Arg Asn Ala Leu Thr Gly
```

```
            130                 135                 140
Ala Pro Leu Asn Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
            165                 170                 175

Leu Cys Gln Asp His Gly Leu Thr Pro Asp Gln Val Val Ala Ile Ala
            180                 185                 190

Ser Asn Asn Gly Gly Lys Gln Ala Leu Glu Thr Val Gln Arg Leu Leu
            195                 200                 205

Pro Val Leu Cys Gln Asp His Gly Leu Thr Pro Asp Gln Val Val Ala
210                 215                 220

Ile Ala Ser Asn Gly Gly Lys Gln Ala Leu Glu Thr Val Gln Arg
225                 230                 235                 240

Leu Leu Pro Val Leu Cys Gln Asp His Gly Leu Thr Pro Asp Gln Val
            245                 250                 255

Val Ala Ile Ala Ser Asn Gly Gly Lys Gln Ala Leu Glu Thr Val
            260                 265                 270

Gln Arg Leu Leu Pro Val Leu Cys Gln Asp His Gly Leu Thr Pro Asp
            275                 280                 285

Gln Val Val Ala Ile Ala Ser Asn Ile Gly Gly Lys Gln Ala Leu Glu
            290                 295                 300

Thr Val Gln Arg Leu Leu Pro Val Leu Cys Gln Asp His Gly Leu Thr
305                 310                 315                 320

Pro Asp Gln Val Val Ala Ile Ala Ser Asn Gly Gly Lys Gln Ala
            325                 330                 335

Leu Glu Thr Val Gln Arg Leu Leu Pro Val Leu Cys Gln Asp His Gly
            340                 345                 350

Leu Thr Pro Asp Gln Val Val Ala Ile Ala Ser Asn Asn Gly Gly Lys
            355                 360                 365

Gln Ala Leu Glu Thr Val Gln Arg Leu Leu Pro Val Leu Cys Gln Asp
370                 375                 380

His Gly Leu Thr Pro Asp Gln Val Val Ala Ile Ala Ser Asn Ile Gly
385                 390                 395                 400

Gly Lys Gln Ala Leu Glu Thr Val Gln Arg Leu Leu Pro Val Leu Cys
            405                 410                 415

Gln Asp His Gly Leu Thr Pro Asp Gln Val Val Ala Ile Ala Ser Asn
            420                 425                 430

Asn Gly Gly Lys Gln Ala Leu Glu Thr Val Gln Arg Leu Leu Pro Val
            435                 440                 445

Leu Cys Gln Asp His Gly Leu Thr Pro Asp Gln Val Val Ala Ile Ala
            450                 455                 460

Ser Asn Asn Gly Gly Lys Gln Ala Leu Glu Thr Val Gln Arg Leu Leu
465                 470                 475                 480

Pro Val Leu Cys Gln Asp His Gly Leu Thr Pro Asp Gln Val Val Ala
            485                 490                 495

Ile Ala Ser Asn Gly Gly Gly Lys Gln Ala Leu Glu Thr Val Gln Arg
            500                 505                 510

Leu Leu Pro Val Leu Cys Gln Asp His Gly Leu Thr Pro Asp Gln Val
            515                 520                 525

Val Ala Ile Ala Ser Asn Ile Gly Gly Lys Gln Ala Leu Glu Ser Ile
            530                 535                 540

Val Ala Gln Leu Ser Arg Pro Asp Pro Ala Leu Ala Ala Leu Thr Asn
545                 550                 555                 560
```

Asp His Leu Val Ala Leu Ala Cys Leu Gly Gly Arg Pro Ala Met Asp
565 570 575

Ala Val Lys Lys Gly Leu Pro His Ala Pro Glu Leu Ile Arg Arg Val
580 585 590

Asn Arg Arg Ile Gly Glu Arg Thr Ser His Arg Val Ala Ile Ser Arg
595 600 605

Val Gly Gly Ser Ser Arg Arg Glu Ser Ile Asn Pro Trp Ile Leu Thr
610 615 620

Gly Phe Ala Asp Ala Glu Gly Cys Phe Arg Leu Asp Ile Arg Asn Ala
625 630 635 640

Asn Asp Leu Arg Ala Gly Tyr Arg Thr Arg Leu Ala Phe Glu Ile Val
645 650 655

Leu His Asn Lys Asp Lys Ser Ile Leu Glu Asn Ile Gln Ser Thr Trp
660 665 670

Lys Val Gly Thr Ile Tyr Asn Ala Gly Asp Asn Ala Val Arg Leu Gln
675 680 685

Val Thr Arg Phe Glu Asp Leu Lys Val Ile Ile Gly His Phe Glu Lys
690 695 700

Tyr Pro Leu Ile Thr Gln Lys Leu Gly Asp Tyr Lys Leu Phe Lys Gln
705 710 715 720

Ala Phe Ser Val Met Glu Asn Lys Glu His Leu Lys Glu Asn Gly Ile
725 730 735

Lys Glu Leu Val Arg Ile Lys Ala Lys Met Asn Trp Gly Leu Asn Asp
740 745 750

Glu Leu Lys Lys Ala Phe Pro Glu Asn Ile Ser Lys Glu Arg Pro Leu
755 760 765

Ile Asn Lys Asn Ile Pro Asn Leu Lys Trp Leu Ala Gly Phe Thr Ser
770 775 780

Gly Asp Gly Ser Phe Met Val Glu Leu Met Lys Asn Lys Asn Asn Val
785 790 795 800

Ile Val Arg Val Arg Leu Arg Phe Ser Ile Ser Gln His Ile Arg Asp
805 810 815

Lys Asn Leu Met Asn Ser Leu Ile Thr Tyr Leu Gly Cys Gly Arg Ile
820 825 830

Val Glu Asn Asn Lys Ser Glu His Ser Trp Leu Glu Phe Ile Val Thr
835 840 845

Lys Phe Ser Asp Ile Asn Asp Lys Ile Ile Pro Val Phe Gln Glu Asn
850 855 860

Thr Leu Ile Gly Val Lys Leu Glu Asp Phe Glu Asp Trp Cys Lys Val
865 870 875 880

Ala Lys Leu Ile Glu Glu Lys Lys His Leu Thr Glu Ser Gly Leu Asp
885 890 895

Glu Ile Lys Lys Ile Lys Leu Asn Met Asn Lys Gly Arg Val Phe Ser
900 905 910

Gly Arg

<210> SEQ ID NO 20
<211> LENGTH: 22
<212> TYPE: DNA
<213> ORGANISM: Homo sapiens

<400> SEQUENCE: 20
ctgtaagata ttcccatccc ca 22

```
<210> SEQ ID NO 21
<211> LENGTH: 13
<212> TYPE: DNA
<213> ORGANISM: Homo sapiens

<400> SEQUENCE: 21
ttgttatgag gta                                                          13

<210> SEQ ID NO 22
<211> LENGTH: 39
<212> TYPE: DNA
<213> ORGANISM: Homo sapiens

<400> SEQUENCE: 22
ttgttatgag gtatggtctg taagatattc ccatcccca                              39

<210> SEQ ID NO 23
<211> LENGTH: 22
<212> TYPE: DNA
<213> ORGANISM: Homo sapiens

<400> SEQUENCE: 23
ctgtaagata ttcaaccttt ta                                                22

<210> SEQ ID NO 24
<211> LENGTH: 22
<212> TYPE: DNA
<213> ORGANISM: Homo sapiens

<400> SEQUENCE: 24
tttccactta ttcccatccc ca                                                22

<210> SEQ ID NO 25
<211> LENGTH: 22
<212> TYPE: DNA
<213> ORGANISM: Homo sapiens

<400> SEQUENCE: 25
ctgtaagata ttctacgtct gc                                                22

<210> SEQ ID NO 26
<211> LENGTH: 22
<212> TYPE: DNA
<213> ORGANISM: Homo sapiens

<400> SEQUENCE: 26
cttccaggaa ttcccatccc ca                                                22

<210> SEQ ID NO 27
<211> LENGTH: 22
<212> TYPE: DNA
<213> ORGANISM: Homo sapiens

<400> SEQUENCE: 27
ctgtaagata ttccacaggc tc                                                22

<210> SEQ ID NO 28
<211> LENGTH: 22
<212> TYPE: PRT
<213> ORGANISM: Homo sapiens

<400> SEQUENCE: 28

Thr Gly Thr Cys Cys Ala Ala Thr Ala Ala Thr Thr Cys Cys Cys Ala
```

```
1               5                   10                  15
Thr Cys Cys Cys Cys Ala
             20

<210> SEQ ID NO 29
<211> LENGTH: 22
<212> TYPE: DNA
<213> ORGANISM: Homo sapiens

<400> SEQUENCE: 29
ctgtaagata ttcaccgatt tt                                              22

<210> SEQ ID NO 30
<211> LENGTH: 7244
<212> TYPE: DNA
<213> ORGANISM: Artificial Sequence
<220> FEATURE:
<223> OTHER INFORMATION: Made in Lab - synthesized I-OnuI variant
      CBLB.E3 surface display plasmid

<400> SEQUENCE: 30
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
aaataaagaa ggtagaagag ttacggaatg aagaaaaaaa ataaacaaa ggtttaaaaa     240 atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atccccctag agtcttttac atcttcggaa aacaaaaact    480
atttttcctt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaaggaa gagtatgagt    720
attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg cgcggtatt ccccgtatt     960 gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt ttttcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
ggcagtcagg caactatgga tgaacgaaat agacagatcg ctgagatagg tgcctcactg   1560
attaagcatt ggtaactgtc agaccaagtt tactcatata tactttagat tgatttaaaa   1620
```

-continued

```
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atccttttt tctgcgcgta atctgctgct tgcaaacaaa aaaaccaccg   1800
ctaccagcgg tggtttgttt gccggatcaa gagctaccaa ctcttttcc gaaggtaact   1860 ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc caggggggaa cgcctggtat ctttatagtc ctgtcgggtt tcgccacctc   2280
tgacttgagc gtcgattttt gtgatgctcg tcaggggggc cgagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gctcggaatt   2760
aaccctcact aaagggaaca aaagctgggt accgacagg ttatcagcaa caacacagtc   2820
atatccattc tcaattagct ctaccacagt gtgtgaacca atgtatccag caccacctgt   2880
aaccaaaaca attttagaag tactttcact ttgtaactga gctgtcattt atattgaatt   2940
ttcaaaaatt cttactttt ttttggatgg acgcaaagaa gtttaataat catattacat   3000
ggcattacca ccatatacat atccatatac atatccatat ctaatcttac ttatatgttg   3060
tggaaatgta aagagcccca ttatcttagc ctaaaaaaac cttctctttg gaactttcag   3120
taatacgctt aactgctcat tgctatattg aagtacggat tagaagccgc cgagcgggtg   3180
acagccctcc gaaggaagac tctcctccgt gcgtcctcgt cttcaccggt cgcgttcctg   3240
aaacgcagat gtgcctcgcg ccgcactgct ccgaacaata aagattctac aatactagct   3300
tttatggtta tgaagaggaa aaattggcag taacctggcc ccacaaacct tcaaatgaac   3360
gaatcaaatt aacaaccata ggatgataat gcgattagtt ttttagcctt atttctgggg   3420
taattaatca gcgaagcgat gatttttgat ctattaacag atatataaat gcaaaaactg   3480
cataaccact ttaactaata ctttcaacat tttcggtttg tattacttct tattcaaatg   3540 taataaaga tcgaatccta cttcatacat tttcaattaa gatgcagtta cttcgctgtt   3600
tttcaatatt ttctgttatt gcttcagttt tagcacagga actgacaact atatgcgagc   3660
aaatcccctc accaacttta gaatcgacgc cgtactcttt gtcaacgact actattttgg   3720
ccaacgggaa ggcaatgcaa ggagtttttg aatattacaa atcagtaacg tttgtcagta   3780
attgcggttc tcaccctca acaactagca aaggcagccc cataaacaca cagtatgttt   3840
ttaaggacaa tagctcgacg attgaaggta gataccata cgacgttcca gactacgctc   3900
tgcaggctag tggtggagga ggctctggtg gaggcggtag cggaggcgga gggtcggcta   3960
```

```
gctccatcaa cccatggatt ctgactggtt tcgctgatgc cgaaggatgc ttccgactag    4020
acatccgcaa cgcaaacgat ttaagagccg gatacagaac tagactggcc ttcgaaatcg    4080
tactgcacaa caaggacaaa tcgattctgg agaatatcca gtcgacttgg aaggtcggca    4140
caatctacaa cgcgggcgac aacgcagtca gactgcaagt cacacgtttc gaagatttga    4200
aagtgattat cgaccacttc gagaaatatc cgctgataac acagaaattg ggcgattaca    4260
agttgtttaa acaggcattc agcgtcatgg agaacaaaga acatcttaag gagaatggga    4320
ttaaggagct cgtacgaatc aaagctaaga tgaattgggg tctcaatgac gaattgaaaa    4380
aagcatttcc agagaacatt agcaaagagc gctcccttat caataagaac attccgaatc    4440
tcaaatggct ggctggattc acatctggtg acggctcgtt cgtggtggaa ctaaagaaga    4500
gaagaagccc cgtcaaggta ggagtgcggc tgcgattcag catcacccag cacatcagag    4560
acaagaacct gatgaattca ttgataacat acctaggctg tggtcgtatc gttgagaata    4620
acaaatctga gcacagttgg ctcgaattca ttgtaacaaa attcagcgat atcaacgaca    4680
agatcattcc ggtattccag gaaaatactc tgattggcgt caaactcgag gactttgaag    4740
attggtgcaa ggttgccaaa ttgatcgaag agaagaaaca cctgaccgaa tccggtttgg    4800
atgagattaa gaaaatcaag ctgaacatga acaaggtcg tgtcttctct agaggcggtt    4860
ccagaagcgg atctggtact ggcgaacaga aactcataag cgaagaagac cttagcggga    4920
ctggagagca aaagttgatt tctgaggagg atttgtcggg aaccggggag cagaagttaa    4980
tcagtgaaga ggatctcagt ggaacgggcg aacaaaagtt gatctcggag gaagacttat    5040
aatgaagatc tgataacaac agtgtagatg taacaaaatc gactttgttc ccactgtact    5100
tttagctcgt acaaaataca atatactttt catttctccg taaacaacat gttttcccat    5160
gtaatatcct tttctatttt tcgttccgtt accaacttta cacatacttt atatagctat    5220
tcacttctat acactaaaaa actaagacaa ttttaatttt gctgcctgcc atatttcaat    5280
ttgttataaa ttcctataat ttatcctatt agtagctaaa aaaagatgaa tgtgaatcga    5340
atcctaagag aattgagctc caattcgccc tatagtgagt cgtattacaa ttcactggcc    5400
gtcgttttac aacgtcgtga ctgggaaaac cctggcgtta cccaacttaa tcgccttgca    5460
gcacatcccc ctttcgccag ctggcgtaat agcgaagagg cccgcaccga tcgcctttcc    5520
caacagttgc gcagcctgaa tggcgaatgg acgcgccctg tagcggcgca ttaagcgcgg    5580
cgggtgtggt ggttacgcgc agcgtgaccg ctacacttgc cagcgcccta gcgcccgctc    5640
cttccgcttt cttcccttcc tttctcgcca cgttcgccgg ctttccccgt caagctctaa    5700
atcgggggct ccctttaggg ttccgattta gtgctttacg gcacctcgac cccaaaaaac    5760
ttgattaggg tgatggttca cgtagtgggc catcgccctg atagacggtt tttcgccctt    5820
tgacgttgga gtccacgttc tttaatagtg gactcttgtt ccaaactgga acaacactca    5880
accctatctc ggtctattct tttgatttat aagggatttt gccgatttcg gcctattggt    5940
taaaaaatga gctgatttaa caaaaattta acgcgaattt taacaaaata ttaacgttta    6000
caatttcctg atgcggtatt ttctccttac gcatctgtgc ggtatttcac accgcaggca    6060
agtgcacaaa caatacttaa ataaatacta ctcagtaata acctatttct tagcattttt    6120
gacgaaattt gctattttgt tagagtcttt tacaccattt gtctccacac ctccgcttac    6180
atcaacacca ataacgccat ttaatctaag cgcatcacca acattttctg gcgtcagtcc    6240
accagctaac ataaaatgta agctttcggg gctctcttgc cttccaaccc agtcagaaat    6300
cgagttccaa tccaaaagtt cacctgtccc acctgcttct gaatcaaaca agggaataaa    6360
```

```
cgaatgaggt ttctgtgaag ctgcactgag tagtatgttg cagtcttttg gaaatacgag    6420
tcttttaata actggcaaac cgaggaactc ttggtattct tgccacgact catctccatg    6480
cagttggacg acatcaatgc cgtaatcatt gaccagagcc aaaacatcct ccttaggttg    6540
attacgaaac acgccaacca agtatttcgg agtgcctgaa ctattttat atgcttttac     6600 aagacttgaa attttccttg caataaccgg gtcaattgtt ctctttctat tgggcacaca    6660
tataataccc agcaagtcag catcggaatc aagagcacat tctgcggcct ctgtgctctg    6720
caagccgcaa actttcacca atggaccaga actacctgtg aaattaataa cagacatact    6780
ccaagctgcc tttgtgtgct taatcacgta tactcacgtg ctcaatagtc accaatgccc    6840
tccctcttgg ccctctcctt ttcttttttc gaccgaatta attcttaatc ggcaaaaaaa    6900
gaaaagctcc ggatcaagat tgtacgtaag gtgacaagct attttcaat aaagaatatc     6960 ttccactact gccatctggc gtcataactg caaagtacac atatattacg atgctgtcta    7020
ttaaatgctt cctatattat atatatagta atgtcgttta tggtgcactc tcagtacaat    7080
ctgctctgat gccgcatagt taagccagcc ccgacacccg ccaacacccg ctgacgcgcc    7140
ctgacgggct tgtctgctcc cggcatccgc ttacagacaa gctgtgaccg tctccgggag    7200
ctgcatgtgt cagaggtttt caccgtcatc accgaaacgc gcga                    7244
```

<210> SEQ ID NO 31
<211> LENGTH: 2748
<212> TYPE: RNA
<213> ORGANISM: Artificial Sequence
<220> FEATURE:
<223> OTHER INFORMATION: Made in Lab - synthesized megaTAL CBLB.E3 mRNA

<400> SEQUENCE: 31

```
augggauccg cgccaccuaa gaagaaacgc aaagucgugg aucuacgcac gcucggcuac      60
agucagcagc agcaagagaa gaucaaaccg aaggugcguu cgacaguggc gcagcaccac    120
gaggcacugg ugggccaugg guuuacacac gcgcacaucg uugcgcucag ccaacacccg    180
gcagcguuag ggaccgucgc ugucacguau cagcacauaa ucacggcguu gccagaggcg    240
acacacgaag acaucguugg cgucggcaaa cagguguccg gcgcacgcgc ccuggaggcc    300
uugcucacgg augcggggga guugagaggu ccgccguuac aguuggacac aggccaacuu    360
gugaagauug caaaacgugg cggcgugacc gcaauggagg cagugcaugc aucgcgcaau    420
gcacugacgg gugccccccu gaacuuaaca cccgaucaag uggagcgau agcgucaaac      480 ggcgggggua acaggcuuu ggagacggua cagcgguuau ugccgguacu cugccaggac      540
cacggauuga caccggacca aguggugcg auugcgucca caacggagg caagcaggca       600 cuagagacgu ccaacggcu ucuucccguu cuuugucagg aucaugggcu aaccccugau      660 caggaucg cuauagcuuc aaauggaggg ggcaagcaag cacuggagac uguucaacga       720
cuccugccag ugcucugcca agaccacgga cuuacaccag aucaaguggu ugcuauugcc     780
uccaauggug gcgggaaaca agcguuggaa acugugcaga gacuguuacc ugucuugugu    840
caagaccacg gccucacgcc agaucagguc guagccauag cgucgaacau ugguggguag     900
caagcccuug aaacgguca gcgucuucug ccggaguugu gccaggacca cggacuaacg      960
ccggaucagg ucuagccau ugcuucaaau gggggcgcga aacaggcgcu agagacaguc     1020
cagcgccucu ugccgugguu augccaggau cacggcuaa ccccagacca aguguggcu      1080 auugcaucua acaauggugg caaacaagcc uuggagacag ugcaacgauu acugccuguc   1140
```

| | |
|---|---|
| uuaugucagg aucauggccu gacgcccgau cagguagugg caaucgcauc uaacauugga | 1200 |
| gguaagcaag cacuggagac uguccagaga uuguuacccg uacuauguca agaucauggu | 1260 |
| uugacgccug aucagguugu ugcgauagcc agcaauaacg gagggaaaca ggcucuugaa | 1320 |
| accguacagc gacuucuccc agucuugugc caagaucacg ggcuuacucc ugaucaaguc | 1380 |
| guagcuaucg ccagcaauaa cggugggaaaa caggcccugg aaaccguaca acgucuccuc | 1440 |
| ccaguacuuu gucaagacca cggguugacu ccggaucaag ucgucgcgau cgcgagcaau | 1500 |
| gguggggga agcaggcgcu ggaaacuguu cagagacugc ugccuguacu uugucaggac | 1560 |
| cauggucuga caccugacca aguuguggcg auagccagua auacgggggg aaaacaggca | 1620 |
| cuagagagca uuguggccca gcugagccgg ccugauccgg cguuggccgc guugaccaac | 1680 |
| gaccaccucg ucgccuuggc cugccucggc ggacguccug ccauggaugc agugaaaaag | 1740 |
| ggauugccgc acgcgccgga auugaucaga agagucaauc gccguauugg cgaacgcacg | 1800 |
| ucccaucgcg uugcgauauc uagaguggga ggaagcucgc gcagagaguc caucaaccca | 1860 |
| uggauucuga cugguuucgc ugaugccgaa ggaugcuucc gacuagacau ccgcaacgca | 1920 |
| aacgauuuaa gagccggaua cagaacuaga cuggccuucg aaaucguacu gcacaacaag | 1980 |
| gacaaaucga uucuggagaa uauccagucg acuuggaagg ucggcacaau cuacaacgcg | 2040 |
| ggcgacaacg cagucagacu gcaagucaca cguuucgaag auuugaaagu gauuaucgac | 2100 |
| cacuucgaga auauccgcu gauaacacag aaauugggcg auuacaaguu guuuaaacag | 2160 |
| gcauucagcg ucauggagaa caaagaacau cuuaaggaga augggauuaa ggagcucgua | 2220 |
| cgaaucaaag cuaagaugaa uuggggucuc aaugacgaau ugaaaaaagc auuuccagag | 2280 |
| aacauuagca aagagcgcuc ccuuaucaau aagaacauuc cgaaucucaa auggcuggcu | 2340 |
| ggauucacau cuggugacgg cucguucgug guggaacuaa agaagagaag aagcccccguc | 2400 |
| aagguaggag ugcggcugcg auucagcauc acccagcaca ucagagacaa gaaccugaug | 2460 |
| aauucauuga uaacauaccu aggcuguggu cguaucguug agaauaacaa aucugagcac | 2520 |
| aguuggcucg aauucauugu aacaaaauuc agcgauauca acgacaagau cauuccggua | 2580 |
| uuccaggaaa auacucugau uggcgucaaa cucgaggacu uugaagauug ugcaagguu | 2640 |
| gccaaauuga ucgaagagaa gaaacaccug accgaauccg guuggaauga gauuaagaaa | 2700 |
| aucaagcuga acaugaacaa aggucgguc uucagcggcc gcugauaa | 2748 |

<210> SEQ ID NO 32
<211> LENGTH: 2748
<212> TYPE: RNA
<213> ORGANISM: Artificial Sequence
<220> FEATURE:
<223> OTHER INFORMATION: Made in Lab - synthesized megaTAL CBLB.A8 mRNA

<400> SEQUENCE: 32

| | |
|---|---|
| augggauccg cgccaccuaa gaagaaacgc aaagucgugg aucuacgcac gcucggcuac | 60 |
| agucagcagc agcaagagaa gaucaaaccg aaggugcguu cgacaguggc gcagcaccac | 120 |
| gaggcacugg ugggccaugg guuuacacac gcgcacaucg uugcgcucag ccaacacccg | 180 |
| gcagcguuag ggaccgucgc ugucacguau cagcacauaa ucacggcguu gccagaggcg | 240 |
| acacacgaag acaucguugg cgucggcaaa caguggcccg gcgcacgcgc ccuggaggcc | 300 |
| uugcucacgg augcggggga guugagaggu ccgccguuac aguuggacac aggccaacuu | 360 |
| gugaagauug caaaacgugg cggcugacc gcaauggagg caguagugc aucgcgcaau | 420 |
| gcacugacgg gugcccccu gaacuuaaca cccgaucaag ugguagcgau agcgucaaac | 480 |

```
ggcgggggua aacaggcuuu ggagacggua cagcgguuau ugccgguacu cugccaggac    540
cacggauuga caccggacca aguggugggcg auugcgucca acaacggagg caagcaggca    600
cuagagacug uccaacggcu ucuucccguu cuuugucagg aucaugggcu aaccccugau    660
cagguagucg cuauagcuuc aaauggaggg ggcaagcaag cacuggagac uguucaacga    720
cuccugccag ugcucugcca agaccacgga cuuacaccag aucaagguggu ugcuauugcc    780 uccaauggug gcgggaaaca agcguuggaa acugugcaga gacuguuacc ugucuugugu    840
caagaccacg gccucacgcc agaucaggug guagccauag cgucgaacau ugguggguaag    900 caagcccuug aaacgguccca gcgucuucug ccgguguugu gccaggacca cggacuaacg    960
ccggaucagg ucguagccau ugcuucaaau gggggcggca acaggcgcu agagacaguc    1020 cagcgccucu ugccguguu augccaggau acggcuuaa ccccagacca aguuguggcu    1080
auugcaucua acaauggugg caaacaagcc uuggagacag ugcaacgauu acugccuguc    1140
uuaugucagg aucauggccu gacgcccgau cagguagugg caaucgcauc uaacauugga    1200
gguaagcaag cacuggagac uguccagaga uuguuacccg uacuaugca agaucaugu    1260 uugacgccug aucagguugu ugcgauagcc agcaauaacg gagggaaaca ggcucuugaa    1320
accguacagc gacuucuccc aguccuugugc caagaucacg ggcuuacucc ugaucaaguc    1380
guagcuaucg ccagcaauaa cgguggaaaa caggcccugg aaaccguaca acgucuccuc    1440
ccaguacuuu gucaagacca cgggguugacu ccggaucaag ucgucgcgau cgcgagcaau    1500
ggugggggga agcaggcgcu ggaaacuguu cagagacugc ugccuguacu uguucaggac    1560 caugggucuga caccugacca aguuguggcg auagccagua auaucggggg aaaacaggca    1620
cuagagagca uugguggccca gcugagccgg ccugauccgg cguuggccgc guugaccaac    1680
gaccaccucg ucgccuuggc cugccucggc ggacguccug ccauggaugc agugaaaaag    1740
ggauugccgc acgcgccgga auugaucaga agagucaauc gccguauugg cgaacgcacg    1800
ucccaucgcg uugcgauauc uagaguggga ggaagcucgc gcagagaguc caucaacccca    1860 uggauucuga cugguuucgc ugaugccgaa ggaugcuucc gacuagacau ccgcaacgca    1920
aacgauuuaa gagccggaua cagaacuaga cuggccuucg aaaucguacu gcacaacaag    1980
gacaaaucga uucuggagaa uaccagucg acuuggaagg ucggcacaau cuacaacgcg    2040
ggcgacaacg cagucagacu gcaagucaca cguuucgaag auuugaaagu gauuaucggc    2100
cacuucgaga auauuccgcu gauaacacag aaauuggggcg auuacaaguu guuuaaacag    2160
gcauucagcu caguggagaa caagaacauu cuuaaggaga auggggauuaa ggagcucgua    2220 cgaaucaaag cuaagaugaa uugggggucuc aaugacgaau ugaaaaagc auuccagag    2280 aacauuagca aagagcgccc ccuuaucaau aagaacaucc caaaucucaa auggcuggcu    2340
ggauucacau cuggugacgg cucguucaug guggaacuaa ugaagaauaa gaauaacguu    2400 auugacgug ugccgcugag auucucaauc ucccagcaca ucagagacaa gaaccugaug    2460
aauucauuga uaacauaccu aggcuguggu cguaucguug agaauaacaa aucgagcac    2520 aguuggcucg aauucauugu aacaaaauuc agcgauauca acgacaagau cauuccggua    2580
uuccaggaaa auacucugau uggcgucaaa cucgaggacu ugaagauug ugcaagguu    2640 gccaaauuga ucgaagagaa gaaacaccug accgaauccg guuuggauga gauuaagaaa    2700
aucaagcuga acaugaacaa aggucgguguc uucagcggcc gcugauaa              2748
```

<210> SEQ ID NO 33

<211> LENGTH: 2748
<212> TYPE: RNA
<213> ORGANISM: Artificial Sequence
<220> FEATURE:
<223> OTHER INFORMATION: Made in Lab - codon optimized megaTAL CBLB.E3 mRNA

<400> SEQUENCE: 33
augggauccg cccccccgaa aaagaagcgg aaaguggucg accuuagaac ccugggauac 60
ucccagcagc agcaggaaaa gauuaagccg aagguccggu caacaguggc ccagcaccac 120
gaggcacuug ugggacacgg auuuacccau gcccauaucg ucgcccuuuc ccagcauccg 180
gcggcucugg gaaccgucgc cgugaccuac cagcauauaa ucacugcgcu gccugaagcu 240
acccacgagg auauuguggg agugggaaag caguggagcg gagcgagagc gcuggaagcc 300
cuccugaccg acgcaggaga gcuccgggga ccuccacucc aacucgacac uggacagcuu 360
gugaagauug ccaagagagg cggcgucacc gcuauggagg cggugcacgc uucccggaac 420
gcucugaccg gagccccucu gaaucugacu ccagaccaag ucguggcaau cgcauccaac 480
ggcgggggca agcaagcucu ggaaacagug caacgccucc ugcccgugcu gugccaggac 540
cacggacuca cccccgauca aguaguggcc aucgcuucca acaacggugg aaaacaggcu 600
cucgaaacag uccagcggcu guugccaguc cugugccaag accacggguu gacgccugac 660
caaguggugg ccauagcguc gaauggugga ggcaagcaag ccuuggaaac cguucagagg 720
uugcucccag ugcuuugcca ggaucacgga cugacaccug accagguggu cgcaauugcc 780
uccaacggag gggggaagca ggcccucgaa acggugcaac ggcugcugcc ugugcucugu 840
caggaccacg gcuugacccc cgaccaagug guggccaucg cgagcaauau ugguggaaag 900
caggccuugg agacugugca gagacuucug ccggugcucu gccaagauca uggccuuacc 960
ccagaucaag uggucgcgau cgcuucgaac ggaggcggca aacaggcccu ggagacugug 1020
caaagacugc ugccggugu gugucaggau cauggauuga cucccgauca gguggugcg 1080
aucgccucaa auaacggagg aaaacaagcc cucgagacug uucagcggcu acugcccguc 1140
cugugucagg accauggcuu gacacccgac cagguagucg ccaucgcguc caacaucggc 1200
ggcaagcagg cacucgaaac cgugcagaga cugcucccgg ugcugugcca ggaccacggu 1260
cugacuccgg aucaggucgu ugcuaucgcc ucgaacaacg ggggaaagca agcgcuugag 1320
acuguccaac gccuucugcc cgucuugugu caagaucacg ggcuuacucc ggaccagguc 1380
guggcuauug ccagcaacaa cggcgggaag caagcccugg aaacugugca gcgccuguug 1440
ccggucuugu gccaagacca cggcucacc ccggaucaag ucgucgcuau cgcaucgaac 1500
gguggaggua aacaagcacu ggaaaccguc cagaggcugc uuccgguccu cugucaagac 1560
cauggccuca cuccugauca aguggucgcc auagccagca auaucggugg gaaacaggca 1620
cuggagagca ucgucgccca gcuuucccgg ccagauccgg cccuggccgc uuugacgaac 1680
gaccaucugg uggcccuggc uugccugggg ggaaggccag cgauggacgc cgugaagaag 1740
ggacugcccc augccccuga gcugauucgg cgagugaaca ggcggaucgg cgaacggacc 1800
ucccaccgcg uggcgaucuc cagagucggg ggaucgucca gacgcgaguc caucaaccca 1860
uggauccuca ccggauucgc cgaugcagaa ggguguuucc ggcuggauau cagaaacgcg 1920
aacgaucucc gugcugggua ccggaccaga cuggccuucg agaucgugcu gcacaacaag 1980
gacaagagca uucucgaaaa cauccagucg accuggaaag ugggaacuau cuacaacgcg 2040
ggagauaacg cggugcgccu gcaagucacc agguucgagg aucucaaggu gaucaucgau 2100

| | | | | |
|---|---|---|---|---|
| cacuucgaga | aguacccucu | gaucacccaa | aagcuggguq | auuacaagcu guucaagcag | 2160 |
| gcguuccccg | ucauggagaa | caaggaacac | cucaaggaaa | acggcauuaa agagcucgug | 2220 |
| agaaucaagg | ccaagaugaa | cuggggccug | aacgacgaac | ucaagaaagc cuuccccgag | 2280 |
| aacaucucca | aggagcgguc | ccugaucaac | aagaacaucc | ccaaccugaa guggcucgcg | 2340 |
| ggcuucacca | gcggagaugg | cucguucgug | gucgaacuga | agaagaggcg gucccccagug | 2400 |
| aaggugggag | ugcgacugcg | guuccauu | acucagcaca | uccgcgacaa gaaccugaug | 2460 |
| aacucgcuga | ucaccuaccu | uggaugcggc | agaaucgugg | agaauaacaa guccgagcac | 2520 |
| uccuggcugg | aguucaucgu | gaccaaguuu | ucggauauua | ugacaagau uauuccggug | 2580 |
| uuccaggaaa | acacccugau | uggugucaaa | cuggaggacu | ugaggacug gugcaaggug | 2640 |
| gccaagcuua | ucgaagagaa | gaagcaccug | accgaguccg | gcuggacga aucaagaag | 2700 |
| aucaagcuga | acaugaacaa | gggucgcgug | uucuccgguc | gcugauag | 2748 |

<210> SEQ ID NO 34
<211> LENGTH: 2748
<212> TYPE: RNA
<213> ORGANISM: Artificial Sequence
<220> FEATURE:
<223> OTHER INFORMATION: Made in Lab - synthesized megaTAL CBLB.D2 mRNA

<400> SEQUENCE: 34

| | | | | |
|---|---|---|---|---|
| augggauccg | cgccaccuaa | gaagaaacgc | aaagucgugg | aucuacgcac gcucggcuac | 60 |
| agucagcagc | agcaagagaa | gaucaaaccg | aaggugcguu | cgacaguggc gcagcaccac | 120 |
| gaggcacugu | uggccauggu | guuuacacac | gcgcacaucg | uugcgcucag ccaacacccg | 180 |
| gcagcguuag | ggaccgucgc | ugucacguau | cagcacauaa | ucacggcguu gccagaggcg | 240 |
| acacacgaag | acaucguugg | cgucggcaaa | caguggcccg | cgcacgcgc ccuggaggcc | 300 |
| uugcucacgg | augcgggga | guugagaggu | ccgccguuac | aguuggacac aggccaacuu | 360 |
| gugaagauug | caaaacgugg | cggcugacc | gcaauggagg | cagugcaugc aucgcgcaau | 420 |
| gcacugacgg | gugccccccu | gaacuuaaca | cccgaucaag | ugguagcgau agcgucaaac | 480 |
| ggcgggggua | acaggcuuuu | ggagacggua | cagcgguuau | ugccgguacu ugccaggac | 540 |
| cacggauuga | caccggacca | aguggugcg | auugcgucca | caacggagg caagcaggca | 600 |
| cuagagacug | uccaacggcu | ucuucccguu | cuuugucagg | aucaugggcu aaccccugau | 660 |
| cagguagucg | cuauagcuuc | aaauggaggg | ggcaagcaag | cacuggagac uguucaacga | 720 |
| cuccugccag | ugcucugcca | agaccacgga | cuuacaccag | aucaagguggu ugcuauugcc | 780 |
| uccaauggug | gcgggaaaca | agcguuggaa | acugugcaga | gacuguuacc ugucuugugu | 840 |
| caagaccacg | gccucacgcc | agaucaggug | guagccauag | cgucaacau ggugguaag | 900 |
| caagcccuug | aaacgguccca | gcgucuucug | ccguguugu | gccaggacca cggacuaacg | 960 |
| ccggaucagg | ucguagccau | ugcuucaaau | ggggcggca | acaggcgcu agagacaguc | 1020 |
| cagcgccucu | ugccuguguu | augccaggau | cacggcuuaa | ccccagacca aguuguggcu | 1080 |
| auugcaucua | acaauggugg | caaacaagcc | uuggagacag | ugcaacgauu acugccuguc | 1140 |
| uuaugucagg | aucauggccu | gacgcccgau | caguaguag | caaucgcauc uaacauugga | 1200 |
| gguaagcaag | cacuggagac | ugccagaga | uuguuacccg | uacuauguca agaucauggu | 1260 |
| uugacgccug | aucagguugu | ugcgauagcc | agcauaaacg | gagggaaaca ggcucuugaa | 1320 |
| accguacagc | gacuucuccc | agucuugugc | caagaucacg | gcuuacucc ugaucaaguc | 1380 |
| guagcuaucg | ccagcaauaa | cgguggaaaa | caggcccugg | aaaccguaca acgucuccuc | 1440 |

```
ccaguacuuu gucaagacca cggguugacu ccggaucaag ucgucgcgau cgcgagcaau   1500 gguggggga agcaggcgcu ggaaacuguu cagagacugc ugccuguacu uugucaggac   1560
cauggucuga caccugacca aguuguggcg auagccagua auaucggggg aaaacaggca   1620
cuagagagca uuguggccca gcugagccgg ccugauccgg cguuggccgc guugaccaac   1680
gaccaccucg ucgccuuggc cugccucggc ggacguccug ccauggaugc agugaaaaag   1740
ggauugccgc acgcgccgga auugaucaga agagucaauc gccguauugg cgaacgcacg   1800
ucccaucgcg uugcgauauc uagaguggga ggaagcucgc gcagagaguc caucaaccca   1860
uggauucuga cugguuucgc ugaugccgaa ggaugcuucc gacuagacau ccacaacgca   1920
aacguauuga ggucugguua cagaacuaga cuguccuucg aaaucguacu gcacaacaag   1980
gacaaaucga uucuggagaa uauccagucg acuuggaagg ucggcaaaau cuacaacgcg   2040
ggcgacaacg cagucagacu gcaagucaca cguuucgaag auuugaaagu gauuaucgac   2100
cacuucgaga aauauccgcu gauaacacag aaauugggcg auuacaaguu guuuaaacag   2160
gcauucagcg ucauggagaa caaagaacau cuuaaggaga augggauuaa ggagcucgua   2220
cgaaucaaag cuaagaugaa uuggggucuc aaugacgaau ugaaaaaagc auuuccagag   2280
aacauuagca aagagcgccc ccuuaucaau aagaacauuc cgaaucucaa auggcuggcu   2340
ggauucacau cuggugacgg cucguucaug guggaacuaa ugaagaauaa gaauaacguu   2400
auuguacgug ugcgucugag auucucaauc ucccagcaca ucagagacaa gaaccugaug   2460
aauucauuga uaacauaccu aggcuguggu cguaucguug agaauaacaa aucugagcac   2520
aguuggcucg aauucauugu aacaaaauuc agcgauauca acgacaagau cauuccggua   2580
uuccaggaaa auacucugau uggcgucaaa cucgaggacu uugaagauug gugcaagguu   2640
gccaaauuga ucgaagagaa gaaacaccug accgaauccg guuuggauga gauuaagaaa   2700
aucaagcuga acaugaacaa aggucguguc uucagcggcc gcugauaa                2748
```

<210> SEQ ID NO 35
<211> LENGTH: 2748
<212> TYPE: RNA
<213> ORGANISM: Artificial Sequence
<220> FEATURE:
<223> OTHER INFORMATION: Made in Lab - synthesized megaTAL CBLB.B5 mRNA

<400> SEQUENCE: 35

```
augggauccg cgccaccuaa gaagaaacgc aaagucgugg aucuacgcac gcucggcuac     60
agucagcagc agcaagagaa gaucaaaccg aaggugcguu cgacaguggc gcagcaccac    120
gaggcacugg ugggccaugg guuuacacac gcgcacaucg uugcgcucag ccaacacccg    180
gcagcguuag ggaccgucgc ugucacguau cagcacauaa ucacggcguu gccagaggcg    240
acacacgaag acaucguugg cgucggcaaa caguggucg gcgcacgcgc ccuggaggcc    300
uugcucacgg augcgggga guugagaggu ccgccguuac aguuggacac aggccaacuu    360
gugaagauug caaaacgugg cggcgugacc gcaauggagg cagugcaugc aucgcgcaau    420
gcacugacgg gugcccccu gaacuuaaca cccgaucaag ugguagcgau agcgucaaac    480
ggcgggggua aacaggcuuu ggagacggua cagcgguuau ugccgguacu cugccaggac    540
cacggauuga caccggacca aguggugggcg auugcgucca acaacggagg caagcaggca    600
cuagagacug uccaacggcu ucuucccguu cuuugucagg aucaugggcu aaccccugau    660
cagguagucg cuauagcuuc aaauggaggg ggcaagcaag cacuggagac uguucaacga    720
```

| | | | | |
|---|---|---|---|---|
| cuccugccag | ugcucugcca | agaccacgga | cuuacaccag | aucaaguggu ugcuauugcc | 780 |
| uccaauggug | gcgggaaaca | agcguuggaa | acugugcaga | gacuguuacc ugucuugugu | 840 |
| caagaccacg | gccucacgcc | agaucaggug | guagccauag | cgucgaacau uggugguaag | 900 |
| caagcccuug | aaacggucca | gcgucuucug | ccgguguugu | gccaggacca cggacuaacg | 960 |
| ccggaucagg | ucguagccau | ugcuucaaau | ggggcggca | aacaggcgcu agagacaguc | 1020 |
| cagcgccucu | ugccuguguu | augccaggau | cacggcuuaa | ccccagacca aguugugcu | 1080 |
| auugcaucua | acaaugguggu | caaacaagcc | uuggagacag | ugcaacgauu acugccuguc | 1140 |
| uuaugucagg | aucauggccu | gacgcccgau | cagguagugg | caaucgcauc uaacauugga | 1200 |
| gguaagcaag | cacuggagac | uguccagaga | uuguuacccg | uacuaugucu agaucauggu | 1260 |
| uugacgccug | aucagguugu | ugcgauagcc | agcaauaacg | gagggaaaca ggcucuugaa | 1320 |
| accguacagc | gacuucuccc | agucuugugc | caagaucacg | ggcuuacucc ugaucaaguc | 1380 |
| guagcuaucg | ccagcaauaa | cgguggaaaa | caggcccugg | aaaccguaca acgucuccuc | 1440 |
| ccaguacuuu | gucaagacca | cggguugacu | ccggaucaag | ucgucgcgau cgcgagcaau | 1500 |
| ggugggggga | agcaggcgcu | ggaaacuguu | cagagacugc | ugccuguacu uugucaggac | 1560 |
| caugguucga | caccugacca | aguuguggcg | auagccagua | auaucggggg aaaacaggca | 1620 |
| cuagagagca | uuguggccca | gcugagccgg | ccugauccgg | cguuggccgc guugaccaac | 1680 |
| gaccaccucg | ucgccuuggc | cugccucggc | ggacguccug | ccauggaugc agugaaaaag | 1740 |
| ggauugccgc | acgcgccgga | auugaucaga | agagucaauc | gccguauugg cgaacgcacg | 1800 |
| ucccaucgcg | uugcgauauc | uagaguggga | ggaagcucgc | gcagagaguc caucaaccca | 1860 |
| uggauucuga | cugguuucgc | ugaugccgaa | ggaugcuucc | gacuagacau ccacaacgca | 1920 |
| aacguauuga | ggucugguua | cagaacuaga | cuguccuucg | aaaucguacu gcacaacaag | 1980 |
| gacaaaucga | uucuggagaa | uauccagucg | acuuggaagg | ucggcacaau cuacaacgcg | 2040 |
| ggcgacaacg | cagucagacu | gcaagucaca | cguuucgaag | auuugaaagu gauuaucgac | 2100 |
| cacuucgaga | aauauccgcu | gauaacacag | aaauugggcg | auuacaaguu guuuaaacag | 2160 |
| gcauucagcc | ucauggagaa | caaagaacau | cuuaaggaga | augggauuaa ggagcucgua | 2220 |
| cgaaucaaag | cuaagaugaa | uuggggucuc | aaugacgaau | ugaaaaagc auuccagag | 2280 |
| aacauuagca | aagagcgccc | ccuuaucaau | aagaacauuc | cgaaucucaa augcuggcu | 2340 |
| ggauucacau | cuggugacgg | cucguucgug | guggaacuaa | agaagagaag aagccccguc | 2400 |
| aagguaggag | ugcggcugcg | auucggcauc | acccagcaca | ucagagacaa gaaccugaug | 2460 |
| aauucauuga | uaacauaccu | aggcuguggu | cguaucguug | agaauaacaa aucugagcac | 2520 |
| aguuggcucg | aauucauugu | aacaaaauuc | agcgauauca | acgacaagau cauuccggua | 2580 |
| uuccaggaaa | auacucugau | uggcgucaaa | ucgaggacu | uugaagauug gugcaagguu | 2640 |
| gccaaauuga | ucgaagagaa | gaaacaccug | accgaauccg | guuuggauga gauuaagaaa | 2700 |
| aucaagcuga | acaugaacaa | aggucguguc | uucagcggcc | gcugauaa | 2748 |

<210> SEQ ID NO 36
<211> LENGTH: 2748
<212> TYPE: RNA
<213> ORGANISM: Artificial Sequence
<220> FEATURE:
<223> OTHER INFORMATION: Made in Lab - synthesized megaTAL CBLB.F6 mRNA

<400> SEQUENCE: 36
augggauccg cgccaccuaa gaagaaacgc aaagucgugg aucuacgcac gcucggcuac      60

-continued

```
agucagcagc agcaagagaa gaucaaaccg aaggugcguu cgacaguggc gcagcaccac    120
gaggcacugg ugggccaugg guuuacacac gcgcacaucg uugcgcucag ccaacacccg    180
gcagcguuag ggaccgucgc ugucacguau cagcacauaa ucacggcguu gccagaggcg    240
acacacgaag acaucguugg cgucggcaaa cagugguccg gcgcacgcgc ccuggaggcc    300
uugcucacgg augcggggga guugagaggu ccgccguuac aguuggacac aggccaacuu    360
gugaagauug caaaacgugg cggcugacc gcaauggagg cagucaugc aucgcgcaau      420 gcacugacgg gugccccccu gaacuuaaca cccgaucaag ugguagcgau agcgucaaac    480
ggcgggggua aacaggcuuu ggagacggua cagcgguuau ugccgguacu cugccaggac    540
cacggauuga caccggacca aguggugcg auugcgucca caacggagg caagcaggca      600 cuagagacug uccaacggcu ucuucccguu cuuugucagg aucaugggcu aaccccugau    660
cagguagucg cuauagcuuc aaauggaggg ggcaagcaag cacuggagac uguucaacga    720
cuccugccag ugcucugcca agaccacgga cuuacaccag aucaagugu ugcuauugcc     780 uccaauggug gcgggaaaca agcguuggaa acugugcaga gacuguuacc ugucuugugu    840
caagaccacg gccucacgcc agaucaggug guagccauag cgucgaacau gguggguaag    900
caagcccuug aaacgguccca gcgucuucug ccgguguugu gccaggacca cggacuaacg    960
ccggaucagg ucguagccau ugcuucaaau ggggcggca aacaggcgcu agagacaguc     1020
cagcgccucu ugccugugu augccaggau cacggcuuaa ccccagacca aguguggcu      1080 auugcaucua acaaugggg caaacaagcc uggagacag ugcaacgauu acugccuguc       1140
uuaugcuagg aucauggccu gacgcccgau cagguagug caaucgcauc uaacauugga    1200
gguaagcaag cacuggagac uguccagaga uuguuacccg uacuauguca agaucauggu   1260
uugacgccug aucagguugu ugcgauagcc agcaauaacg gagggaaaca ggcucuugaa    1320
accguacagc gacuucuccc agucuugugc caagaucacg ggcuuacucc ugaucaaguc    1380
guagcuaucg ccagcaauaa cggugaaaa caggcccugg aaaccguaca acgucccuc      1440 ccaguacuuu gucaagacca cgggguugacu ccggaucaag ucgucgcgau cgcgagcaau   1500
ggugggggga agcaggcgcu ggaaacuguu cagagacugc ugccuguacu uugucaggac    1560
caugguugga caccugacca aguuguggcg auagccagua auaucggggg aaaacaggca    1620
cuagagagca uugugggcca gcugagccgg ccugauccgg cguuggccgc guugaccaac    1680
gaccaccucg ucgccuuggc cugccucggc ggacguccug ccauggaugc agugaaaaag    1740
ggauugccgc acgcgccgga auugaucaga agagucaauc gccguauugg cgaacgcacg    1800
ucccaucgcg uugcgauauc uagagugga ggaagcucgc gcagagaguc caucaaccca    1860
uggauucuga cugguuucgc ugaugccaa ggaugcuucc gacuagacau ccgcaacgca     1920
aacgauuuaa gagccggaua cagaacuaga cuggccuucg aaaucguacu gcacaacaag    1980
gacaaaucga uucuggagaa uauccagucg acuggaaagg ucggcacaau cuacaacgcg    2040
ggcgacaacg cagucagacu gcaagucaca cguuucgaag auuugaaagu gauuaucgac    2100
cacuucgaga aauauccgcu gauaacacag aaauuggggcg auuacaaguu guuuaaacag    2160
gcauucagcg ucauggagaa caagaacau cuuaaggaga augggauuaa ggagcucgua    2220
cgaaucaaag cuaagaugaa uugggucuc aaugacgaau ugaaaaagc auuccagag       2280 aacauuagca agagcgcccc ccuuaucaau aagaacauuc cgaaucucaa augcuggcu    2340 ggauucacau cuggugacgg cucguucaug guggaacuaa ugaagaauaa gaauaacguu    2400
```

-continued

```
auuguacgug ugcgucugag auucucaauc ucccagcaca ucagagacaa gaaccugaug    2460
aauucauuga uaacauaccu aggcuguggu cguaucguug agaauaacaa aucugagcac    2520
aguuggcucg aauucauugu aacaaaauuc agcgauauca acgacaagau cauuccggua    2580
uuccaggaaa auacucugau uggcgucaaa cucgaggacu ugaagauug ugcaagguu     2640 gccaaauuga ucgaagagaa gaaacaccug accgaauccg guuggauga gauuaagaaa    2700 aucaagcuga acaugaacaa aggucguguc uucagcggcc gcugauaa              2748
```

<210> SEQ ID NO 37
<211> LENGTH: 711
<212> TYPE: RNA
<213> ORGANISM: Mus musculus

<400> SEQUENCE: 37

```
augucugagc caccucgggc ugagaccuuu guauuccugg accuagaagc cacugggcuc      60
ccaaacaugg acccugagau ugcagagaua ucccuuuuug cuguucaccg cucuucccug     120
gagaacccag aacgggauga uucugguucc uggugcugc cccguuucu ggacaagcuc      180 acacugugca ugugcccgga gcgcccuuu acugccaagg ccagugagau uacugguuug     240
agcagcgaaa gccugaugca cugcgggaag gcugguuuca auggcgcugu gguaaggaca    300
cugcagggcu uccuaagccg ccaggagggc cccaucugcc uuguggccca caauggcuuc    360
gauuaugacu ucccacugcu gugcacggag cuacaacguc ugggugccca ucugccccaa    420
gacacugucu gccuggacac acugccugca uugcggggcc uggaccgugc ucacagccac    480
ggcaccaggg cucaaggccg caaaagcuac agccuggcca gucucuucca ccgcuacuuc    540
caggcugaac ccagugcugc ccauucagca gaaggugaug ugcacacccu gcuucugauc    600
uuccugcauc gugcuccuga gcugcucgcc ugggcagaug agcaggcccg cagcugggcu    660
cauauugagc ccauguacgu gccaccugau gguccaagcc ucgaagccug a            711
```

<210> SEQ ID NO 38
<211> LENGTH: 236
<212> TYPE: PRT
<213> ORGANISM: Mus musculus

<400> SEQUENCE: 38

```
Met Ser Glu Pro Pro Arg Ala Glu Thr Phe Val Phe Leu Asp Leu Glu
1               5                   10                  15

Ala Thr Gly Leu Pro Asn Met Asp Pro Glu Ile Ala Glu Ile Ser Leu
            20                  25                  30

Phe Ala Val His Arg Ser Ser Leu Glu Asn Pro Glu Arg Asp Asp Ser
        35                  40                  45

Gly Ser Leu Val Leu Pro Arg Val Leu Asp Lys Leu Thr Leu Cys Met
    50                  55                  60

Cys Pro Glu Arg Pro Phe Thr Ala Lys Ala Ser Glu Ile Thr Gly Leu
65                  70                  75                  80

Ser Ser Glu Ser Leu Met His Cys Gly Lys Ala Gly Phe Asn Gly Ala
                85                  90                  95

Val Val Arg Thr Leu Gln Gly Phe Leu Ser Arg Gln Glu Gly Pro Ile
            100                 105                 110

Cys Leu Val Ala His Asn Gly Phe Asp Tyr Asp Phe Pro Leu Leu Cys
        115                 120                 125

Thr Glu Leu Gln Arg Leu Gly Ala His Leu Pro Gln Asp Thr Val Cys
    130                 135                 140
```

```
Leu Asp Thr Leu Pro Ala Leu Arg Gly Leu Asp Arg Ala His Ser His
145                 150                 155                 160

Gly Thr Arg Ala Gln Gly Arg Lys Ser Tyr Ser Leu Ala Ser Leu Phe
                165                 170                 175

His Arg Tyr Phe Gln Ala Glu Pro Ser Ala Ala His Ser Ala Glu Gly
            180                 185                 190

Asp Val His Thr Leu Leu Leu Ile Phe Leu His Arg Ala Pro Glu Leu
        195                 200                 205

Leu Ala Trp Ala Asp Glu Gln Ala Arg Ser Trp Ala His Ile Glu Pro
    210                 215                 220

Met Tyr Val Pro Pro Asp Gly Pro Ser Leu Glu Ala
225                 230                 235

<210> SEQ ID NO 39
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 39

Gly Gly Gly
1

<210> SEQ ID NO 40
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 40

Asp Gly Gly Gly Ser
1               5

<210> SEQ ID NO 41
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 41

Thr Gly Glu Lys Pro
1               5

<210> SEQ ID NO 42
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 42

Gly Gly Arg Arg
1

<210> SEQ ID NO 43
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 43
```

```
Gly Gly Gly Gly Ser
1               5

<210> SEQ ID NO 44
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 44

Glu Gly Lys Ser Ser Gly Ser Gly Ser Glu Ser Lys Val Asp
1               5                   10

<210> SEQ ID NO 45
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 45

Lys Glu Ser Gly Ser Val Ser Ser Glu Gln Leu Ala Gln Phe Arg Ser
1               5                   10                  15

Leu Asp

<210> SEQ ID NO 46
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 46

Gly Gly Arg Arg Gly Gly Gly Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 47

Leu Arg Gln Arg Asp Gly Glu Arg Pro
1               5

<210> SEQ ID NO 48
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 48

Leu Arg Gln Lys Asp Gly Gly Gly Ser Glu Arg Pro
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Exemplary linker sequence
```

```
<400> SEQUENCE: 49

Leu Arg Gln Lys Asp Gly Gly Gly Ser Gly Gly Gly Ser Glu Arg Pro
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 50

Glu Xaa Xaa Tyr Xaa Gln Xaa
1               5

<210> SEQ ID NO 51
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 51

Glu Asn Leu Tyr Phe Gln Gly
1               5

<210> SEQ ID NO 52
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 52

Glu Asn Leu Tyr Phe Gln Ser
1               5

<210> SEQ ID NO 53
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 53

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 54
<211> LENGTH: 19
<212> TYPE: PRT
<213> ORGANISM: Artificial Sequence
<220> FEATURE:
<223> OTHER INFORMATION: Self-cleaving polypeptide comprising 2A site
```

<400> SEQUENCE: 54

Ala Thr Asn Phe Ser Leu Leu Lys Gln Ala Gly Asp Val Glu Glu Asn
1               5                   10                  15

Pro Gly Pro

<210> SEQ ID NO 55
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Leu Leu Lys Gln Ala Gly Asp Val Glu Glu Asn Pro Gly Pro
1               5                   10

<210> SEQ ID NO 56
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 57
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 57

Glu Gly Arg Gly Ser Leu Leu Thr Cys Gly Asp Val Glu Glu Asn Pro
1               5                   10                  15

Gly Pro

<210> SEQ ID NO 58
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 58

Leu Leu Thr Cys Gly Asp Val Glu Glu Asn Pro Gly Pro
1               5                   10

<210> SEQ ID NO 59
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 59

Gly Ser Gly Gln Cys Thr Asn Tyr Ala Leu Leu Lys Leu Ala Gly Asp
1               5                   10                  15

Val Glu Ser Asn Pro Gly Pro

```
                              20

<210> SEQ ID NO 60
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 60

Gln Cys Thr Asn Tyr Ala Leu Leu Lys Leu Ala Gly Asp Val Glu Ser
1               5                   10                  15

Asn Pro Gly Pro
            20

<210> SEQ ID NO 61
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 61

Leu Leu Lys Leu Ala Gly Asp Val Glu Ser Asn Pro Gly Pro
1               5                   10

<210> SEQ ID NO 62
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 62

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 63
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 63

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 64
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 64

Leu Leu Lys Leu Ala Gly Asp Val Glu Ser Asn Pro Gly Pro
1               5                   10

<210> SEQ ID NO 65
<211> LENGTH: 19
```

```
<212> TYPE: PRT
<213> ORGANISM: Artificial Sequence
<220> FEATURE:
<223> OTHER INFORMATION: Self-cleaving polypeptide comprising 2A site

<400> SEQUENCE: 65

Leu Leu Asn Phe Asp Leu Leu Lys Leu Ala Gly Asp Val Glu Ser Asn
1               5                   10                  15

Pro Gly Pro

<210> SEQ ID NO 66
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 66

Thr Leu Asn Phe Asp Leu Leu Lys Leu Ala Gly Asp Val Glu Ser Asn
1               5                   10                  15

Pro Gly Pro

<210> SEQ ID NO 67
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 67

Leu Leu Lys Leu Ala Gly Asp Val Glu Ser Asn Pro Gly Pro
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 68

Asn Phe Asp Leu Leu Lys Leu Ala Gly Asp Val Glu Ser Asn Pro Gly
1               5                   10                  15

Pro

<210> SEQ ID NO 69
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 69

Gln Leu Leu Asn Phe Asp Leu Leu Lys Leu Ala Gly Asp Val Glu Ser
1               5                   10                  15

Asn Pro Gly Pro
            20

<210> SEQ ID NO 70
<211> LENGTH: 24
<212> TYPE: PRT
<213> ORGANISM: Artificial Sequence
<220> FEATURE:
<223> OTHER INFORMATION: Self-cleaving polypeptide comprising 2A site
```

```
<400> SEQUENCE: 70

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 71
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 71

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 72
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 72

Leu Asn Phe Asp Leu Leu Lys Leu Ala Gly Asp Val Glu Ser Asn Pro
1               5                   10                  15

Gly Pro

<210> SEQ ID NO 73
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 73

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 74
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 74

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro
```

```
<210> SEQ ID NO 75
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 75 gccrccatgg                                                              10

<210> SEQ ID NO 76
<211> LENGTH: 22
<212> TYPE: DNA
<213> ORGANISM: Homo sapiens

<400> SEQUENCE: 76
tggggatggg aatatcttac ag                                                22

<210> SEQ ID NO 77
<211> LENGTH: 293
<212> TYPE: PRT
<213> ORGANISM: Artificial Sequence
<220> FEATURE:
<223> OTHER INFORMATION: Synthesized I-OnuI variant CBLB.E3

<400> SEQUENCE: 77
```

Ser Ile Asn Pro Trp Ile Leu Thr Gly Phe Ala Asp Ala Glu Gly Cys
1               5                   10                  15

Phe Arg Leu Asp Ile Arg Asn Ala Asn Asp Leu Arg Ala Gly Tyr Arg
            20                  25                  30

Thr Arg Leu Ala Phe Glu Ile Val Leu His Asn Lys Asp Lys Ser Ile
        35                  40                  45

Leu Glu Asn Ile Gln Ser Thr Trp Lys Val Gly Thr Ile Tyr Asn Ala
    50                  55                  60

Gly Asp Asn Ala Val Arg Leu Gln Val Thr Arg Phe Glu Asp Leu Lys
65                  70                  75                  80

Val Ile Ile Asp His Phe Glu Lys Tyr Pro Leu Ile Thr Gln Lys Leu
                85                  90                  95

Gly Asp Tyr Lys Leu Phe Lys Gln Ala Phe Ser Val Met Glu Asn Lys
            100                 105                 110

Glu His Leu Lys Glu Asn Gly Ile Lys Glu Leu Val Arg Ile Lys Ala
        115                 120                 125

Lys Met Asn Trp Gly Leu Asn Asp Glu Leu Lys Lys Ala Phe Pro Glu
    130                 135                 140

Asn Ile Ser Lys Glu Arg Ser Leu Ile Asn Lys Asn Ile Pro Asn Leu
145                 150                 155                 160

Lys Trp Leu Ala Gly Phe Thr Ser Gly Asp Gly Ser Phe Val Val Glu
                165                 170                 175

Leu Lys Lys Arg Arg Ser Pro Val Lys Val Gly Val Arg Leu Arg Phe
            180                 185                 190

Ser Ile Thr Gln His Ile Arg Asp Lys Asn Leu Met Asn Ser Leu Ile
        195                 200                 205

Thr Tyr Leu Gly Cys Gly Arg Ile Val Glu Asn Asn Lys Ser Glu His
    210                 215                 220

Ser Trp Leu Glu Phe Ile Val Thr Lys Phe Ser Asp Ile Asn Asp Lys
225                 230                 235                 240

Ile Ile Pro Val Phe Gln Glu Asn Thr Leu Ile Gly Val Lys Leu Glu
                245                 250                 255

```
Asp Phe Glu Asp Trp Cys Lys Val Ala Lys Leu Ile Glu Lys Lys
            260                 265                 270

His Leu Thr Glu Ser Gly Leu Asp Glu Ile Lys Lys Ile Lys Leu Asn
            275                 280                 285

Met Asn Lys Gly Arg
            290

<210> SEQ ID NO 78
<211> LENGTH: 293
<212> TYPE: PRT
<213> ORGANISM: Artificial Sequence
<220> FEATURE:
<223> OTHER INFORMATION: Synthesized I-OnuI variant CBLB.F6

<400> SEQUENCE: 78

Ser Ile Asn Pro Trp Ile Leu Thr Gly Phe Ala Asp Ala Glu Gly Cys
1               5                   10                  15

Phe Arg Leu Asp Ile Arg Asn Ala Asn Asp Leu Arg Ala Gly Tyr Arg
            20                  25                  30

Thr Arg Leu Ala Phe Glu Ile Val Leu His Asn Lys Asp Lys Ser Ile
            35                  40                  45

Leu Glu Asn Ile Gln Ser Thr Trp Lys Val Gly Thr Ile Tyr Asn Ala
    50                  55                  60

Gly Asp Asn Ala Val Arg Leu Gln Val Thr Arg Phe Glu Asp Leu Lys
65                  70                  75                  80

Val Ile Ile Asp His Phe Glu Lys Tyr Pro Leu Ile Thr Gln Lys Leu
                85                  90                  95

Gly Asp Tyr Lys Leu Phe Lys Gln Ala Phe Ser Val Met Glu Asn Lys
            100                 105                 110

Glu His Leu Lys Glu Asn Gly Ile Lys Glu Leu Val Arg Ile Lys Ala
        115                 120                 125

Lys Met Asn Trp Gly Leu Asn Asp Glu Leu Lys Lys Ala Phe Pro Glu
    130                 135                 140

Asn Ile Ser Lys Glu Arg Pro Leu Ile Asn Lys Asn Ile Pro Asn Leu
145                 150                 155                 160

Lys Trp Leu Ala Gly Phe Thr Ser Gly Asp Gly Ser Phe Met Val Glu
                165                 170                 175

Leu Met Lys Asn Lys Asn Asn Val Ile Val Arg Val Arg Leu Arg Phe
            180                 185                 190

Ser Ile Ser Gln His Ile Arg Asp Lys Asn Leu Met Asn Ser Leu Ile
        195                 200                 205

Thr Tyr Leu Gly Cys Gly Arg Ile Val Glu Asn Asn Lys Ser Glu His
    210                 215                 220

Ser Trp Leu Glu Phe Ile Val Thr Lys Phe Ser Asp Ile Asn Asp Lys
225                 230                 235                 240

Ile Ile Pro Val Phe Gln Glu Asn Thr Leu Ile Gly Val Lys Leu Glu
                245                 250                 255

Asp Phe Glu Asp Trp Cys Lys Val Ala Lys Leu Ile Glu Lys Lys
            260                 265                 270

His Leu Thr Glu Ser Gly Leu Asp Glu Ile Lys Lys Ile Lys Leu Asn
            275                 280                 285

Met Asn Lys Gly Arg
            290

<210> SEQ ID NO 79
```

<211> LENGTH: 293
<212> TYPE: PRT
<213> ORGANISM: Artificial Sequence
<220> FEATURE:
<223> OTHER INFORMATION: Synthesized I-OnuI variant CBLB.E6

<400> SEQUENCE: 79

Ser Ile Asn Pro Trp Ile Leu Thr Gly Phe Ala Asp Ala Glu Gly Cys
1               5                   10                  15

Phe Arg Leu Asp Ile Arg Asn Ala Asn Asp Leu Arg Ala Gly Tyr Arg
            20                  25                  30

Thr Arg Leu Ser Phe Glu Ile Ser Leu His Asn Lys Asp Lys Ser Ile
        35                  40                  45

Leu Glu Asn Ile Gln Ser Thr Trp Lys Val Gly Thr Ile Tyr Asn Ala
    50                  55                  60

Gly Asp Asn Ala Val Arg Leu Gln Val Thr Arg Phe Glu Asp Leu Lys
65                  70                  75                  80

Val Ile Ile Asp His Phe Glu Lys Tyr Pro Leu Ile Thr Gln Lys Leu
                85                  90                  95

Gly Asp Tyr Lys Leu Phe Lys Gln Ala Phe Ser Val Met Glu Asn Lys
            100                 105                 110

Glu His Leu Lys Glu Asn Gly Ile Lys Glu Leu Val Arg Ile Lys Ala
        115                 120                 125

Lys Met Asn Trp Gly Leu Asn Asp Glu Leu Lys Lys Ala Phe Pro Glu
    130                 135                 140

Asn Ile Ser Lys Glu Arg Pro Leu Ile Asn Lys Asn Ile Pro Asn Leu
145                 150                 155                 160

Lys Trp Leu Ala Gly Phe Thr Ser Gly Asp Gly Ser Phe Met Val Glu
                165                 170                 175

Leu Met Lys Asn Lys Asn Val Ile Val Arg Val Leu Arg Phe
            180                 185                 190

Ser Ile Ser Gln His Ile Arg Asp Lys Asn Leu Met Asn Ser Leu Ile
        195                 200                 205

Thr Tyr Leu Gly Cys Gly Arg Ile Val Glu Asn Asn Lys Ser Glu His
    210                 215                 220

Ser Trp Leu Glu Phe Ile Val Thr Lys Phe Ser Asp Ile Asn Asp Lys
225                 230                 235                 240

Ile Ile Pro Val Phe Gln Glu Asn Thr Leu Ile Gly Val Lys Leu Glu
                245                 250                 255

Asp Phe Glu Asp Trp Cys Lys Val Ala Lys Leu Ile Glu Glu Lys Lys
            260                 265                 270

His Leu Thr Glu Ser Gly Leu Asp Glu Ile Lys Lys Ile Lys Leu Asn
        275                 280                 285

Met Asn Lys Gly Arg
    290

<210> SEQ ID NO 80
<211> LENGTH: 293
<212> TYPE: PRT
<213> ORGANISM: Artificial Sequence
<220> FEATURE:
<223> OTHER INFORMATION: Synthesized I-OnuI variant CBLB.D2

<400> SEQUENCE: 80

Ser Ile Asn Pro Trp Ile Leu Thr Gly Phe Ala Asp Ala Glu Gly Cys
1               5                   10                  15

Phe Arg Leu Asp Ile His Asn Ala Asn Val Leu Arg Ser Gly Tyr Arg

```
                20                  25                  30
Thr Arg Leu Ser Phe Glu Ile Val Leu His Asn Lys Asp Lys Ser Ile
                35                  40                  45
Leu Glu Asn Ile Gln Ser Thr Trp Lys Val Gly Lys Ile Tyr Asn Ala
            50                  55                  60
Gly Asp Asn Ala Val Arg Leu Gln Val Thr Arg Phe Glu Asp Leu Lys
65                  70                  75                  80
Val Ile Ile Asp His Phe Glu Lys Tyr Pro Leu Ile Thr Gln Lys Leu
                85                  90                  95
Gly Asp Tyr Lys Leu Phe Lys Gln Ala Phe Ser Val Met Glu Asn Lys
            100                 105                 110
Glu His Leu Lys Glu Asn Gly Ile Lys Glu Leu Val Arg Ile Lys Ala
            115                 120                 125
Lys Met Asn Trp Gly Leu Asn Asp Glu Leu Lys Lys Ala Phe Pro Glu
        130                 135                 140
Asn Ile Ser Lys Glu Arg Pro Leu Ile Asn Lys Asn Ile Pro Asn Leu
145                 150                 155                 160
Lys Trp Leu Ala Gly Phe Thr Ser Gly Asp Gly Ser Phe Met Val Glu
                165                 170                 175
Leu Met Lys Asn Lys Asn Val Ile Val Arg Val Arg Leu Arg Phe
            180                 185                 190
Ser Ile Ser Gln His Ile Arg Asp Lys Asn Leu Met Asn Ser Leu Ile
            195                 200                 205
Thr Tyr Leu Gly Cys Gly Arg Ile Val Glu Asn Asn Lys Ser Glu His
        210                 215                 220
Ser Trp Leu Glu Phe Ile Val Thr Lys Phe Ser Asp Ile Asn Asp Lys
225                 230                 235                 240
Ile Ile Pro Val Phe Gln Glu Asn Thr Leu Ile Gly Val Lys Leu Glu
                245                 250                 255
Asp Phe Glu Asp Trp Cys Lys Val Ala Lys Leu Ile Glu Gly Lys Lys
            260                 265                 270
His Leu Thr Glu Ser Gly Leu Asp Glu Ile Lys Lys Ile Lys Leu Asn
        275                 280                 285
Met Asn Lys Gly Arg
        290

<210> SEQ ID NO 81
<211> LENGTH: 293
<212> TYPE: PRT
<213> ORGANISM: Artificial Sequence
<220> FEATURE:
<223> OTHER INFORMATION: Synthesized I-OnuI variant CBLB.C2

<400> SEQUENCE: 81

Ser Ile Asn Pro Trp Ile Leu Thr Gly Phe Ala Asp Ala Glu Gly Cys
1               5                   10                  15
Phe Gly Leu Tyr Ile His Asn Ser Asn Val Leu Arg Ser Gly Tyr Arg
            20                  25                  30
Thr Arg Leu Ser Phe Glu Ile Ser Leu His Asn Lys Asp Lys Ser Ile
                35                  40                  45
Leu Glu Asn Ile Gln Ser Thr Trp Lys Val Gly Thr Ile Tyr Asn Ala
            50                  55                  60
Gly Asp Asn Ala Val Arg Leu Gln Val Thr Arg Phe Glu Asp Leu Lys
65                  70                  75                  80
Val Ile Ile Asp His Phe Glu Lys Tyr Pro Leu Ile Thr Gln Lys Leu
```

```
                  85                  90                  95

Gly Asp Tyr Lys Leu Phe Lys Gln Ala Phe Ser Leu Met Glu Asn Lys
                100                 105                 110

Glu His Leu Lys Glu Asn Gly Ile Lys Glu Leu Val Arg Ile Lys Ala
            115                 120                 125

Lys Met Asn Trp Gly Leu Asn Asp Glu Leu Lys Lys Ala Phe Pro Glu
        130                 135                 140

Asn Ile Ser Lys Glu Arg Pro Leu Ile Asn Lys Asn Ile Pro Asn Leu
145                 150                 155                 160

Lys Trp Leu Ala Gly Phe Thr Ser Gly Asp Gly Ser Phe Met Val Glu
                165                 170                 175

Leu Met Lys Asn Lys Asn Val Ile Val Arg Val Arg Leu Arg Phe
                180                 185                 190

Ser Ile Ser Gln His Ile Arg Asp Lys Asn Leu Met Asn Ser Leu Ile
            195                 200                 205

Thr Tyr Leu Gly Cys Gly Arg Ile Val Glu Asn Asn Lys Ser Glu His
        210                 215                 220

Ser Trp Leu Glu Phe Ile Val Thr Lys Phe Ser Asp Ile Asn Asp Lys
225                 230                 235                 240

Ile Ile Pro Val Phe Gln Glu Asn Thr Leu Ile Gly Val Lys Leu Glu
                245                 250                 255

Asp Phe Glu Asp Trp Cys Lys Val Ala Lys Leu Ile Glu Gly Lys Lys
                260                 265                 270

His Leu Thr Glu Ser Gly Leu Asp Glu Ile Lys Lys Ile Lys Leu Asn
            275                 280                 285

Met Asn Lys Gly Arg
        290

<210> SEQ ID NO 82
<211> LENGTH: 293
<212> TYPE: PRT
<213> ORGANISM: Artificial Sequence
<220> FEATURE:
<223> OTHER INFORMATION: Synthesized I-OnuI variant CBLB.B5

<400> SEQUENCE: 82

Ser Ile Asn Pro Trp Ile Leu Thr Gly Phe Ala Asp Ala Glu Gly Cys
1               5                   10                  15

Phe Arg Leu Asp Ile His Asn Ala Asn Val Leu Arg Ser Gly Tyr Arg
                20                  25                  30

Thr Arg Leu Ser Phe Glu Ile Val Leu His Asn Lys Asp Lys Ser Ile
            35                  40                  45

Leu Glu Asn Ile Gln Ser Thr Trp Lys Val Gly Thr Ile Tyr Asn Ala
        50                  55                  60

Gly Asp Asn Ala Val Arg Leu Gln Val Thr Arg Phe Glu Asp Leu Lys
65                  70                  75                  80

Val Ile Ile Asp His Phe Glu Lys Tyr Pro Leu Ile Thr Gln Lys Leu
                85                  90                  95

Gly Asp Tyr Lys Leu Phe Lys Gln Ala Phe Ser Leu Met Glu Asn Lys
                100                 105                 110

Glu His Leu Lys Glu Asn Gly Ile Lys Glu Leu Val Arg Ile Lys Ala
            115                 120                 125

Lys Met Asn Trp Gly Leu Asn Asp Glu Leu Lys Lys Ala Phe Pro Glu
        130                 135                 140

Asn Ile Ser Lys Glu Arg Pro Leu Ile Asn Lys Asn Ile Pro Asn Leu
```

```
                145                 150                 155                 160
Lys Trp Leu Ala Gly Phe Thr Ser Gly Asp Gly Ser Phe Val Val Glu
                165                 170                 175

Leu Lys Lys Arg Arg Ser Pro Val Lys Val Gly Val Arg Leu Arg Phe
                180                 185                 190

Gly Ile Thr Gln His Ile Arg Asp Lys Asn Leu Met Asn Ser Leu Ile
                195                 200                 205

Thr Tyr Leu Gly Cys Gly Arg Ile Val Glu Asn Asn Lys Ser Glu His
    210                 215                 220

Ser Trp Leu Glu Phe Ile Val Thr Lys Phe Ser Asp Ile Asn Asp Lys
225                 230                 235                 240

Ile Ile Pro Val Phe Gln Glu Asn Thr Leu Ile Gly Val Lys Leu Glu
                245                 250                 255

Asp Phe Glu Asp Trp Cys Lys Val Ala Lys Leu Ile Glu Glu Lys Lys
                260                 265                 270

His Leu Thr Glu Ser Gly Leu Asp Glu Ile Lys Lys Ile Lys Leu Asn
                275                 280                 285

Met Asn Lys Gly Arg
                290

<210> SEQ ID NO 83
<211> LENGTH: 293
<212> TYPE: PRT
<213> ORGANISM: Artificial Sequence
<220> FEATURE:
<223> OTHER INFORMATION: Synthesized I-OnuI variant CBLB.A8

<400> SEQUENCE: 83

Ser Ile Asn Pro Trp Ile Leu Thr Gly Phe Ala Asp Ala Glu Gly Cys
1               5                   10                  15

Phe Arg Leu Asp Ile Arg Asn Ala Asn Asp Leu Arg Ala Gly Tyr Arg
                20                  25                  30

Thr Arg Leu Ala Phe Glu Ile Val Leu His Asn Lys Asp Lys Ser Ile
            35                  40                  45

Leu Glu Asn Ile Gln Ser Thr Trp Lys Val Gly Thr Ile Tyr Asn Ala
50                  55                  60

Gly Asp Asn Ala Val Arg Leu Gln Val Thr Arg Phe Glu Asp Leu Lys
65                  70                  75                  80

Val Ile Ile Gly His Phe Glu Lys Tyr Pro Leu Ile Thr Gln Lys Leu
                85                  90                  95

Gly Asp Tyr Lys Leu Phe Lys Gln Ala Phe Ser Val Met Glu Asn Lys
                100                 105                 110

Glu His Leu Lys Glu Asn Gly Ile Lys Glu Leu Val Arg Ile Lys Ala
            115                 120                 125

Lys Met Asn Trp Gly Leu Asn Asp Glu Leu Lys Lys Ala Phe Pro Glu
130                 135                 140

Asn Ile Ser Lys Glu Arg Pro Leu Ile Asn Lys Asn Ile Pro Asn Leu
145                 150                 155                 160

Lys Trp Leu Ala Gly Phe Thr Ser Gly Asp Gly Ser Phe Met Val Glu
                165                 170                 175

Leu Met Lys Asn Lys Asn Val Ile Val Arg Val Arg Leu Arg Phe
                180                 185                 190

Ser Ile Ser Gln His Ile Arg Asp Lys Asn Leu Met Asn Ser Leu Ile
            195                 200                 205

Thr Tyr Leu Gly Cys Gly Arg Ile Val Glu Asn Asn Lys Ser Glu His
```

```
           210                 215                 220
Ser Trp Leu Glu Phe Ile Val Thr Lys Phe Ser Asp Ile Asn Asp Lys
225                 230                 235                 240

Ile Ile Pro Val Phe Gln Glu Asn Thr Leu Ile Gly Val Lys Leu Glu
                245                 250                 255

Asp Phe Glu Asp Trp Cys Lys Val Ala Lys Leu Ile Glu Glu Lys Lys
                260                 265                 270

His Leu Thr Glu Ser Gly Leu Asp Glu Ile Lys Lys Ile Lys Leu Asn
                275                 280                 285

Met Asn Lys Gly Arg
    290

<210> SEQ ID NO 84
<211> LENGTH: 39
<212> TYPE: DNA
<213> ORGANISM: Homo sapiens

<400> SEQUENCE: 84
tggggatggg aatatcttac agaccatacc tcataacaa                              39
```